US005643756A

United States Patent [19]
Kayman et al.

[11] Patent Number: 5,643,756
[45] Date of Patent: Jul. 1, 1997

[54] FUSION GLYCOPROTEINS

[75] Inventors: Samuel Kayman, New York; Abraham Pinter, Brooklyn, both of N.Y.

[73] Assignee: The Public Health Research Institute of the City of New York, Inc., New York, N.Y.

[21] Appl. No.: 110,300

[22] Filed: Aug. 20, 1993

Related U.S. Application Data

[63] Continuation-in-part of Ser. No. 938,100, Aug. 28, 1992, abandoned.

[51] Int. Cl.$^6$ .......................... C12N 5/10; C12N 15/85; C12P 21/02
[52] U.S. Cl. .................. 435/69.7; 435/320.1; 435/325; 435/357
[58] Field of Search ........................ 435/69.7, 240.2, 435/320.1; 536/23.4

[56] References Cited

U.S. PATENT DOCUMENTS

| | | | |
|---|---|---|---|
| 4,701,416 | 10/1987 | Nunberg | 435/320.1 |
| 5,266,478 | 11/1993 | Chang et al. | 435/240.27 |

FOREIGN PATENT DOCUMENTS

| | | |
|---|---|---|
| 0356409 | 2/1990 | European Pat. Off. ......... C12P 21/02 |
| WO93/14188 | 7/1993 | WIPO . |
| WO93/20221 | 10/1993 | WIPO . |
| WO94/11524 | 5/1994 | WIPO . |
| WO94/27643 | 12/1994 | WIPO . |

OTHER PUBLICATIONS

Alberts et al., Molecular Biology of the Cell (Garland Publishing, Inc., New York, 1983), p. 172.

Wu, Kayman, Honen, Revesz, Chen, Vijh–Warrier, Tilley, McKeating, Shotton & Pinter, "Characterization of Neutralization Epitopes in the V2 Region of Human Immunodeficiency Virus Type 1 gp120: Role of Glycosylation in the Correct Folding of the V1/V2 Domain", Journal of Virology, Apr. 1995, vol. 69, pp. 2271–2278.

Battini, J., Heard, J.A., Danos, O., "Receptor Choice Determinants in the Envelope Glycoproteins of Amphotropic, Xenotropic, and Polytropic Murine Leukemia Viruses," 1992, Journal of Virology, vol. 66, pp. 1468–1475.

Benjouad, A., Gluckman, G–C., Rochat, H., Montagnier, L., Bahraoui, E., "Influence of Carbohydrate Moieties on the Immunogenicity of Human Immunodeficiency Virus Type 1 Recombinant gp160," 1992, Journal of Virology, vol. 66, No. 4, pp. 2473–2483.

Buchbinder, A., Karwowska, S., Gorny, M.K., Burda, S.T., Zolla–Pazner, S., "Synergy Between Human Monoclonal Antibodies to HIV Extends Their Effective Biologic Activity Against Homologous and Divergent Strains," 1992, Aids Research and Human Retroviruses, vol. 8, No. 4, pp. 425–427.

Fenouillet, E., Clerget–Raslain, B., Gluckman, J.C., Guetard, D., Montagnier, L., Bahroui, E., "Role of N–Linked Glycans in the Interaction Between the Envelope Glycoprotein of Human Immunodeficiency Virus and Its CD4 Cellular Receptor," 1989, J. Exp. Med., vol. 169, pp. 807–822.

Fenouillet, E., Gluckman, J–C., Bahroui, E., "Role of N–Linked Glycans of Envelope Glycoproteins in Infectivity of Human Immunodeficiency Virus Type 1," 1990, Journal of Virology, vol. 64, No. 6, pp. 2841–2848.

Fung, M.S.C., Sun, C.R.Y., Gordon, W.L., Liou, R–S., Chang, T.W., Sun, W.N.C., Daar, E.S., Ho, D.D., "Identification and Characterization of a Neutralization Site within the Second Variable Region of Human Immunodeficiency Virus Type 1 gp120," 1992, Journal of Virology, vol. 66, No. 2, pp. 848–856.

Haigwood, N.L., Nara, P.L., Brooks, E., Van Nest, G.A., Ott, G., Higgins, K.W., Dunlop, N., Scandella, C.J., Eichberg, J.W., Steimer, K.S., "Native but Not Denatured Recombinant Human Immunodeficiency Virus Type 1 gp120 Generates Broad–Spectrum Neutralizing Antibodies in Baboons," 1992, Journal of Virology, vol. 66, No. 1, pp. 172–182.

Heard, J.M., and Danos, O. "An Amino–Terminal Fragment of the Friend Murine Leukemia Virus Envelope Glycoprotein Binds the Ecotropic Receptor," 1991, Journal of Virology, vol. 65, No. 8, pp. 4026–4032.

Ho, D.D., Fung, M.S.C., Cao, Y., Li, X.L., Sun, C., Chang, T.W., Sun, N–C., "Another discontinuous epitope on glycoprotein gp120 that is important in human immunodeficiency virus type 1 neutralization is identified by a monoclonal antibody," 1991, Proc. Natl. Acad. Sci., U.S.A. vol. 88, pp. 8949–8952.

Ho, D.D., Sarngadharan, M.G., Hirsch, M.S., Schooley, R.T., Rota, T.R., Kennedy, R.C., Chanh, T.C., Sato, V., "Human Immunodeficiency Virus Neutralizing Antibodies Recognize Several Conserved Domains on the Envelope Glycoproteins," 1987, Journal of Virology, vol. 61, pp. 2024–2028.

Kayman, S.C., Kopelman, R., Projan, S., Kinney, D.M., Pinter, A., "Mutational Analysis of N–Linked Glycosylation Sites of Friend Murine Leukemia Virus Envelope Protein," 1991, Journal of Virology, vol. 65, No. 10, pp. 5323–5332. Kennedy, M.S., Orloff, S., Ibegbu, C.C., Odell, C.D., Maddon, P.J., McDougal, J.S., "Analysis of Synergism/Antagonism Between HIV–1 Antibody–Positive Human Sera and Soluble CD4 in Blocking HIV–1 Binding and Infectivity," 1991, Aids Research and Human Retroviruses, vol. 7, No. 12, pp. 975–981.

(List continued on next page.)

Primary Examiner—Mindy Fleisher
Assistant Examiner—Nancy J. Degen
Attorney, Agent, or Firm—William J. Hone

[57] ABSTRACT

Novel expression vectors are provided for expressing a fusion glycoprotein. The fusion glycoprotein contains the N-terminal globular domain of a retroviral env surface protein linked to a selected glycopeptide. Truncation glycoproteins as well as insertion glycoproteins are expressed using the vectors.

74 Claims, 19 Drawing Sheets

OTHER PUBLICATIONS

Leonard, C.K., Spellman, M.W., Riddle, L., Harris, R.J., Thomas, J.N., Gregory, T.J., "Assignment of Intrachain Disulfide Bonds and Characterization of Potential Glycosylation Sites of the Type 1 Recombinant Human Immunodeficiency Virus Envelope Glycoprotein (gp120) Expressed in Chinese Hamster Ovary Cells," 1990, *Journal of Biological Chemistry*, vol. 265, No. 18, pp. 10373–10382.

Lynch, C.M., Miller, A.D., "Production of High–Titer Helper Virus–Free Retroviral Vectors by Cocultivation of Packaging Cells with Different Host Ranges," 1991, *Journal of Virology*, vol. 65, No. 7, pp. 3887–3890.

Mace, M.C., Hansen, M., Whiting, S., Wang, C–T., Barklis, E., "Retroviral Envelope Protein Fusions to Secreted and Membrane Markers," 1992, *Virology*, 188, pp. 869–874.

Matthews, T.J., Weinhold, K.J., Lyerly, H.K., Langlois, A.J., Wigzell, H., Bolognesi, D.P., "Interaction between the human T–cell lymphotropic virus type $III_B$ envelope glycoprotein gp120 and the surface antigen CD4: Role of carbohydrate in binding and cell fusion," 1987, *Proc. Natl. Acad. Sci. U.S.A.*, vol. 84, pp. 5424–5428.

Ott, D., Rein, A., "Basis for Receptor Specificity of Non-ecotropic Murine Leukemia Virus Surface Glycoprotein $gp70^{SU}$," 1992, *Journal of Virology*, vol. 66, pp. 4632–4638.

Pollard, S.R., Rosa, M.D., Rosa, J.J., Wiley, D.C., "Truncated variants of gp120 bind CD4 with high affinity and suggest a minimum CD4 binding region," 1992, *The EMBO Journal*, vol. 11, No. 2, pp. 585–591.

Posner, M., Mukherjee, M., Hideshima, T., Cannon, T.C., Mayer, K., "Development of an IgG–1 Human Monoclonal Antibody that Neutralizes HIV–1 Infectivity and Binding and Reacts with a Cell Surface Antigen Expressed by HIV–1 Infected Cells," 1990, VI Int'l. Conf. on AIDS, San Francisco, CA, Abstract Th.A.77.

Russell, S.J., Hawkins, R.E., Winter, G., "Retroviral vectors displaying functional antibody fragments," 1993, *Nucleic Acids Research*, vol. 21, No. 5, pp. 1081–1085.

Stephens, D.M., Davis, D., Lachmann, P.J., "The Second Variable Region of HIV–1 External Envelope Glycoprotein Contains a Neutralizing Epitope," 1991, VII Int'l Conf. on AIDS, Florence, Italy, Abstract TH.A.66.

Tilley, S.A., Honnen, W.J., Racho, M.E., Hilgarter, M., Pinter, A., "Human Monoclonal Antibodies Against the Putative CD4 Binding Site and the V3 Loop of HIV gp120 Act in Concert to Neutralize Virus," 1991, VII Int'l. Conf. on AIDS, Florence, Italy, Abstract MA.70.

Tilley, S.A., Honnen, W.J., Racho, M.E., Hilgarter, M., Pinter, A., "Very Broadly Neutralizing Human Monoclonal Antibody (HuMAb) Against the CD4–Binding Site of HIV–1 gp120," VIII Int'l. Conf. on AIDS/III STD World Congress, Amsterdam, The Netherlands, Abstract.

Tilley, S.A., Honnen, W.J., Racho, M.E., Chou, T–C., Pinter, A., "Synergistic Neutralization of HIV–1 by Human Monoclonal Antibodies Against the V3 Loop and the CD4–Binding Site of gp120," 1992, *Aids Research and Human Retroviruses*, vol. 8, No. 4, pp. 461–467.

Tilley, S.A., Honnen, W.J., Warrier, S., Racho, M.E., Chou, T–C., Girard, M., Muchmore, E., Hilgartner, M., Ho, D.D., Fung, M.S.C., Pinter, A., "Potent Neutralization of HIV–1 by Human and Chimpanzee Monoclonal Antibodies Directed Against Three Distinct Epitope Clusters of gp 120," 1991, Sixieme Coloque Des Cent Gardes, pp., 211–216.

Young, J.A.T., Bates, P., Willert, K., Varmus, H.E., "Efficient Incorporation of Human CD4 Protein into Avian Leukosis Virus Particles," 1990, *Science*, vol. 250, pp. 1421–1423.

Wills, J.W., "Retro–secretion of recombinant proteins," 1989, *Nature*, vol. 340, pp. 323–324.

FIG. 1A

```
         |   10      |   20      |   30      |   40
   1   GCGCCAGTCC TCCGATAGAC TGAGTCGCCC GGGTACCCGT
  41   GTATCCAATA AATCCTCTTG CTGTTGCATC CGACTCGTGG
  81   TCTCGCTGTT CCTTGGGAGG GTCTCCTCAG AGTGATTGAC
 121   TACCCGTCTC GGGGGTCTTT CATTTGGGGG CTCGTCCGGG
 161   ATCTGGAGAC CCCTGCCCAG GGACCACCGA CCCACCACCG
 201   GGAGGTAAGC TGGCCAGCAA TTGTTCTGTG TCTGTCCATT
 241   GTCCTGTGTC TTTGATTGAT TTTATGCGCC TGTGTCTGTA
 281   CTAGTTGGCC GACTAGATTG GTATCTGGCG GATCCGTGGT
 321   GGAACTGACG AGTTCGAGAC ACCCGGCCGC AACCCTGGGA
 361   GACGTCCAG  GGACTTCGGG GGCCATTTTT GTGGCCCGGC
 401   CAGAGTCCAA CCATCCCGAT CGTTTTGGAC TCTTTGGTGC
 441   ACCCCCTTA  GAGGAGGGGT ATGTGGTTCT GGTAGGAGAC
 481   AGAGGGCTAA AACGGTTTCC GCCCCGTCT  GAGTTTTTGC
 521   TTTCGGTTTG GAACCGAAGC CGCGCCGCGC GTCTTGTCTG
 561   CTGCAGCATC GTTCTGTGTT GTCTCTGTTT GACTGTTTTT
 601   CTGTATTTGT CTGAAAACAT GGGCCAGGCT GTTACCACCC
 641   CCTTAAGTTT GACTTTAGAC CACTGGAAGG ATGTCGAACG
 681   GACAGCCCAC AACCTGTCGG TAGAGGTTAG AAAAAGGCGC
 721   TGGGTTACAT TCTGCTCTGC AGAATGGCCA ACCTTAACG
 761   TCGGATGGCC ACGAGACGGC ACTTTTAACC CAGACATTAT
 801   TACACAGGTT AAGATCAAGG TCTTCTCACC TGGCCCACAT
 841   GGACATCGG  ATCAGGTCCC CTACATCGTG ACCTGGGAAG
 881   CTATAGCAGT AGACCCCCT  CCCTGGGTCA GACCCTTCGT
 921   GCACCCTAAA CCTCCCTCT  CTCTTCCCCC TTCAGCCCCC
 961   TCTCTCCCAC CTGAACCCCC ACTCTCGACC CCGCCCCAGT
1001   CCTCCCTCTA TCCGGCTCTC ACTTCTCCTT TAAACACCAA
1041   ACCTAGGCCT CAAGTCCTTC CTGATAGCGG AGGACCACTC
1081   ATTGATCTAC TCACGGAGGA CCCTCCGCCT TACCGGGACC
1121   CAGGGCCACC CTCTCCTGAC GGGAACGGCG ATAGCGGAGA
1161   AGTGGCCCCT ACAGAAGGAG CCCCTGACCC TTCCCCAATG
1201   GTATCCCGCC TGCGGGAAG  AAAAGAACCC CCCGTGGCGG
1241   ATTCTACTAC CTCTCAGGCG TTCCCCCTTC GCCTGGGAGG
1281   GAATGGACAG TATCAATACT GGCCATTTTC CTCCTCTGAC
1321   CTCTATAACT GGAAAATAA  CAACCCCTCT TTCTCCGAGG
1361   ACCCAGCTAA ATTGACAGCT TTGATCGAGT CCGTTCTCCT
1401   TACTCATCAG CCCACTTGGG ATGACTGCCA ACAGCTATTA
1441   GGGACCCTGC TGACGGGAGA AGAAAAACAG CGAGTGCTCC
1481   TAGAGGCCCG AAAGGCGGTT CGAGGGGAGG ACGGACGCCC
1521   AACTCAGCTG CCCAATGACA TTAATGATGC TTTTCCCTTG
1561   GAACGTCCCG ACTGGGACTA CAACACCCAA CGAGGTAGGA
1601   ACCACCTAGT CCACTATCGC CAGTTGCTCC TAGCGGGTCT
```

FIG. 1B

```
         |       10        |       20        |       30        |       40
1641    CCAAAACGCG    GGCAGAAGCC    CCACCAATTT    GGCCAAGGTA
1681    AAAGGGATAA    CCCAGGGACC    TAATGAGTCT    CCCTCAGCCT
1721    TTTTAGAGAG    ACTCAAGGAG    GCCTATCGCA    GATACACTCC
1761    TTATGACCCT    GAGGACCCAG    GGCAAGAAAC    CAATGTGGCC
1801    ATGTCATTCA    TCTGGCAGTC    CGCCCCGGAT    ATCGGGCGAA
1841    AGTTAGAGCG    GTTAGAAGAT    TTGAAGAGTA    AGACCTTAGG
1881    AGACTTAGTG    AGGGAAGCTG    AAAAGATCTT    TAATAAACGA
1921    GAAACCCCGG    AAGAAAGAGA    GGAACGTATT    AGGAGAGAAA
1961    CAGAGGAAAA    GGAAGAACGC    CGTAGGGCAG    AGGATGTGCA
2001    GAGAGAGAAG    GAGAGGGACC    GCAGAAGACA    TAGAGAAATG
2041    AGTAAGTTGC    TGGCTACTGT    CGTTAGCGGG    CAGAGACAGG
2081    ATAGACAGGG    AGGAGAGCGA    AGGAGGCCCC    AACTCGACCA
2121    CGACCAGTGT    GCCTACTGCA    AAGAAAGGG    ACATTGGCT
2161    AGAGATTGCC    CCAAGAAGCC    AAGAGGACCC    CGGGGACCAC
2201    GACCCCAGGC    CTCCCTCCTG    ACCTTAGACG    ATTAGGGAGG
2241    TCAGGGTCAG    GAGCCCCCCC    CTGAACCCAG    GATAACCCTC
2281    AGAGTCGGGG    GGCAACCCGT    CACCTTCCTA    GTGGATACTG
2321    GGGCCCAACA    CTCCGTGCTG    ACCCAAAATC    CTGGACCCCT
2361    AAGTGACAAG    TCTGCCTGGG    TCCAAGGGGC    TACTGGAGGG
2401    AAGCGGTATC    GCTGGACCAC    GGATCGCCGA    GTGCACCTAG
2441    CCACCGGTAA    GGTCACCCAT    TCTTTCCTCC    ATGTACCAGA
2481    TTGCCCCTAT    CCTCTGCTAG    GAAGAGATTT    GCTGACTAAA
2521    CTAAAAGCCC    AAATTCACTT    TGAGGGATCA    GGAGCTCAGG
2561    TTGTGGGACC    AATGGGACAG    CCCCTGCAAG    TGCTGACCCT
2601    AAACATAGAA    GATGAGTATC    GGCTACATGA    GACCTCAAAA
2641    GGGCCAGATG    TGCCTCTAGG    GTCCACATGG    CTCTCTGATT
2681    TTCCCCAGGC    CTGGGCAGAA    ACCGGGGCA    TGGGGCTGGC
2721    CGTTCGCCAA    GCTCCTCTGA    TCATACCTCT    GAAGGCAACC
2761    TCTACCCCCG    TGTCCATAAA    ACAATACCCC    ATGTCACAAG
2801    AAGCCAGACT    GGGGATCAAG    CCCCACATAC    AGAGACTGCT
2841    GGATCAGGGA    ATTCTGGTAC    CCTGCCAGTC    CCCCTGGAAC
2881    ACGCCCTGC    TACCCGTTAA    GAAACGGGG    ACTAATGATT
2921    ATAGGCCTGT    CCAGGATCTG    AGAGAAGTCA    ACAAGCGGGT
2961    GGAAGACATC    CACCCCACCG    TGCCCAACCC    TTACAACCTC
3001    TTGAGCGGGC    TCCCACCGTC    CACCAGTGG    TACACTGTGC
3041    TTGACTTAAA    AGATGCTTTT    TTCTGCCTGA    GACTCCACCC
3081    CACCAGTCAG    TCTCTCTTCG    CCTTTGAGTG    GAGAGATCCA
3121    GAGATGGGAA    TCTCAGGACA    ATTAACCTGG    ACCAGACTCC
3161    CGCAGGGTTT    CAAAAACAGT    CCCACCCTGT    TTGATGAAGC
3201    CCTGCACAGG    GACCTCGCAG    ACTTCCGGAT    CCAGCACCCA
3241    GACCTGATTC    TGCTCCAGTA    TGTAGATGAC    TTACTGCTGG
3281    CCGCCACTTC    TGAGCTTGAC    TGTCAACAAG    GTACGCGGC
3321    CCTGTTACAA    ACCCTAGGGG    ACCTCGGATA    TCGGGCCTCG
3361    GCCAAGAAAG    CCCAAATTTG    CCAGAAACAG    GTCAAGTATC
```

FIG. 1C

```
              |  10       |  20        |  30       |  40
3401   TGGGGTATCT TCTAAAAGAG GGTCAGAGAT GGCTGACTGA
3441   GGCCAGAAAA GAGACTGTGA TGGGCAGCC  TACTCCGAAG
3481   ACCCCTCGAC AACTAAGGGA GTTCCTAGGG ACGGCAGGCT
3521   TCTGTCGCCT CTGGATCCCT GGGTTTGCAG AAATGGCAGC
3561   CCCCTTGTAC CCTCTCACCA AAACGGGGAC TCTGTTTGAG
3601   TGGGGCCCAG ACCAGCAAAA GGCCTACCAA GAGATCAAGC
3641   AGGCTCTCTT AACTGCCCCT GCCTGGGAT  TGCCAGACTT
3681   GACTAAGCCC TTCGAACTTT TTGTTGACGA GAAGCAGGGC
3721   TACGCCAAAG GTGTCCTAAC GCAAAAACTG GGGCCTTGGC
3761   GTCGGCCGGT GGCCTACCTG TCCAAAAAGC TAGACCCAGT
3801   GGCAGCTGGG TGGCCCCCTT GCCTACGGAT GGTAGCAGCC
3841   ATCGCCGTTC TGACCAAAGA CGCTGGCAAG CTCACCATGG
3881   GACAGCCACT AGTCATTCTG GCCCCCATG  CAGTAGAGGC
3921   ACTAGTTAAG CAACCCCCTG ATCGCTGGCT CTCCAACGCC
3961   CGAATGACCC ACTACCAGGC TCTGCTTCTG GACACGGACC
4001   GAGTCCAGTT CGGACCAATA GTGGCCCTAA ACCCAGCTAC
4041   GCTGCTCCCT CTACCTGAGG AGGGGCTGCA ACATGACTGC
4081   CTTGACATCT TGGCTGAAGC CCACGGAACT AGACCAGATC
4121   TTACGGACCA GCCTCTCCCA GACGCTGACC ACACCTGGTA
4161   CACAGATGGG AGCAGCTTCC TGCAAGAGGG GCAGCGCAAG
4201   GCCGGAGCAG CAGTAACCAC CGAGACCGAG GTAGTCTGGG
4241   CCAAAGCACT GCCAGCCGGG ACATCGGCCC AAAGAGCTGA
4281   GTTGATAGCG CTCACCCAAG CCTTAAAAAT GGCAGAAGGT
4321   AAGAAGCTGA ATGTTTACAC CGATAGCCGT TATGCTTTTG
4361   CCACTGCCCA TATTCACGGA GAAATATATA GAAGGCGCGG
4401   GTTGCTCACA TCAGAAGGAA AAGAAATCAA AAATAAGGAC
4441   GAGATCTTGG CCCTACTGAA GGCTCTCTTC CTGCCCAAAA
4481   GACTTAGCAT AATTCATTGC CCGGGACATC AGAAGGGAAA
4521   CCGCGCGGAG GCAAGGGGCA ACAGGATGGC CGACCAAGCG
4561   GCCCGAGAAG TAGCCACTAG AGAAACTCCA GAGACTTCCA
4601   CACTTCTGAT AGAAAATTCA GCCCCCTATA CTCATGAACA
4641   TTTTCACTAT ACGGTGACTG ACATAAAAGA TCTGACTAAA
4681   CTAGGGGCCA CTTATGACGA TGCAAAGAAG TGTTGGGTTT
4721   ATCAGGGAAA GCCTGTAATG CCTGATCAAT TCACCTTTGA
4761   ACTATTAGAT TTTCTTCATC AATTGACCCA CCTCAGTTTC
4800   TCAAAAACAA AGGCTCTTCT AGAAAGGAAC TACTGTCCTT
4841   ATTACATGCT GAACCGGGAT CGAACGCTCA AGACATCAC
4881   TGAGACTTGC CAAGCCTGTG CACAGGTCAA TGCCAGCAAG
4921   TCTGCCGTCA AACAAGGGAC TAGAGTTCGA GGGCACCGAC
4961   CCGGCACCCA CTGGGAAATT GATTTCACTG AGGTAAAACC
5001   TGGCCTGTAT GGGTATAAAT ATCTTTTAGT TTTCATAGAC
5041   ACTTTCTCTG GATGGGTAGA AGCTTTCCCA ACCAAGAAAG
5081   AAACTGCCAA AGTTGTAACC AAGAAGCTAC TAGAAGAAAT
5121   CTTCCCCAGA TTCGGCATGC CACAGGTATT GGGAACCGAC
```

FIG. 1D

```
             |        10         |        20         |        30         |        40
5161    AATGGGCCTG    CCTTCGTCTC    CAAGGTAAGT    CAGACAGTAG
5201    CCGATTTACT    GGGGGTTGAT    TGGAAACTAC    ATTGTGCTTA
5241    CAGACCCCAG    AGTTCAGGTC    AGGTAGAAAG    AATGAATAGG
5281    ACAATCAAGG    AGACTTTAAC    TAAATTGACG    CTTGCAACTG
5321    GCTCTAGGGA    CTGGGTGCTC    CTGCTTCCCC    TAGCCCTGTA
5361    TCGAGCCCGC    AACACGCCGG    GCCCCATGG     TCTCACCCCA
5401    TATGAAATCT    TATATGGGGC    ACCCCGCCC     CTTGTAAACT
5441    TCCCTGATCC    TGACATGGCA    AAGGTTACTC    ATAACCCCTC
5481    TCTCCAAGCC    CATTTACAGG    CACTCTACCT    GGTCCAGCAC
5521    GAAGTCTGGA    GACCGTTGGC    GGCAGCTTAC    CAAGAACAAC
5561    TGGACCGGCC    GGTAGTGCCT    CACCCTTTCC    GAGTCGGTGA
5601    CACAGTGTGG    GTCCGCAGAC    ACCAAACTAA    AAATCTAGAA
5641    CCCCGCTGGA    AAGGACCTTA    TACCGTCCTA    CTGACTACCC
5681    CCACCGCTCT    CAAAGTGGAC    GGCATTGCAG    CGTGGATCCA
5721    CGCTGCCCAC    GTAAAGGCTG    CCGACACCAG    GATTGAGCCA
5761    CCATCGGAAT    CGACATGGCG    TGTTCAACGC    TCTCAAAATC
5801    CCCTAAAGAT    AAGATTGACC    CGCGGGACCT    CCTAATCCCC
5841    TTAATTCTCT    TCCTGTCTCT    CAAAGGGGCC    AGATCCGCAG
5881    CACCCGGCTC    CAGCCCTCAC    CAGGTCTACA    ACATTACCTG
5921    GGAAGTGACC    AATGGGGATC    GGGAGACAGT    ATGGGCAATA
5961    TCAGGCAACC    ACCCTCTGTG    GACTTGGTGG    CCAGTCCTCA
6001    CCCCAGATTT    GTGTATGTTA    GCTCTCAGTG    GGCCGCCCCA
6041    CTGGGGGCTA    GAGTATCAGG    CCCCTATTC     CTCGCCCCCG
6081    GGGCCCCCTT    GTTGCTCAGG    GAGCAGCGGG    AACGTTGCAG
6121    GCTGTGCCAG    AGACTGCAAC    GAGCCCTTGA    CCTCCCTCAC
6161    CCCTCGGTGC    AACACTGCCT    GGAACAGACT    TAAGCTGGAC
6201    CAGGTAACTC    ATAAATCAAG    TGAGGGATTT    TATGTCTGCC
6241    CCGGGTCACA    TCGCCCCGG     GAAGCCAAGT    CCTGTGGGGG
6281    TCCAGACTCC    TTCTACTGTG    CCTCTTGGGG    CTGCGAGACA
6321    ACCGGTAGAG    TATACTGGAA    GCCCTCCTCT    TCTTGGGACT
6361    ACATCACAGT    AGACAACAAT    CTCACCTCTA    ACCAGGCTGT
6401    TCAGGTATGC    AAAGACAATA    AGTGGTGCAA    TCCCTTGGCT
6441    ATCCGGTTTA    CAAACGCCGG    GAAACAGGTC    ACCTCATGGA
6481    CAACTGGACA    CTATTGGGGT    CTACGTCTTT    ATGTCTCTGG
6521    ACAGGACCCA    GGGCTTACTT    TCGGGATCCG    ACTCAGTTAT
6561    CAAAATCTAG    GACCTCGGAT    CCAATAGGA     CCAAACCCCG
6601    TCCTGGCAGA    CCAACTTTCG    TTCCCGCTAC    CTAATCCCCT
6641    ACCCAAACCT    GCCAAGTCTC    CCCCCGCCTC    TAGTTCGACT
6681    CCCACATTGA    TTTCCCCGTC    CCCCACTCCC    ACTCAGCCCC
6721    CGCCAGCAGG    AACGGGAGAC    AGATTACTAA    ATCTAGTACA
6761    GGGAGCTTAC    CAGGCACTCA    ACCTTACCAA    CCCTGATAAA
6801    ACTCAAGAGT    GCTGGTTATG    CCTAGTGTCT    GGACCCCCT
6841    ATTACGAGGG    GGTTGCCGTC    CTAGGTACTT    ATTCCAACCA
6881    TACCTCTGCC    CCAGCTAACT    GCTCCGTGGC    CTCCCAACAC
```

FIG. 1E

```
              |   10        |   20        |   30        |   40
6921    AAGCTGACCC   TGTCCGAAGT   GACTGGACGG   GGACTCTGCA
6961    TAGGAACAGT   CCCAAAAACT   CACCAGGCCC   TGTGCAACAC
7001    TACCCTTAAG   GCAGGCAAAG   GGTCTTACTA   TCTAGTTGCC
7041    CCCACAGGAA   CTATGTGGGC   ATGTAACACT   GGACTCACTC
7081    CATGCCTATC   TGCCACCGTG   CTTAATCGCA   CCACTGACTA
7121    TTGCGTTCTC   GTGGAATTAT   GGCCCAGGGT   CACCTACCAT
7161    CCTCCCAGTT   ACGTCTATAG   CCAGTTTGAA   AAATCCCATA
7201    GACATAAAAG   AGAACCAGTG   TCCTTAACCT   TGGCCTTATT
7241    ATTAGGTGGG   CTAACTATGG   GTGGCATCGC   CGCGGGAGTA
7281    GGGACAGGAA   CTACCGCCCT   GGTCGCCACC   CAGCAGTTTC
7321    AGCAGCTCCA   TGCTGCCGTA   CAAGATGATC   TCAAAGAAGT
7361    CGAAAAGTCA   ATTACTAACC   TAGAAAAGTC   TCTTACTTCG
7401    TTGTCTGAGG   TTGTACTGCA   GAATCGACGA   GGCCTAGACC
7441    TGTTGTTCCT   AAAAGAGGGA   GGACTGTGTG   CTGCCCTAAA
7481    AGAAGAATGT   TGTTTCTATG   CTGACCATAC   AGGCCTAGTA
7521    AGAGATAGTA   TGGCCAAATT   AAGAGAGAGA   CTCTCTCAGA
7561    GACAAAAACT   ATTTGAGTCG   AGCCAAGGAT   GGTTCGAAGG
7601    ATGGTTTAAC   AGATCCCCCT   GGTTTACCAC   GTTGATATCC
7641    ACCATCATGG   GGCCTCTCAT   TATACTCCTA   CTAATTCTGC
7681    TTTTTGGACC   CTGCATTCTT   AATCGATTAG   TTCAATTTGT
7721    TAAAGACAGG   ATCTCAGTAG   TCCAGGCTTT   AGTCCTGACT
7761    CAACAATACC   ACCAGCTAAA   ACCACTAGAA   TACGAGCCAC
7801    AATAAATAAA   AGATTTTATT   TAGTTTCCAG   AAAAAGGGGG
7841    GAATGAAAGA   CCCCACCAAA   TTGCTTAGCC   TGATAGCCGC
7881    AGTAACGCCA   TTTTGCAAGG   CATGGAAAAA   TACCAAACCA
7921    AGAATAGAGA   AGTTCAGATC   AAGGGCGGGT   ACACGAAAAC
7961    AGCTAACGTT   GGGCCAAACA   GGATATCTGC   GGTGAGCAGT
8001    TTCGGCCCCG   GCCCGGGGCC   AAGAACAGAT   GGTCACCGCG
8041    GTTCGGCCCC   GGCCCGGGGC   CAAGAACAGA   TGGTCCCCAG
8081    ATATGGCCCA   ACCCTCAGCA   GTTTCTTAAG   ACCCATCAGA
8121    TGTTTCCAGG   CTCCCCCAAG   GACCTGAAAT   GACCCTGTGC
8161    CTTATTTGAA   TTAACCAATC   AGCCTGCTTC   TCGCTTCTGT
8201    TCGCGCGCTT   CTGCTTCCCG   AGCTCTATAA   AAGAGCTCAC
8241    AACCCTCAC   TCGGCGCGCC   AGTCCTCCGA   TAGACTGAGT
8281    CGCCCGGGTA   CCCGTGTATC   CAATAAATCC   TCTTGCTGTT
8321    GCA   (SEQ ID NO: 8)
```

FIG. 3A

```
             |       10 |       20 |       30 |       40
   1   gaactcgagc agggCTAGTA CAGACACAGG CGCATAAAAT
  41   CAATCAAAGA CACAGGACAA TGGACAGACA CAGAACAATT
  81   GCTGGCCAGC TTACCTCCCG GTGGTGGGTC GGTGGTCCCT
 121   GGGCAGGGGT CTCCAGATCC CGGACGAGCC CCCAAATGAA
 161   AGACCCCCGA GACGGGTAGT CAATCACTCT GAGGAGACCC
 201   TCCCAAGGAA CAGCGAGACC ACGAGTCGGA TGCAACAGCA
 241   AGAGGATTTA TTGGATACAC GGGTACCCGG GCGACTCAGT
 281   CTATCGGAGG ACTGGCGCGC CGAGTGAGGG GTTGTGAGCT
 321   CTTTTATAGA GCTCGGGAAG CAGAAGCGCG CGAACAGAAG
 361   CGAGAAGCAG GCTGATTGGT TAATTCAAAT AAGGCACAGG
 401   GTCATTTCAG GTCCTTGGGG GAGCCTGGAA ACATCTGATG
 441   GGTCTTAAGA AACTGCTGAG GGTTGGGCCA TATCTGGGA
 481   CCATCTGTTC TTGGCCCCGG GCCGGGGCCG AACCGCGGTG
 521   ACCATCTGTT CTTGGCCCCG GCCGGGGCC GAAACTGCTC
 561   ACCGCAGATA TCCTGTTTGG CCCAACGTTA GCTGTTTTCG
 601   TGTACCCGCC CTTGATCTGA ACTTCTCTAT TCTTGGTTTG
 641   GTATTTTTCC ATGCCTTGCA AAATGGCGTT ACTGCGGCTA
 681   TCAGGCTAAG CAACTTGGTG GGGTCTTTCA TTCCCCCCTT
 721   TTTCTGGAAA CTAAATAAAA TCTTTTATTT ATCATGGCTC
 761   GTATTCTAGT GGTTTTAGCT GGTGGTATTG TTGAGTCAGG
 801   ACTAAAGCCT GGACTACTGA GATCCTGTCT TTAACAAATT
 841   GAACTAATCG ATtcattagc tagcTCCTGC TGGCGGGGGC
 881   TGAGTGGGAG TGGGGGACGG GGAAATCAAT GTGGGAGTCG
 921   AATTAGAGGC GGGGGGAGAC TTGGCAGGTT TGGGTAGGGG
 961   ATTAGGTCGC GGGAGCGAAA GTTGGTCTGC CAGGACGGGG
1001   TTCGGTCCTA TCGGACCCG AGGTCCTAGA TTTTGATATC
1041   TGAGTCGGAT CCCGAAAGTA AGCCCCGGGT CCCGCCCAGA
1081   GACATAAAGA CGTAGACCCC AATAGTGTCC AGTTGTCCAT
1121   GAGGTGACCT GTTTCCCGGC GTTTGTAAAC TGGATAGCCA
1161   AGGGATTGCA CCACTTATTG TCTTTGCATA CCTGGACAGC
1201   CTGGCTAGTG GTGAGATTGT TGTCCACTGT GATGTAGTCC
1241   CAAGAGGAGG AGGGCTTCCA GTATACTCTA CCGGTTGTCT
1281   CGCAGCCCCA AGAGGCACAG TAGAAGGAGT CTGGACCTCC
1321   ACAGGACTTG GCTTCCCGGG GGCGATGTGA CCCGGGGCAG
1361   ACATAAAATC CCTCACTTGA TTTATGAGTT ACCTGGTCTA
1401   GCTTAAGTCT GTTCCAGGCA GTGTTGCACC GAGGGGTGAG
1441   GGAGGTCAAG GGCTCGTCGC AGTCTCTGGA ACAGCCTGCA
1481   CTGCTCCCGC TGCTCCCTGA GCAACAAGGG GGCCCCGGGG
1521   GCGAGGAATA GGGGGCCTGA TACTCTAGCC CCCAGTGGGG
1561   CGGCCCACTG AGAGCTAACA TACACAAATC TGGGGTGAGG
1601   ACTGGCCACC AAGTCCACAG AGGGTGGTTG CCTGATATTG
```

FIG. 3B

```
            |       10       |       20       |       30       |       40
1641   CCCATACTGT   CTCCCGATCC   CCATTGGTCA   CTTCCCAGGT
1681   AATGTTGTAG   ACCTGGTGAG   GGCTGGAGCC   GGGTGCTGCG
1721   GATCTGGCCC   CTTTGAGAGA   CAGGAAGAGA   ATTAAGGGGA
1761   TTAGGAGGTC   CCGCGGGTCA   ATCTTATCTT   TAGGGGATTT
1801   TGGGAGCGTT   GAACACGCCA   TGTCGATTCT   GCTGGTGGCT
1841   CAATCCTGGT   GTCGGCAGCC   TTTACGTGGG   CAGCGTGGAT
1881   CCACGCTGCA   ATGCCGTCTA   CTTTGAGAGC   GGTGGGGTA
1921   GTCAGTAGGA   CGGTATAGGG   TCCTTTCCAG   CGGGGTTCTA
1961   GATTTTTAGT   TTGGTGTCTG   CGGACCCACA   CTGTGTCACC
2001   GACCCGGAAA   GGGTGAGGTA   CTACCGGCCG   GTCTAGTTGC
2041   TCTTGGTAAG   CTGCCGCCAA   CGGTCTCCAG   ACTTCGTGCT
2081   GGACCAGGTA   GAGTGCCTGT   AAATGAGCTT   GGAGAGAGGG
2121   GTTATGAGTA   ACCTTTGCCA   TGTCAGGATC   AGGGAAGTTT
2161   ACAAGGGGCG   GGGGTGCCCC   ATATAAGATT   TCATATGGGG
2201   TGAGACCGTG   GGGGCCCGGC   GTGTTGCGGG   CTCGATACAG
2241   GGCAAGGGGA   AGCAGGAGCA   CCCAGTCCCT   AGAGCCAGTT
2281   GCAAGCGTCA   ATTTAGTTAA   AGTCTCCTTG   ATTGTCCTAT
2321   TCATTCTTTC   TACCTGACCT   GAACTCTGGG   GTCTGTAAGC
2361   ACAATGTAGT   TTCCAATCAA   CCCCCAATAA   ATCGGCTACT
2401   GTCTGACTTA   CCTTGGAGAC   GAAGGCAGGC   CCATTGTCGG
2441   TTCCCAATAC   CTGTGGCATG   CCGAATCTGG   GGAAGATTTC
2481   TTCTAGTAGC   TTCTTGGTTA   CAACTTTGGC   AGTTTCTTTC
2521   TTGGTTGGGA   AAGCTTCTAC   CCATCCAGAG   AAAGTGTCTA
2561   TGAAAACTAA   AAGATATTTA   TACCCATACA   GGCCAGGTTT
2601   TACCTCAGTG   AAATCAATTT   CCCAGTGGGT   GCCGGGTCGG
2641   TGCCCTCGAA   CTCTAGTCCC   TTGTTTGACG   GCAGACTTGC
2681   TGGCATTGAC   CTGTGCACAG   GCTTGGCAAG   TCTCAGTGAT
2721   GTCTTTGAGC   GTTCGATCCC   GGTTCAGCAT   GTAATAAGGA
2761   CAGTAGTTCC   TTTCTAGAAG   AGCCTTTGTT   TTTGAGAAAC
2801   TGAGGTGGGT   CAATTGATGA   AGAAAATCTA   ATAGTTCAAA
2841   GGTGAATTGA   TCAGGCATTA   CAGGCTTTCC   CTGATAAACC
2881   CAACACTTCT   TTGCATCGTC   ATAAGTGGCC   CCTAGTTTAG
2921   TCAGATCTTT   TATGTCAGTC   ACCGTATAGT   GAAAATGTTC
2961   ATGAGTATAG   GGGGCTGAAT   TTTCTATCAG   AAGTGTGGAA
3001   GTCTCTGGAG   TTTCTCTAGT   GGCTACTTCT   CGGGCCGCTT
3041   GGTCGGCCAT   CCTGTTGCCC   CTTGCCTCCG   CGCGGTTTCC
3081   CTTCTGATGT   CCCGGGCAAT   GAATTATGCT   AAGTCTTTTG
3121   GGCAGGAAGA   GAGCCTTCAG   TAGGGCCAAG   ATCTCGTCCT
3161   TATTTTTGAT   TTCTTTTCCT   TCTGATGTGA   GCAACCCGCG
3201   CCTTCTATAT   ATTTCTCCGT   GAATATGGGC   AGTGGCAAAA
3241   GCATAACGGC   TATCGGTGTA   AACATTCAGC   TTCTTACCTT
3281   CTGCCATTTT   TAAGGCTTGG   GTGAGCGCTA   TCAACTCAGC
3321   TCTTTGGGCC   GATGTCCCGG   CTGGCAGTGC   TTTGGCCCAG
```

FIG. 3C

```
          |        10         |        20         |        30         |        40
3361    ACTACCTCGG    TCTCGGTGGT    TACTGCTGCT    CCGGCCTTGC
3401    GCTGCCCCTC    TTGCAGGAAG    CTGCTCCCAT    CTGTGTACCA
3441    GGTGTGGTCA    GCGTCTGGGA    GAGGCTGGTC    CGTAAGATCT
3481    GGTCTAGTTC    CGTGGGCTTC    AGCCAAGATG    TCAAGGCAGT
3521    CATGTTGCAG    CCCCTCCTCA    GGTAGAGGGA    GCAGCGTAGC
3561    TGGGTTTAGG    GCCACTATTG    GTCCGAACTG    GACTCGGTCC
3601    GTGTCCAGAA    GCAGAGCCTG    GTAGTGGGTC    ATTCGGCGT
3641    TGGAGAGCCA    GCGATCAGGG    GGTTGCTTAA    CTAGTGCCTC
3681    TACTGCATGG    GGGGCCAGAA    TGACTAGTGG    CTGTCCCATG
3721    GTGAGCTTGC    CAGCGTCTTT    GGTCAGAACG    GCGATGGCTG
3761    CTACCATCCG    TAGGCAAGGG    GGCCACCCAG    CTGCCACTGG
3801    GTCTAGCTTT    TTGGACAGGT    AGGCCACCGG    CCGACGCCAA
3841    GGCCCCAGTT    TTTGCGTTAG    GACACCTTTG    GCGTAGCCCT
3881    GCTTCTCGTC    AACAAAAAGT    TCGAAGGGCT    TAGTCAAGTC
3921    TGGCAATCCC    AGGGCAGGGG    CAGTTAAGAG    AGCCTGCTTG
3961    ATCTCTTGGT    AGGCCTTTTG    CTGGTCTGGG    CCCCACTCAA
4001    ACAGAGTCCC    CGTTTTGGTG    AGAGGGTACA    AGGGGGCTGC
4041    CATTTCTGCA    AACCCAGGGA    TCCAGAGGCG    ACAGAAGCCT
4081    GCCGTCCCTA    GGAACTCCCT    TAGTTGTCGA    GGGGTCTTCG
4121    GAGTAGGCTG    CCCCATCACA    GTCTCTTTTC    TGGCCTCAGT
4161    CAGCCATCTC    TGACCCTCTT    TTAGAAGATA    CCCCAGATAC
4201    TTGACCTGTT    TCTGGCAAAT    TTGGGCTTTC    TTGGCCGAGG
4241    CCCGATATCC    GAGGTCCCCT    AGGGTTTGTA    ACAGGGCCCG
4281    CGTACCTTGT    TGACAGTCAA    GCTCAGAAGT    GGCGGCCAGC
4321    AGTAAGTCAT    CTACATACTG    GAGCAGAATC    AGGTCTGGGT
4361    GCTGGATCCG    GAAGTCTGCG    AGGTCCCTGT    GCAGGGCTTC
4401    ATCAAACAGG    GTGGGACTGT    TTTTGAAACC    CTGCGGAGT
4441    CTGGTCCAGG    TTAATTGTCC    TGAGATTCCC    ATCTCTGGAT
4481    CTCTCCACTC    AAAGGCGAAG    AGAGACTGAC    TGGTGGGGTG
4521    GAGTCTCAGG    CAGAAAAAAG    CATCTTTTAA    GTCAAGCACA
4561    GTGTACCACT    GGTGGACGG    TGGGAGCCCG    CTCAAGAGGT
4601    TGTAAGGGTT    GGGCACGGTG    GGTGGATGT    CTTCCACCCG
4641    CTTGTTGACT    TCTCTCAGAT    CCTGGACAGG    CCTATAATCA
4681    TTAGTCCCCG    GTTTCTTAAC    GGGTAGCAGG    GGCGTGTTCC
4721    AGGGGGACTG    GCAGGGTACC    AGAATTCCCT    GATCCAGCAG
4761    TCTCTGTATG    TGGGGCTTGA    TCCCAGTCT    GGCTTCTTGT
4801    GACATGGGGT    ATTGTTTTAT    GGACACGGGG    GTAGAGGTTG
4841    CCTTCAGAGG    TATGATCAGA    GGAGCTTGGC    GAACGGCCAG
4881    CCCCATGCCC    CCGGTTTCTG    CCCAGGCCTG    GGGAAAATCA
4921    GAGAGCCATG    TGGACCCTAG    AGGCACATCT    GGCCCTTTTG
4961    AGGTCTCATG    TAGCCGATAC    TCATCTTCTA    TGTTTAGGGT
5001    CAGCACTTGC    AGGGGCTGTC    CCATTGGTCC    CACAACCTGA
5041    GCTCCTGATC    CCTCAAAGTG    AATTTGGGCT    TTTAGTTTAG
5081    TCAGCAAATC    TCTTCCTAGC    AGAGGATAGG    GGCAATCTGG
```

FIG. 3D

```
              |   10        |   20        |   30        |   40
5121    TACATGGAGG   AAAGAATGGG   TGACCTTACC   GGTGGCTAGG
5161    TGCACTCGGC   GATCCGTGGT   CCAGCGATAC   CGCTTCCCTC
5201    CAGTAGCCCC   TTGGACCCAG   GCAGACTTGT   CACTTAGGGG
5241    TCCAGGATTT   TGGGTCAGCA   CGGAGTGTTG   GGCCCCAGTA
5281    TCCACTAGGA   AGGTGACGGG   TTGCCCCCG    ACTCTGAGGG
5321    TTATCCTGGG   TTCAGGGGGG   GGCTCCTGAC   CCTGACCTCC
5361    CTAATCGTCT   AAGGTCAGGA   GGGAGGCCTG   GGGTCGTGGT
5401    CCCCGGGGTC   CTCTTGGCTT   CTTGGGGCAA   TCTCTAGCCC
5441    AATGTCCCTT   TTCTTTGCAG   TAGGCACACT   GGTCGTGGTC
5481    GAGTTGGGGC   CTCCTTCGCT   CTCCTCCCTG   TCTATCCTGT
5521    CTCTGCCCGC   TAACGACAGT   AGCCAGCAAC   TTACTCATTT
5561    CTCTATGTCT   TCTGCGGTCC   CTCTCCTTCT   CTCTCTGCAC
5601    ATCCTCTGCC   CTACGGCGTT   CTTCCTTTTC   CTCTGTTTCT
5641    CTCCTAATAC   GTTCCTCTCT   TTCTTCCGGG   GTTTCTCGTT
5681    TATTAAAGAT   CTTTTCAGCT   TCCCTCACTA   AGTCTCCTAA
5721    GGTCTTACTC   TTCAAATCTT   CTAACCGCTC   TAACTTTCGC
5761    CCGATATCCG   GGGCGGACTG   CCAGATGAAT   GACATGGCCA
5801    CATTGGTTTC   TTGCCCTGGG   TCCTCAGGGT   CATAAGGAGT
5841    GTATCTGCGA   TAGGCCTCCT   TGAGTCTCTC   TAAAAAGGCT
5881    GAGGGAGACT   CATTAGGTCC   CTGGGTTATC   CCTTTTACCT
5921    TGGCCAAATT   GGTGGGGCTT   CTGCCCGCGT   TTTGGAGACC
5961    CGCTAGGAGC   AACTGGCGAT   AGTGGACTAG   GTGGTTCCTA
6001    CCTCGTTGGG   TGTTGTAGTC   CCAGTCGGGA   CGTTCCAAGG
6041    GAAAAGCATC   ATTAATGTCA   TTGGGCAGCT   GAGTTGGGCG
6081    TCCGTCCTCC   CCTCGAACCG   CCTTTCGGGC   CTCTAGGAGC
6121    ACTCGCTGTT   TTTCTTCTCC   CGTCAGCAGG   GTCCCTAATA
6161    GCTGTTGGCA   GTCATCCCAA   GTGGGCTGAT   GAGTAAGGAG
6201    AACGGACTCG   ATCAAAGCTG   TCAATTTAGC   TGGGTCCTCG
6241    GAGAAAGAGG   GGTTGTTATT   TTTCCAGTTA   TAGAGGTCAG
6281    AGGAGGAAAA   TGGCCAGTAT   TGATACTGTC   CATTCCCTCC
6321    CAGGCGAAGG   GGGAACGCCT   GAGAGGTAGT   AGAATCCGCC
6361    ACGGGGGGTT   CTTTTCTTCC   CCGCAGGCGG   GATACCATTG
6401    GGGAAGGGTC   AGGGGCTCCT   TCTGTAGGGG   CCACTTCTCC
6441    GCTATCGCCG   TTCCCGTCAG   GAGAGGGTGG   CCCTGGGTCC
6481    CGGTAAGGCG   GAGGGTCCTC   CGTGAGTAGA   TCAATGAGTG
6521    GTCCTCCGCT   ATCAGGAAGG   ACTTGAGGCC   TAGGTTTGGT
6561    GTTTAAAGGA   GAAGTGAGAG   CCGGATAGAG   GGAGGACTGG
6601    GGCGGGGTCG   AGAGTGGGGG   TTCAGGTGGG   AGAGAGGGGG
6641    CTGAAGGGGG   AAGAGAGAGG   GGAGGTTTAG   GGTGCACGAA
6681    GGGTCTGACC   CAGGGAGGGG   GGTCTACTGC   TATAGCTTCC
6721    CAGGTCACGA   TGTAGGGGAC   CTGATCCGGA   TGTCCATGTG
6761    GGCCAGGTGA   GAAGACCTTG   ATCTTAACCT   GTGTAATAAT
6801    GTCTGGGTTA   AAAGTGCCGT   CTCGTGGCCA   TCCGACGTTG
6841    AAGGTTGGCC   ATTCTGCAGA   GCAGAATGTA   ACCCAGCGCC
```

FIG. 3E

```
          |       10  |       20  |       30  |       40
6881    TTTTTCTAAC   CTCTACCGAC   AGGTTGTGGG   CTGTCCGTTC
6921    GACATCCTTC   CAGTGGTCTA   AAGTCAAACT   TAAGGGGGTG
6961    GTAACAGCCT   GGCCCATGTT   TTCAGACAAA   TACAGAAAAA
7001    CAGTCAAACA   GAGACAACAC   AGAACGATGC   TGCAGCAGAC
7041    AAGACGCGCG   GCGCGGCTTC   GGTTCCAAAC   CGAAAGCAAA
7081    AACTCAGACG   GGGGCGGAAA   CCGTTTTAGC   CCTCTGTCTC
7121    CTACCAGAAC   CACATACCCC   TCCTCTAAGG   GGGGTGCACC
7161    AAAGAGTCCA   AAACGATCGG   GATGGTTGGA   CTCTGGCCGG
7201    GCCACAAAAA   TGGCCCCCGA   AGTCCCTGGG   ACGTCTCCCA
7241    GGGTTGCGGC   CGGGTGTCTC   GAACTCGTCA   GTTCCACCAC
7281    GGATCCGCCA   GATACCAATC   TAGTCGGCCA   ACTAGTACAG
7321    ACACAGGCGC   ATAAAATCAA   TCAAAGACAC   AGGACAATGG
7361    ACAGACACAG   AACAATTGCT   GGCCAGCTTA   CCTCCCGGTG
7401    GTGGGTCGGT   GGTCCCTGGG   CAGGGTCTC   CAGATCCCGG
7441    ACGAGCCCCC   AAATGAAAGA   CCCCCGAGAC   GGGTAGTCAA
7481    TCACTCTGAG   GAGACCCTCC   CAAGGAACAG   CGAGACCACG
7521    AGTCGGATGC   AACAGCAAGA   GGATTTATTG   GATACACGGG
7561    TACCCGGGCG   ACTCAGTCTA   TCGGAGGACT   GGCGCGCCGA
7601    GTGAGGGGTT   GTGAGCTCTT   TTATAGAGCT   CGGGAAGCAG
7641    AAGCGCGCGA   ACAGAAGCGA   GAAGCAGGCT   GATTGGTTAA
7681    TTCAAATAAG   GCACAGGGTC   ATTTCAGGTC   CTTGGGGGAG
7721    CCTGGAAACA   TCTGATGGGT   CTTAAGAAAC   TGCTGAGGGT
7761    TGGGCCATAT   CTGGGGACCA   TCTGTTCTTG   GCCCCGGGCC
7801    GGGGCCGAAC   CGCGGTGACC   ATCTGTTCTT   GGCCCCGGGC
7841    CGGGGCCGAA   ACTGCTCACC   GCAGATATCC   TGTTTGGCCC
7881    AACGTTAGCT   GTTTTCGTGT   ACCCGCCCTT   GATCTGAACT
7921    TCTCTATTCT   TGGTTTGGTA   TTTTTCCATG   CCTTGCAAAA
7961    TGGCGTTACT   GCGGCTATCA   GGCTAAatca   gatctgccgg
8001    tctccctata   gtgagtcgta   ttaatttcga   taagccaggt
8041    taacctgcat   taatgaatcg   gccaacgcgc   ggggagaggc
8081    ggtttgcgta   ttgggcgctc   ttccgcttcc   tcgctcactg
8121    actcgctgcg   ctcggtcgtt   cggctgcggc   gagcggtatc
8161    agctcactca   aaggcggtaa   tacggttatc   cacagaatca
8201    ggggataacg   caggaaagaa   catgtgagca   aaaggccagc
8241    aaaaggccag   gaaccgtaaa   aaggccgcgt   tgctggcgtt
8281    tttccatagg   ctccgccccc   ctgacgagca   tcacaaaaat
8321    cgacgctcaa   gtcagaggtg   gcgaaacccg   acaggactat
8361    aaagatacca   ggcgtttccc   cctggaagct   ccctcgtgcg
8401    ctctcctgtt   ccgaccctgc   cgcttaccgg   atacctgtcc
8441    gcctttctcc   cttcgggaag   cgtggcgctt   tctcaatgct
8481    cacgctgtag   gtatctcagt   tcggtgtagg   tcgttcgctc
8521    caagctgggc   tgtgtgcacg   aaccccccgt   tcagcccgac
8561    cgctgcgcct   tatccggtaa   ctatcgtctt   gagtccaacc
8601    cggtaagaca   cgacttatcg   ccactggcag   cagccactgg
```

FIG. 3F

```
              |   10         |   20         |   30         |   40
 8641   taacaggatt   agcagagcga   ggtatgtagg   cggtgctaca
 8681   gagttcttga   agtggtggcc   taactacggc   tacactagaa
 8721   ggacagtatt   tggtatctgc   gctctgctga   agccagttac
 8761   cttcggaaaa   agagttggta   gctcttgatc   cggcaaacaa
 8801   accaccgctg   gtagcggtgg   ttttttttgtt  tgcaagcagc
 8841   agattacgcg   cagaaaaaaa   ggatctcaag   aagatccttt
 8881   gatcttttct   acggggtctg   acgctcagtg   gaacgaaaac
 8921   tcacgttaag   ggattttggt   catgagatta   tcaaaaagga
 8961   tcttcaccta   gatcctttta   aattaaaaat   gaagttttaa
 9001   atcaatctaa   agtatatatg   agtaaacttg   gtctgacagt
 9041   taccaatgct   taatcagtga   ggcacctatc   tcagcgatct
 9081   gtctatttcg   ttcatccata   gttgcctgac   tccccgtcgt
 9121   gtagataact   acgatacggg   agggcttacc   atctggcccc
 9161   agtgctgcaa   tgataccgcg   agacccacgc   tcaccggctc
 9201   cagatttatc   agcaataaac   cagccagccg   gaagggccga
 9241   gcgcagaagt   ggtcctgcaa   ctttatccgc   ctccatccag
 9281   tctattaatt   gttgccggga   agctagagta   agtagttcgc
 9321   cagttaatag   tttgcgcaac   gttgttgcca   ttgctacagg
 9361   catcgtggtg   tcacgctcgt   cgtttggtat   ggcttcattc
 9401   agctccggtt   cccaacgatc   aaggcgagtt   acatgatccc
 9441   ccatgttgtg   caaaaaagcg   gttagctcct   tcggtcctcc
 9481   gatcgttgtc   agaagtaagt   tggccgcagt   gttatcactc
 9521   atggttatgg   cagcactgca   taattctctt   actgtcatgc
 9561   catccgtaag   atgcttttct   gtgactggtg   agtactcaac
 9601   caagtcattc   tgagaatagt   gtatgcggcg   accgagttgc
 9641   tcttgcccgg   cgtcaatacg   ggataatacc   gcgccacata
 9681   gcagaacttt   aaaagtgctc   atcattggaa   aacgttcttc
 9721   ggggcgaaaa   ctctcaagga   tcttaccgct   gttgagatcc
 9761   agttcgatgt   aacccactcg   tgcacccaac   tgatcttcag
 9801   catcttttac   tttcaccagc   gtttctgggt   gagcaaaaac
 9841   aggaaggcaa   aatgccgcaa   aaaagggaat   aagggcgaca
 9881   cggaaatgtt   gaatactcat   actcttcctt   tttcaatatt
 9921   attgaagcat   ttatcagggt   tattgtctca   tgagcggata
 9961   catatttgaa   tgtatttaga   aaaataaaca   aataggggtt
10001   ccgcgcacat   ttccccgaaa   agtgccacct   gacgtctaag
10041   aaaccattat   tatcatgaca   ttaacctata   aaaataggcg
10081   tatcacgagg   ccctttcgtc   tcgcgcgttt   cggtgatgac
10121   ggtgaaaacc   tctgacacat   gcagctcccg   gagacggtca
10161   cagcttgtct   gtaagcggat   gccgggagca   gacaagcccg
10201   tcagggcgcg   tcagcgggtg   ttggcgggtg   tcggggctgg
10241   cttaactatg   cggcatcaga   gcagattgta   ctgagagtgc
10281   accatatgga   catattgtcg   ttagaacgcg   gctacaatta
10321   atacataacc   ttatgtatca   tacacatacg   atttaggtga
10361   cactata   (SEQ ID NO: 9)
```

```
         |   10         |   20         |   30         |   40
  1    MACSTLPKSP    KDKIDPRDLL    IPLILFLSLK    GARSAAPGSS
 41    PHQVYNITWE    VTNGDRETVW    AISGNHPLWT    WWPVLTPDLC
 81    MLALSGPPHW    GLEYQAPYSS    PPGPPCCSGS    SGSSAGCSRD
121    CDEPLTSLTP    RCNTAWNRLK    LDQVTHKSSE    GFYVCPGSHR
161    PREAKSCGGP    DSFYCASWGC    ETTGRVYWKP    SSSWDYITVD
201    NNLTTSQAVQ    VCKDNKWCNP    LAIQFTNAGK    QVTSWTTGHY
241    WGLRLYVSGR    DPGLTFGIRL    RYQNLGPRVP    IGPNPVLADQ
281    LSLPRPNPLP    KPAKSPPASN    STPTLISPSP    TPTQPPPAGA
321    SZZ (SEQ ID NO: 10)
```

FIG. 3G

```
         |   10         |   20         |   30         |   40
  1    AAPGSSPHQV    YNITWEVTNG    DRETVWAISG    NHPLWTWWPV
 41    LTPDLCMLAL    SGPPHWGLEY    QAPYSSPPGP    PCCSGSSGSS
 81    AGCSRDCDEP    LTSLTPRCNT    AWNRLKLDQV    THKSSEGFYV
121    CPGSHRPREA    KSCGGPDSFY    CASWGCETTG    RVYWKPSSSW
161    DYITVDNNLT    TSQAVQVCKD    NKWCNPLAIQ    FTNAGKQVTS
201    WTTGHYWGLR    LYVSGRDPGL    TFGIRLRYQN    LGPRVPIGPN
241    PVLADQLSLP    RPNPLPKPAK    SPPASNSTPT    LISPSPTPTQ
281    PPPAGASZZ (SEQ ID NO: 11)
```

Structure of MuLV/HIV chimeric glycoproteins

CELLS        SUPERNATANTS

1. CRA-3
2. C108G
3. G3-4
4. chimp serum
5. MAb 273 (αgp70)
6. goat αgp70 serum

FUSION GLYCOPROTEINS

This application is a continuation-in-part of U.S. application Ser. No. 07/938,100, filed Aug. 28, 1992, now abandoned, which application is incorporated by reference herein.

BACKGROUND OF THE INVENTION

It has been shown for retroviral, influenza, and herpes viral glycoproteins that removal of N-linked glycans dramatically reduces immune reactivity (Alexander and Elder, 1984, Science, 226:1328–1330; Sjobloom et al., 1987, J. Gen. Virol. 68:549–554; Olofsson et al., 1990, J. Virol. 71:889–895). Considerable evidence has also accumulated suggesting that N-linked glycosylation is necessary for proper immunoreactivity or immunogenicity of human immuno-deficiency virus (HIV) gp120. For example, an extensive study comparing the immunogenicity of native glycosylated gp120 to that of env 2-3, a nonglycosylated form of the protein produced in yeast, was performed in baboons (Haigwood et al, 1992, J. Virol. 66:172–182). In this study, glycosylated gp120 induced high titers of neutralizing antibodies against the homologous and related viruses, and weak neutralizing titers against more distant viruses, while the nonglycosylated protein yielded only low neutralizing titers directed solely against the homologous virus. In addition, whereas the glycosylated protein was able to bind to CD4, the nonglycosylated protein was not. Other studies have shown that removal of N-linked glycans from native or recombinant gp120 reduces or abolishes binding activity of gp120 to CD4 and diminishes infectivity of HIV-1 (Matthews et al, 1987, PNAS 84:5424–5428; Fenouillet et al, 1989, J. Exp. Med. 169:807–821; Fenouillet et al, 1990, J. Virol. 64:2841–2848). Recent data show that removal of specific carbohydrates from recombinant gp160 reduced both its immunoreactivity with hyperimmune antisera and its immunogenicity in rabbits (Benjouad et al, 1992, J. Virol. 66:2473–2483). Finally, the epitopes of strongly neutralizing MAbs that have been isolated are destroyed by removal of N-linked glycans from the viral proteins (Fung et al, 1992, J. Virol. 66:848–856). These results demonstrate an important role for N-linked glycans in gp120 immunoreactivity and immunogenicity. These glycans may be acting either indirectly, by achieving the correct conformation of gp120, or directly by determining the formation of immunoreactive or immunogenic sites.

A major difficulty in the production of isolated gp120 domains is the fact that all of these domains are highly glycosylated. Considerable evidence suggests that glycans are needed either to achieve correct conformations or for the formation of the epitopes themselves.

The invention described here is intended to address this problem, but can also be used for the expression of non-gp120 glycopeptides whose immunogenicities or biological activities are dependent on correct glycosylation or conformation.

SUMMARY OF THE INVENTION

The present invention relates to vectors for expressing a glycosylated protein in cells, wherein the vector is adapted to express a fusion glycoprotein. The fusion glycoprotein contains an N-terminal fragment of env surface protein of a retrovirus, the surface protein containing a hydrophobic glycosylation signal located about seven residues N-terminal to a Cys-trp-leu-cys sequence (SEQ ID NO: 18) located approximately centrally in the surface protein. The N-terminal fragment includes the N-terminal globular domain of the env surface protein. A selected glycopeptide is fused to the C-terminus of that N-terminal fragment. The selected glycopeptide preferably includes a domain that is glycosylation dependent, a domain that is conformationally dependent, or both. The domain may contain, for example, an immunoreactive or immunogenic epitope, or have another biological activity, such as receptor binding or hormone binding activity.

Also included in the invention are plasmids that encode the above vectors. These plasmids can be used to engineer and express the vectors.

Mammalian cell cultures that produce the novel fusion glycoproteins, the novel fusion glycoproteins, and viral particles incorporating those glycoproteins in their envelope moieties are also included in the invention.

BRIEF DESCRIPTION OF THE DRAWINGS

FIG. 1 shows the DNA and amino acid sequence (SEQ. ID. NO: 8) of the FB29 isolate of Friend ecotropic MuLV.

FIG. 3A shows the DNA sequence of pLRB332 (SEQ ID NO: 9). MuLV sequences (non-coding strand) are shown in upper case; non-MuLV sequences are shown in lower case. The NheI site and stop codons at 864, the first codon of gp70 at 1719, and the env initiation codon at 1821, are underlined.

FIG. 3B shows the amino acid sequence (SEQ. ID NOS: 10–11) of amino acid 1–285 truncation fragment of gp70 expressed by pLRB332. The terminal ASZZ is the amino acid sequence encoded by the NheI site and two stop codons. The top sequence (SEQ ID NO: 10) includes the signal peptide, and the bottom sequence (SEQ ID NO. 11) does not.

FIG. 4B shows a diagram of truncation and insertion fusion glycoproteins described in the examples.

DETAILED DESCRIPTION OF THE INVENTION

Figure 2:
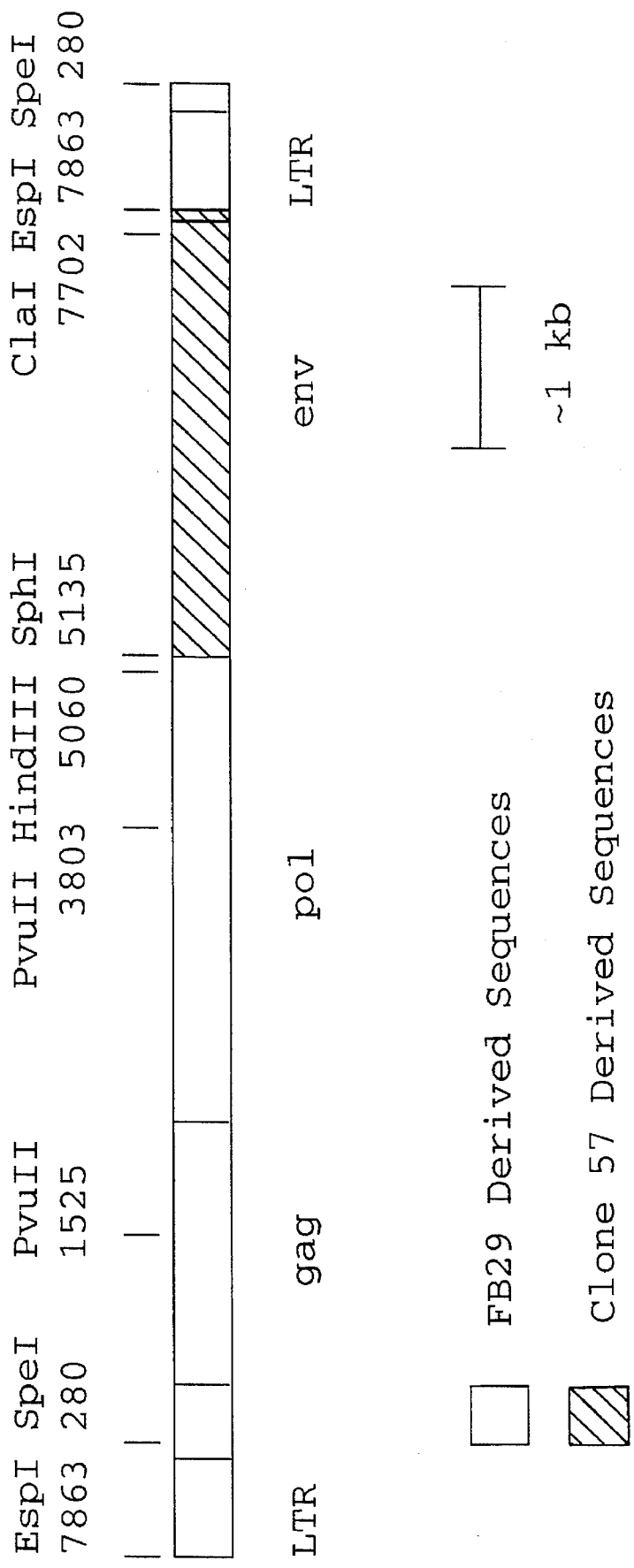
FIG. 2 shows a restriction map of a FB29/clone 57 hybrid.

The env-based expression system of this invention allows glycopeptides and viral particles incorporating those glycopeptides to be made by mammalian cells in an efficient manner. We have determined that expressed glycopeptides retain glycosylation dependent (such as N-glycan dependent) and conformationally dependent structures. Such expression is particularly important for viral glycopeptides to make them useful for immunoreactive purposes, such as immunoassays or affinity purifications, or for immunogenic purposes, such as the production of monoclonal antibodies or for inducing protective immunity.

It will normally be most desirable to use the invention to express a glycopeptide that corresponds to (i.e., has an amino acid sequence that is the same as, or is derived from, the sequence of) a naturally occurring glycopeptide. We have found that the env expression system of the invention is useful, for example, in efficiently expressing N-glycan dependent epitopes contained in the V2 region of HIV-1 gp120. As described in U.S. application Ser. No. 07/860,889, incorporated by reference herein, the V2 region is recognized by a powerfully neutralizing antibody against an N-glycan dependent epitope. In particular, the antibodies are capable of neutralizing HIV-1 infection at a concentration lower than that of previously described neutralizing antibodies. An example of such an antibody, a monoclonal antibody derived from peripheral mononuclear B-cells of an HIV-immunized chimpanzee, is produced by EBV transformed chimp peripheral blood mononuclear cells deposited at the ATCC, Parklawn Drive, Rockville, Md. on Mar. 10, 1992, and accorded accession no. CRL 10983. New glycopeptides that include the V2 region of gp120 are made according to the invention. They contain an N-glycan-dependent epitope that is reactive with antibodies against N-glycan dependent epitopes of native gp120 but do not contain the immunodominant V3 region. Thus they are especially useful to induce (or measure in an immunoassay) a specific anti-V2 response. Such immunoreactive V2 glycopeptides have not been expressed by others.

The vector of the invention is advantageously used to efficiently express complex conformational epitopes, i.e., those involving several disulfide bonds. For example, we have correctly expressed the V1/V2 region of gp120, perhaps the most complicated portion of that molecule, which in addition to six glycosylation sites, includes six cysteines, all of which are believed to be involved in specific disulfide bonds (Leonard et al., 1990, J. Biol. Chem. 265:10373–10382). The V1/V2 region expressed using the vector has the capability of reacting with antibodies against N-glycosylation dependent epitopes (as described above) and/or with antibodies against conformational epitopes of that region.

This invention allows for the expression of fragments of glycoproteins, or glycopeptides, in such a way as to maximize their synthesis, glycosylation, folding, stability, and secretion. Expression of the fusion glycoprotein on the surface of cells or virus particles is also accomplished. The invention can also provide a "tag" for the detection and purification of glycopeptides that is independent of their own properties. The expression system can also advantageously be used to express glycopeptides in immunogenic form, for example fused to the N-terminal carrier portion of the env surface protein. Thus, the vectors are particularly useful in the expression of glycopeptides containing glycan-dependent or conformationally dependent epitopes, fused to the N-terminal surface protein fragment. If desired, the vector may be used to express a fusion protein as a secreted molecule. Alternatively, sequences can be included in the vector that code for the remaining C-terminal part of the env gene. We have determined that fusion proteins can then be functionally expressed in the envelope of infectious or non-infectious particles of the particular retroviral env used in this invention. In this application, "truncation chimeric (or fusion) glycoprotein" is used to refer to those glycoproteins that are expressed by vectors which do not include sequences coding for the remaining env glycoprotein (in particular the C-terminal globular domain of these env surface protein and the trans-membrane protein.). The term "insertion chimeric (or fusion) glycoprotein" is used wherein foreign protein fragments are inserted into the region of the surface protein of these particular env types that links the N-terminal and C-terminal globular domains without loss of sequences of either globular domain, and including the transmembrane protein.

The N-terminal fragment of the surface protein used is a carrier for the glycopeptide or glycoprotein that is to be expressed. Retroviral env is normally expressed as a membrane-associated precursor protein which is processed during transport through the ER (endoplasmic reticulum) and Golgi system by proteolytic cleavage and glycan maturation to form a complex consisting of SU (surface protein), disulfide-linked to the TM (transmembrane) protein. For example, MuLV (surface protein) gp70 is a soluble glycoprotein containing several domains, and is linked to transmembrane protein p15E. (Although the molecular weights vary somewhat, the term "gp70" is used herein to refer to the surface protein of all MuLV virus strains, as well as the highly similar surface protein of the FeLV (Feline Leukemia virus) strains.) The receptor binding domain of gp70 is comprised of the N-terminal region, which is believed to be a structurally independent globular region. This domain contains at least two N-linked glycans. The secondary structure of an ecotropic gp70 has recently been determined, and shows that the twelve cysteines in this region are joined in six internal disulfide bonds. The C-terminal domain of MuLV surface protein is also a globular region that contains 4–5 N-linked glycans and includes the disulfide linkage to p15E.

To make a vector for expressing fusion glycoprotein, a recombinant gene is constructed in which the coding sequence for a selected glycopeptide is fused in frame to the C-terminus of a truncation fragment of the retroviral env surface protein. This fragment codes for the N-terminal domain of the protein that is glycosylated normally and folds into a globular structure. In one embodiment of the invention, the globular structure includes the receptor binding domain of the surface protein, i.e., the domain that binds to its cell surface receptor. In another embodiment of the invention, the globular domain includes the first twelve cysteines of gp70, which are all believed to be involved in intra-domain disulfide bonding.

In a preferred embodiment, the truncation (or insertion) site is selected to be in a region of env surface protein that is believed to be in an extended conformation and to function as a linker between the two globular domains of the surface protein. This region is known to be immunogenic in the FeLV and MuLV viruses. For example, in Friend clone 57 of MuLV, this linker region of gp70 is believed to maximally extend from the Cys-free sequence from residue 185 up to but not including the conserved N-glycan attachment site at residue 302. In other surface proteins, the linker is believed to maximally include the entire cysteine free sequence immediately N-terminal to the conserved N-linked glycosylation site homologous to the conserved N-linked glycosylation site at residue 302 of Friend clone 57 gp70.

In another preferred embodiment of the invention, sequences coding for the C-terminal domain of the surface protein and for the trans-membrane domain of the env precursor glycoprotein are added at the C-terminus of the fusion protein. These additional sequence can generate membrane bound fusion proteins that are efficiently expressed at the cell surface and on virus particles. The additional sequences can allow expression of the fusion glycoprotein from infectious virus. Coexpression of at least the gag gene from any vector allows incorporation into retroviral particles. This can be advantageous, because, for example, particulate immunogens are believed to generally be more immunogenic than their soluble counterparts.

A particular class of retroviral env proteins that share a specific sequence motif defines those env proteins that are used in the fusion glycoproteins, and coded for by the vectors, of this invention. In particular, the retrovital env proteins are defined by the presence of a hydrophobic glycosylation signal located about seven residues N-terminal to a Cys-trp-leu-cys sequence (SEQ ID NO: 18) located centrally in the SU domain of the env polyprotein. This glycosylation signal and sequence have been described by Kayman et al., 1991, J. Virol. 65:5323. These sequences are invariably associated with the presence of a Cys-x-x-x-x-x-x-cys-cys sequence (SEQ ID NO: 19) within the ectodomain of the transmembrane protein. Preferred are those env proteins of this type that also display an extensive Cys-free region N-terminal to the hydrophobic glycosylation signal. This cys-free region preferably is at least 40 amino acids long. These include env proteins of the REV-A avian virus (Wilhelmsen, Eggleton and Temin 1984 J. Virol. 52:172–182) and Mason-Pfizer Monkey Virus (Sonigo et al.1986 Cell 45:375–385). More preferred are those in which this Cys-free region is Pro-rich, i.e., contains several Pro residues. This includes the SU of Gibbon Ape Leukemia Virus (Delassus, Sonigo and Wain-Hobson 1989 Virol. 173:205–213). Most preferred for use in this invention are the env genes of MuLV and of Feline Leukemia Virus (e.g. Donahue et al.1988 J. Virol. 62:722–731), which have a very high degree of sequence similarity to each other and also share the above mentioned defining characteristics. These surface proteins have N-terminal and C-terminal globular domains joined by a linker region into which the selected peptide is placed to form a truncation or an insertion glycoprotein.

The sequences encoding the fusion glycoprotein (whether as a secretable separate moiety, an internal protein, a cell surface protein, or associated with retrovital particles) can be expressed using conventional vectors for expression of proteins in mammalian cells. Retroviral expression vectors can be used, such as those developed from Rous sarcoma virus (Sorge et al., 1982, J. Mol. Appl. Gen., 1:547), murine mammary tumor virus (Gunzberg et al., 1986, Virology, 155:236) and murine leukemia virus (MuLV), such as the Moloney MuLV (McLachlin et al., 1990, in Progress in Nucleic Acid Research and Molecular Biology, 38:91) or the Friend MuLV. Secreted fusion glycoproteins or glycoproteins associated with viral particles are produced from a preferred retroviral vector described below. The preferred vector allows easy and rapid manipulation of new constructs, and high level expression.

Alternatively, conventional non-retroviral viral vectors can be conventionally constructed to express the fusion glycoproteins of the invention, including vaccinia (for example, see Vijaya et al., 1988, Vaccines 88, CSH pp.211–214) and herpes virus (for example, see Kit et al., 1991, Vaccine 9:564–572).

In addition to viral vectors, conventional plasmid vector expression systems that do not employ viral particle intermediates can be employed to express the fusion glycoproteins of the invention in mammalian cells. These systems are either transient expression systems (i.e., those that result in death of the mammalian cells producing the expressed product) or those that allow stable producing mammalian cell lines to be established (i.e., do not result in death of the cells).

The systems described above are known in the art and are made using well-established techniques. Conventional cloning vehicles are used to make plasmids encoding the desired vectors using techniques such as described in Current Protocols in Molecular Biology (Ausubel et al. eds, John Wiley and Sons, NY, N.Y.) and Molecular Cloning: A Laboratory Manual (Sambrook et al. eds, Second Edition, 1989, Cold Spring Harbor Laboratory Press, Cold Spring Harbor, N.Y.). Conventional cell lines, such as mammalian insect, yeast and other glycosylating cell lines, are transformed, transfected, or infected, to generate the fusion glycoproteins of the invention. Cells are also transformed, transfected, or infected in vivo to generate the fusion glycoproteins.

The vectors used in any of these systems for expressing the fusion glycoprotein, i.e. that include a sequence coding for the fusion glycoprotein of the invention operably linked to a promotor, are included in the invention.

The invention also includes the process of infecting mammalian cells with viral vectors, or transfecting the cells with plasmid vectors, of the invention. Mammalian cell lines may be infected when it is desired to purify the fusion glycoprotein for use in an immunoreactive or immunogenic composition. Producer cell lines are made to express secreted fusion glycoprotein or fusion glycoproteins associated with viral particles. It may be preferable to express the fusion glycoprotein in viral particles rather than in soluble form to make recovery easier. Also, infectious or non-infectious particles incorporating the desired glycoprotein in their envelope can be obtained in this manner for immunizing mammals.

Alternately, the vectors can be used to infect or transfect mammalian or other glycosylating cells .in vivo in order to cause expression of the soluble glycoprotein, or glycoprotein expressed on the cell surface, or associated with viral particles.

Fusion glycoproteins can be conventionally purified from lysates or supernatants of producing mammalian cell cultures. Soluble glycoproteins are advantageously purified using monoclonal or polyclonal antibodies against the surface protein. If desired, the selected glycopeptide can be cleaved from the env fragment by including a conventional cleavable linker between the N-terminal globular domain and the inserted glycopeptide. If the selected glycopeptide is recovered on a retroviral particle, a cleavable linker can also be included between the selected glycopeptide and the C-terminal env region. The term "fusion glycoprotein," as used herein, refers to products wherein the env sequence is directly fused to the selected glycopeptide as well as wherein there is an additional sequence or sequences in the fusion product. The product may contain the cleavable linker referred to above, and/or other sequences.

For example, a cleavage site for a specific protease could be inserted between the surface protein fragment(s) and the selected glycopeptide in order to allow eventual release of the selected glycopeptide from the env sequence. Incorporation of an Ile-glu-gly-arg sequence (SEQ ID NO: 20) allows specific cleavage with blood coagulation factor Xa and has been used successfully to separate (i.e., cleave) domains of interest from carrier domains in recombinant fusion proteins (Nagai and Thogersen, 1987, Meth. Enzym. 153:461–481).

Also a non-immunological affinity tag can be included at the N-terminus of the surface protein fragment. For example, addition of a sequence of six histidine residues allows rapid purification on an $Ni^{2+}$-nitrilotriacetic affinity column under native conditions using imidazole buffers (Janknecht et al., 1991, PNAS 88:8972–8976 and Examples below).

T-helper epitopes from the source of the heterologous gene fragment being expressed can also be inserted into the fusion gene at the N-terminus, the C-terminus, or elsewhere, to enhance the immunogenicity of the fusion protein and the probability of a rapid and intense immune response of animals immunized with fusion glycoprotein, following exposure to the pathogen. For purposes of HIV-1 glycopeptide expression, a number of T-helper epitopes with broad MHC reactivity have been characterized, such as amino acids 791–823 from the C-terminus of gp41 or amino acids 391–414 from the C4 region of gp120 (Berzofsky et al, 1991, J. Clin. Invest. 88:876–884).

For expressing certain HIV sequences in fusion glycoproteins of this invention, it may be necessary to include RRE (rev responsive element) sequences in the vector such that they will be retained in the mRNA encoding the fusion glycoprotein and to provide rev activity in cells expressing the fusion glycoprotein. These elements are not required for expressing the V1/V2, V3, or V4/C4 fusion glycoproteins described herein.

It is also possible to express multiple selected glycopeptides in a single fusion glycoprotein. This can be done with either truncation or insertion glycoproteins. For example, the selected glycopeptides can be different fragments of a single protein, fragments from different proteins, or homologous fragments from different alleles of the same protein (e.g. the V1/V2 domain of gp120 from the HXB2d and MN isolates of HIV-1), or any combination of such fragments. The multiple inserts can be placed at different locations within the interdomain linker of an SU. Alternatively, multiple selected glycopeptides can be inserted in concatenated arrays at a single site in the SU. Such inserted multiple glycopeptides can be separated from each other by a spacer peptide.

The N-terminal fragment of the env glycoprotein preferably forms a receptor binding domain, as it is believed that proper autonomous folding and glycosylation of that region during expression may aid independent proper folding and glycosylation of the selected glycopeptide. It may also aid in efficient secretion of the fusion glycoprotein. Examples of such env fragments are amino acids 1–263 and 1–285 of Friend ecotropic clone 57 gp70. An env fragment containing amino acids 1–227 is also described below. These gp70 fragments terminate in or near a proline-rich region that is believed to form an extended linker between N-terminal and C-terminal globular domains of gp70 and is known to be an immunogenic region of gp70. The region carries epitopes recognized by polyclonal hyperimmune sera and monoclonal antibodies. The gp70 domain can therefore serve as a tag for the identification and purification of the fusion glycoprotein. Truncation at amino acid 227 removes the entire proline-rich linker region and some of the previously assigned N-terminal domain but retains all of the N-terminal Cys residues and results in a fragment that possesses receptor-binding activity. Truncation at amino acid 263 retains a large fraction of the proline-rich linker but eliminates the section of this linker region that is known to carry O-linked glycans in gp70 as well as the third N-linked glycan of Friend MuLV gp70. The resultant protein fragment is efficiently expressed and secreted more rapidly than the 227 amino acid fragment. Truncation at amino acid 285 retains the entire proline-rich linker region, including the O-linked glycosylation sites and the additional N-linked glycosylation site, and the resultant fragment is also efficiently expressed and secreted. The optimal truncation site in gp70 may depend on the particular glycopeptide being expressed.

The expression vector of the invention should encode a signal sequence 5' to the surface protein sequence. In the examples below, the native env signal sequence is encoded in the vectors but other signal sequences can be substituted.

It has been determined that if the C-terminal portion of the env gene sequence is also incorporated in the vectors, i.e., where a foreign sequence is inserted into the surface protein between the N-terminal globular domain and the C-terminal domain, many resulting hybrid env proteins are processed, incorporated into cellular membranes and viral particles, and retain the ability to mediate virus infection. Foreign sequences are exposed on intact virions in an area that is highly immunogenic. Inserted sequences can be used to obtain an infectious particle, a non-infectious particle, or an env protein that is processed and expressed at the cell surface, but not incorporated into virus particle.

The processing of a retroviral env product begin with the folding of the glycosylated precursor protein in the endoplasmic reticulum and culminate with the mature SU and TM proteins on the surface of the virus particle. Those proteins mediate binding to the host cell and effect membrane fusion between the viral and host cell membranes, delivering the viral core into the cytoplasm. Insertion chimeric glycoproteins such as those described in the examples below are able to act as SU for infectious virus. Such fully functional chimeric glycoproteins are believed to be more versatile than non-functional glycoproteins. Particular insertion chimeric glycoproteins may be blocked at different stages of this processing or blocked in one or more functions. However, insertion chimeric glycoproteins that do not retain full function are also useful.

An insertion chimeric glycoprotein that is synthesized but that does not fold properly into a compact globular structure with native env disulfide bonds would be expected to be retained in the endoplasmic reticulum until it was degraded intracellularly. Such an insertion chimeric glycoprotein might not be useful for production of purified glycopeptides or as an immunogen for induction of humoral responses, but would likely be most useful for induction of MHC class I-mediated cellular immune responses. For example, it may be desirable to avoid competition between induction of humoral and cellular immune response, as has been suggested for tuberculosis and AIDS. In this case, use of expression vectors encoding insertion chimeric glycoproteins that do not fold and are not transported out of the endoplasmic reticulum would be particularly appropriate. Vectors encoding insertion chimeric glycoproteins that are processed from the endoplasmic reticulum to the Golgi apparatus but do not continue to the cell surface would be useful in the same ways.

Insertion chimeric glycoproteins that are processed to the cell surface are capable of eliciting humoral responses as well as cellular responses. An insertion chimeric glycoprotein that is destabilized in its interaction with the transmembrane protein is rapidly released from the cell surface (i.e. it is functionally similar to a secreted protein). An insertion chimeric glycoprotein that interacts normally with the transmembrane protein is likely to be present at significant levels on the cell surface. An insertion chimeric glycoprotein that is present on the cell surface would normally be more immunogenic than one that is rapidly released.

Insertion chimeric glycoproteins that are incorporated into viral particles present the selected glycopeptide on a multivalent particulate immunogen. This is a particularly potent method of antigen presentation. It also allows for particle based purification methods for the insertion chimeric glycoprotein and the selected glycopeptide. Such insertion chimeric glycoproteins do not need to be capable of mediating viral infection.

To obtain expression of chimeric glycoproteins that cannot mediate viral infection, pseudotyped retroviral vectors, other viral vectors (see above) or direct DNA transfection can be used. Any insertion chimeric glycoprotein that is processed to the cell surface can be obtained as a purified protein, and used for its desired purpose, e.g., whether used for binding to a receptor, for immunoreacting, or for inducing an immune response. Non-functional insertion chimeric glycoproteins that are incorporated into viral particles can also be used as inactivated particles for the desired purpose.

The fully functional insertion chimeric glycoprotein can be encoded in an infectious retroviral vector, i.e., a retrovirus that causes a spreading infection of retrovirus expressing the insertion glycoprotein. In the appropriate host such a retrovirus establishes viremia in the infected animal, thereby exposing the animal to an increasing dose of the selected glycopeptide of the insertion glycoprotein for an extended time. Infectious retrovirus incorporating the insertion glycoprotein in its envelope can also be expressed in a species that the virus cannot infect. For example, human cells can be transformed or transfected with a vector for expressing infectious ecotropic MuLV that contains the insertion glycoprotein in its envelope. Since ecotropic viruses do not infect humans, this method is equivalent to using a defective virus. In that case, particle associated, cell surface, and soluble forms of the insertion glycoprotein are presented for (if immunogenicity is desired) induction of humoral responses, and intracellular expression for cellular immune response. Alternatively, deletion of substantial parts of the pol gene from the expression vector genome leads to the expression of non-infectious virus particles bearing the insertion glycoprotein, regardless of host. In addition, incorporating the recombinant env gene into the expression vector genome in the absence of the gag gene allows processing to the cell surface, but not particle formation. Also, expressing the surface protein domain of the chimeric env without the transmembrane domain produces a secreted insertion chimeric glycoprotein.

Chimeric surface proteins that function in virus replication can be used to generate hyperimmune sera and MAbs using live virus instead of adjuvants. Chimeric surface proteins that are incorporated into virus particles but are defective for viral replication can also be used. The inoculated animal is exposed to a multivalent, particulate immunogen rather than a soluble protein, which is potent way of presenting many antigens. Preparation of virus for inoculating animals such as mice and rats to prepare MAbs is extremely easy and inexpensive compared with use of purified proteins. Non-infectious, pseudotyped virus particles can be used in any animals, including humans, and are inexpensive and easy to produce. MuLVs, in particular, have a wide host range that allows use of live virus inoculations in a wide range of mammals. Examples described below utilize an ecotropic SU, which allows infection of rats and mice. Use of amphotropic SUs allows retroviral infection of other mammals as well, including humans. Dualtropic and xenotropic SUs allow infection of certain mammals as well. These SUs are well characterized and known to those skilled in the art.

Where fusion glycoproteins are incorporated into viral particles, the size of the particle can be used as a basis for the purification of the fusion glycoprotein and the selected glycopeptide. Because of this particle association, separation from almost all other proteins found in cell supernatants is easily accomplished by ultracentrifugation of the particles.

An inserted protein that is expressed in infectious or non-infectious particles can be used in inactivated particle compositions used, for example, for immunogenic purposes. The infectious or non-infectious particles can also be expressed by inoculating with retrovirus vectors, or with other vectors such as those mentioned above. In the case of immunogenic compositions, preparation of live virus is easier and less expensive than preparation of subunit compositions. Inactivated virus particles are also relatively inexpensive and easy to produce, and often highly immunogenic. It is also possible to purify viral particles of the invention to a higher yield and purity than certain viruses from which the inserted glycoprotein can be derived, e.g., HIV. With respect to HIV, this is due in part to the fact that the surface protein in the present invention is covalently linked to the transmembrane protein whereas in HIV that linkage is non-covalent. Also, nonhazardous particles can be obtained using the invention, whereas HIV is highly pathogenic and therefore difficult to obtain in large quantities. Also, by using multiple allelic antigenic sequences of a virus from which the inserted polypeptide is derived, a broader (i.e., less type-specific) anti-virus response might be induced than by using the virus itself as an immunogen.

DNA compositions such as plasmid DNA vectors can also be used for inoculation. An example of such a vector is described below. Retroviral vectors can also be used in DNA compositions as well as in viral particles.

Expression of the chimeric env gene without the gag gene would produce proteins expressed on the cell surface. The gag gene can be co-expressed with the chimeric env gene in the absence of a functional pol gene to produce defective retroviral particles which present the chimetic retroviral particles on their surface. Such use retains the advantage of cell surface and/or particle presentation of humoral response epitopes and presentation of cellular response epitopes while avoiding potential risks of live retrovirus infection.

The expression vector of the invention can be created from available materials using a shuttle vector for manipulating constructs in, e.g., E. coli. Assembly of expression vectors is described in detail in the Examples below. Alternatively, expression vector pLRB332, described in the Examples, can be obtained and is adapted for insertion of a sequence encoding a selected glycopeptide to make an expression vector encoding a fusion product.

Vectors described in the Examples below have a number of advantages:

1) All DNA construction steps can be carried out in bacteria. If desired, resulting plasmids can be used directly to construct mammalian cell lines expressing a recombinant fusion glycoprotein without the need to generate recombinant viruses within infected cells, as is required for other common systems such as vaccinia virus, herpes virus, and baculovirus. This allows large numbers of constructs to be prepared and analyzed quickly and efficiently.
2) The vector system is non-lytic and thus generates stable cell lines, so that continuously producing cultures can be isolated and used to produce fusion glycoproteins.
3) Cultures in which essentially all cells are expressing the recombinant protein can be prepared quickly, without using selectable markers, by using retroviral vector packaging cell lines.

4) The constructs can be easily expressed in a wide variety of cells, including those of human origin, using amphotropic pseudotypes of the MuLV vector, or by constructing the chimeras in an amphotropic surface protein.

5) The level of expressed protein in mammalian cell culture is quite high, allowing analyses to be carried out easily and quickly during the experimental stages of vaccine development, as shown in the Examples below.

The MuLV vector embodiment of the invention can be manufactured in packaging cell lines such as those that are described in the Examples or any other suitable lines. Such cell lines are well known and available. The producer cell line used, i.e., that which is infected and produces the fusion glycoprotein, can be a conventional mammalian cell line that can be infected with either ecotropic or amphotropic MuLVs. Ecotropic retroviruses infect and replicate only in mouse and rat cells. Amphotropic retroviruses infect mouse as well as other mammalian species. The MuLV virus can also be used to infect mammals to cause in vivo expression of the fusion glycoprotein.

As noted above, the purified products of the expression system can be used as immunogens, either for production of monoclonal or polyclonal antibodies or induction of protective immunity. The products can be mixed with appropriate adjuvants in order to enhance imune response. If the selected glycopeptide is cleaved from the carrier (or the entire envelope, where expressed in particle form), it can be chemically joined to a conventional carrier, such as bovine serum albumen. The fusion glycoprotein, however, when used separately from virus particle as an immunogen, preferably has a molecular weight greater than 20,000 daltons, so that it is likely to be immunogenic by itself. Immunogenic compositions can be administered intradermally or subcutaneously or orally. For a vaccine, several inoculations are preferably administered, with follow-up booster administrations.

Conventional assays can be performed with products made using the invention to detect antibodies, receptors, or other binding partners for the expressed glycopeptide. Truncation and insertion chimeric glycoproteins, as well as glycopeptides cleaved from these glycoproteins, are used in these methods. Lower levels of mature insertion chimeric glycoprotein are obtained as compared with truncation chimeric glycoprotein; thus it may be preferable to use the truncation chimeric glycoprotein. A selected insertion chimeric glycoprotein, however, may present epitopes not presented by the corresponding truncation chimeric glycoprotein. The ability to use particle association as the basis for insertion chimeric glycoprotein purification can also make these preferable to truncation glycoproteins. If desired, the insertion chimeric glycoproteins can be separated from the particle and the other vital proteins.

An immunoassay such as an ELISA might employ a soluble fusion product including, for example, the V1/V2 glycopeptide, and also include means for the detection of an immune complex formed between anti-HIV antibody and the fusion product. For example, a "sandwich" might be formed using a solid phase coated with HIV-1 lysate, anti-HIV antibody, and the fusion product, followed by detection of the "sandwich" by a labelled anti-gp70 antibody. Alternatively, a solid phase might be coated with the fusion glycoprotein (or glycopeptide cleaved from the glycoprotein), the solid phase exposed to sera containing anti-HIV antibody, and the presence of the anti-V1/V2 antibody detected with a subsequent labelled anti-human antibody. In another method, radiolabelled fusion glycoprotein is used as a substrate for immunoprecipitation, followed by separation of proteins according to molecular mass on SDS polyacrylamide gels and detection by exposure to photographic film. This is a sensitive method, but it is more labor intensive than ELISA methods. Fusion glycoproteins can also be used in Western Blot methods. Alternatively, a receptor ligand expressed according to the invention can be used in a assay for the receptor. Other diagnostic uses for various expressed glycoproteins made using the invention will be apparent to one skilled in the art.

As noted above, the expression vector is preferably used to express short glycopeptides, for example, less than 150 amino acids, most preferably shorter than 100 amino acids. Often the glycopeptide expressed will be greater than 20 amino acids, embodiments of the examples being greater than 40 amino acids. The invention, however, may also be used for expressing larger fragments or even complete glycoproteins.

Fragments of any of the glycopeptides described herein can also be advantageously expressed as fusion products of the invention.

The invention is further illustrated by the following examples.

EXAMPLES

CONSTRUCTION OF GLYCOPEPTIDE EXPRESSION FUSION VECTORS

Standard recombinant DNA techniques are used throughout, as can be found in manuals such as Current Protocols in Molecular Biology (Ausubel et al.eds, John Wiley and Sons, NY, N.Y.) and Molecular Cloning: A Laboratory Manual (Sambrook et al. eds, Second Edition, 1989, Cold Spring Harbor Laboratory Press, Cold Spring Harbor, N.Y.). All relevant work was done using the E. coli Strain DH5Alpha (BRL) [Bethesda Research Labs] and the Hanahan (Hanahan, 1983, J. Mol. Biol. 166:557–580) method was used for transformation. Enzymes were from Boehringer-Mannheim and New England Biolabs and were used as recommended by the manufacturers; agarose was from BRL and FMC Bioproducts. All references cited either in the Examples section or in the rest of this application are hereby incorporated by reference.

The MuLV retroviral vector described below has a typical retroviral vector structure, except that gag and pol expression have not been eliminated. Not eliminating gag and pol expression may be desirable for some purposes. The vector uses the natural splice donor and acceptor sequences involved in normal expression of MuLV env in the expression of the fusion glycoprotein.

A one LTR clone of the FB29 isolate of Friend ecotropic MuLV permuted at the unique HindIII site (5060) (Sitbon et al. Cell 47:851, 1986) was used to make a MuLV expression vector. The sequence of this isolate is shown as FIG. 1 (SEQ ID NO: 8). Restriction site numbering below refers to the first base of the enzyme recognition site in this FB29 sequence, which begins at the 5'end of the genomic RNA. The entire envelope gene sequence and a portion of the pol gene and the 3' LTR from the clone 57 Friend ecotropic MuLV (Oliff et al. J. Virol. 33:475, 1980; complete sequence shown in Koch., Nunsmann and Friedrich, 1983, J. Virol. 45:1–9) were substituted for those of the FB29 isolate using the shared, unique restriction sites SphI (5135) and EspI (7863), resulting in an FB29/clone 57 hybrid permuted viral genome. A collinear, two LTR clone was constructed from this isolate as follows.

The unique PvuII site in pSP72 (Promega), a high copy number E. coli vector, was converted to an NheI site by insertion of an 8-basepair linker (GGCTAGCC). The EspI (7863) to HindIII (5060) fragment carrying the LTR and the gag gene and part of the pol gene from the FB29 permuted clone was then inserted into HindIII/EcoRV cut plasmid, following E. coli DNA polymerase Klenow fragment-filling of the EspI overhang. Then the HindIII (5060) to SpeI (280) (SpeI generates NheI compatible overhangs) fragment from the permuted FB29/clone 57 hybrid clone carrying the rest of the pol gene and the envelope gene and the LTR was inserted into NheI/HindIII cut plasmid. This resulted in a hybrid colinear viral genome, with the 5' LTR beginning at the (destroyed) EspI site and the 3' LTR terminating at the (destroyed) SpeI site, in which all sequences derive from the FB29 clone except those between the SphI and EspI sites. The total plasmid, pLRB303, is 11.32 kb, with unique viral sequences of 8.93 kb (a restriction map of the MuLV sequences is shown in FIG. 2).

Figure 4A:
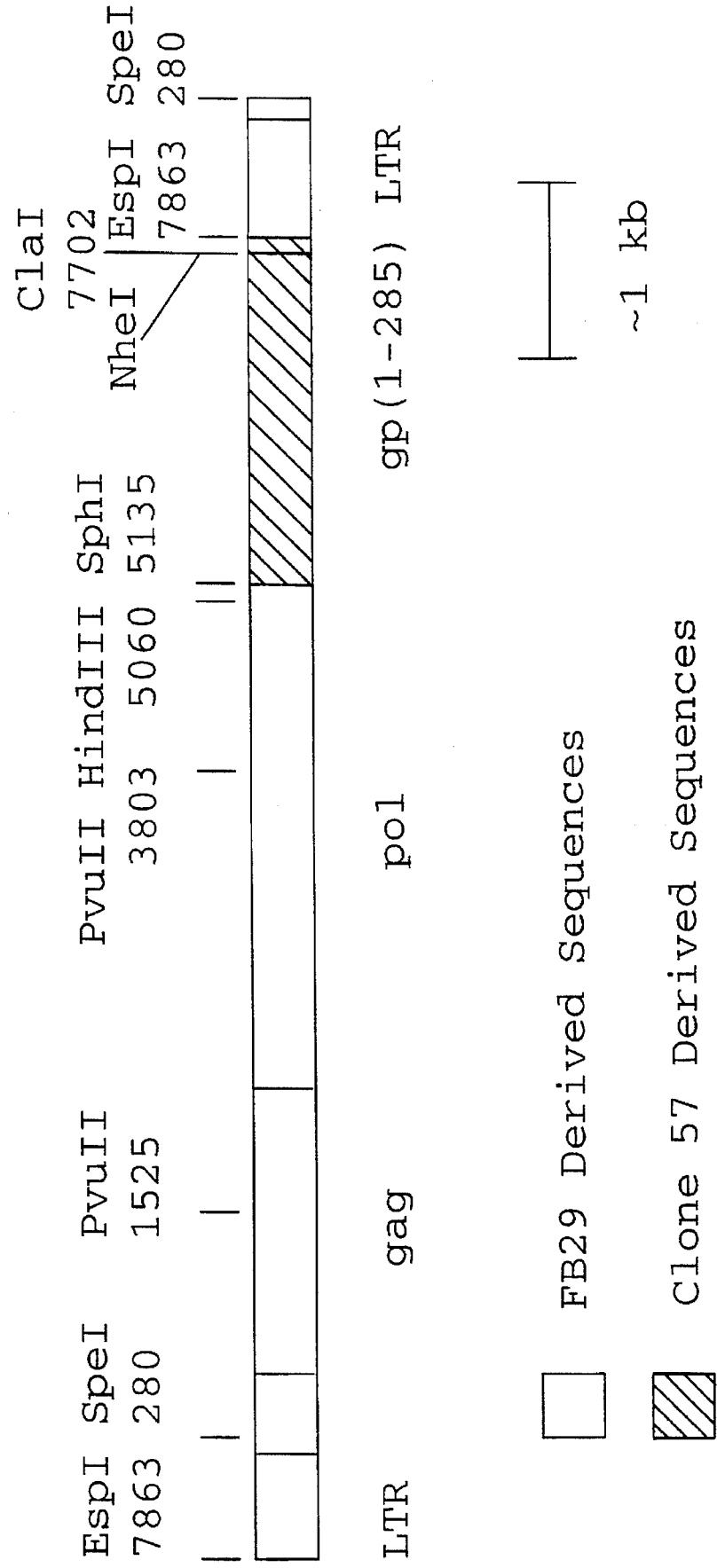
FIG. 4A shows a restriction map of the MuLV regions of pLRB332.

Glycopeptide expression fusion vectors were derived from pLRB303 as follows. Clone 57 sequences containing the SphI site near the 5' end and modified at the 3' end were generated by polymeras chain reaction (PCR). In these modified sequences, the selected fusion sites in the hypervariable region of gp70 are followed by an in-frame NheI site that adds an ala-ser dipeptide to the end of the gp70 fragment, two stop codons (UAA-UGA), and a ClaI site. The 5' primer was 5'-CCAAGAAGCTTCTAGAAGAAA-3'(SEQ ID NO: 3) the 3'primer for the gp(1–263) construct was 5'-GGTTATCGATTCATTAGCTAGCGGGGGGA-GACTTGGCAGGTT-3' (SEQ ID NO: 3) and the 3' primer for the gp(1–285) construct was 5'-CTCAGCCCCCGCCAGCAGGAGCTAGCTAATGAA-TCGATAACC-3'(SEQ ID NO: 1). PCR was carried out using Vent® polymerase (New England Biolabs) in supplied Vent® buffer plus 4 mM MgSO$_4$ and the recommended BSA with 0.5 microM primers, 400 microM each dNTP, 100 ng of pLRB140 (a HindIII (5063) to KpnI (8323) fragment of clone 57 in plasmid pTZ18R (US BIOCHEMICALS) containing the 3' end of the pol gene, all of the env gene, and most of the 3' LTR) in a Perkin Elmer Cetus DNA Thermal Cycler 9810 for 25 cycles of 96° for 1.5 min, 52° for 1.5 min, 72° for 1.5 min. Polymerase was added last to reaction mixtures that were pre-incubated and held at 96°. Following extraction with phenol:chloroform and ethanol precipitation, PCR products were digested with SphI and ClaI and the desired SphI/ClaI fragments purified from agarose gels with Qiaex® Resin (Qiagen) according to the manufacturer's directions. These fragments were then inserted into pLRB303 that had been digested with SphI and ClaI and gel purified. This resulted in the deletion of viral envelope sequences between the desired fusion point and the ClaI (7702) site present near the 3' end of the envelope gene. The gp(1–263) fusion vector was designated pLRB333; the gp(1–285) fusion vector was designated pLRB332. FIG. 3A shows the complete DNA sequence of pLRB332 (SEQ ID NO: 9), and FIG. 3B shows the amino acid sequence (SEQ ID NOS:10–11) of the encoded truncation fragment. FIG. 4A is a restriction map of the MuLV sequences of pLRB332. The NheI and ClaI sites are used for the insertion of sequences coding for the glycopeptide that is to be expressed. The structures of these plasmids were confirmed using NdeI, BamHI, SphI/NheI, SphI/ClaI, and NheI/ClaI restriction digests.

pLRB332 (SEQ ID NO: 9) was deposited at the ATCC, Parklawn Drive, Rockville, Md. on Aug. 25, 1992 and assigned accession no. 69057. pLRB332 can be converted to the sequence of pLRB333 (i.e., encoding gp(1–263)) by taking a PCR-generated SphI/ClaI fragment made from pLRB332 (SEQ ID NO: 19) using the primers described for construction of pLRB333 and substituting this fragment for the SphI/ClaI fragment carried by pLRB332 (SEQ ID NO: 9).

CONSTRUCTION OF GENES EXPRESSING TRUNCATION FUSION GLYCOPROTEINS

For insertion of gene fragments into pLRB332 (SEQ ID NO: 9) or pLRB333, PCR is used to generate DNA fragments containing an in-frame restriction site for NheI (results in an ala-ser linker between the gp70 fragment and the inserted glycopeptide) 5' to the sequence encoding the glycopeptide to be expressed and following this sequence two in-frame stop codons followed by a ClaI restriction site. If the desired gene fragment contains an NheI site, an AvrII site (results in an arg-arg linker) or SpeI site (results in an thr-ser linker) or XbaI site (results in an ser-arg linker), each of which result in NheI compatible ends, can be used instead; if the desired gene fragment contains a ClaI site, a BstBI or AccI site could be substituted. These restriction sites are used to insert the gene fragment into the expression vector, generating a gene that can express the fusion glycoprotein. A NarI or other appropriate restriction site (i.e., one not present in pLRB332 (SEQ ID NO: 9) or pLRB333 or the gene fragment to be expressed and, if possible, coding for amino acids such as ala, gly, pro, ser, or thr, that are unlikely to constrain the conformation taken by the fusion glycoproteins) can be included between the gene fragment and the stop codons to allow the subsequent insertion of additional sequences at the 3' end of the fusion protein.

If all of the restriction enzymes having either NheI or ClaI compatible overhangs have at least one recognition site in the desired sequence, a new fusion vector can be generated using restriction sites for insertion that are not present in the gene fragment of interest. One can also mutate undesired restriction sites in the sequences coding for selected glycopeptides to facilitate construction. Alternatively, one can use DNA fragments from partial digests for constructions.

For construction of genes to express fusion glycoproteins containing the V1/V2 domain of HIV-1 HXB2d (amino acids 86–179 of the mature gp120) NheI and ClaI sites were used. The 5' primer was 5'-CATCGCTAGCCTAAAGCCATGTGTAAAATTA-3' (SEQ ID NO: 4) and the 3' primer was 5'-ACTGATCGATTCATTAGGATACCTTTGGACAGG-CC-3'(SEQ ID NO: 5). The DNA substrate was 100 ng of HXB2-env (Page et al, 1990, J. Virol. 64:5270–5276) but any other source of HXB2d envelope sequences is equivalent. PCR conditions were as described above for generation of pLRB332 (SEQ ID NO: 9) and pLRB333 except for using dNTPs at 200 micron. NheI/ClaI digested PCR-generated fragments were gel purified and ligated to pLRB332 (SEQ ID NO: 9) and pLRB333 that had been NheI/ClaI digested and gel purified, generating pLRB335 and pLRB336, respectively. The structures of these plasmids were confirmed with NdeI, NheI/ClaI, and NsiI/NdeI restriction digests.

For construction of genes to express fusion glycoproteins containing the V3 domain of HIV-1 HXB2d (amino acids 261–306) NheI and ClaI sites were used and a NarI site was included between the HIV sequences and the stop codon, adding gly-ala to the C-terminus of the fusion protein. The 5' primer was 5'-CGGTGCTAGCTCTGTAGAAATTAATTGT-3'(SEQ ID NO:6) and the 3' primer was 5'-CTAGATCGATCTATTAGGCGCCTGCTCTACTAAT-GTTACA-3'(SEQ ID NO: 7). Other components and conditions were as described above for the V1/V2 constructions except that MgSO₄ was not added. Insertion of PCR-generated fragments into expression vectors was as described for V1/V2 constructions. The gp(1–263)-V3 construct was designated pLRB350 (this construct has also been referred to as pLRB346). The gp(1–285)-V3 construct was designated pLRB349. Plasmid structures were characterized with NdeI, AseI, and NheI/XbaI restriction digests. The ClaI sites were not characterized because in these constructs there is C residue 3' to the ClaI site, resulting in Dam methylation that blocks cleavage by ClaI.

Figure 4B:
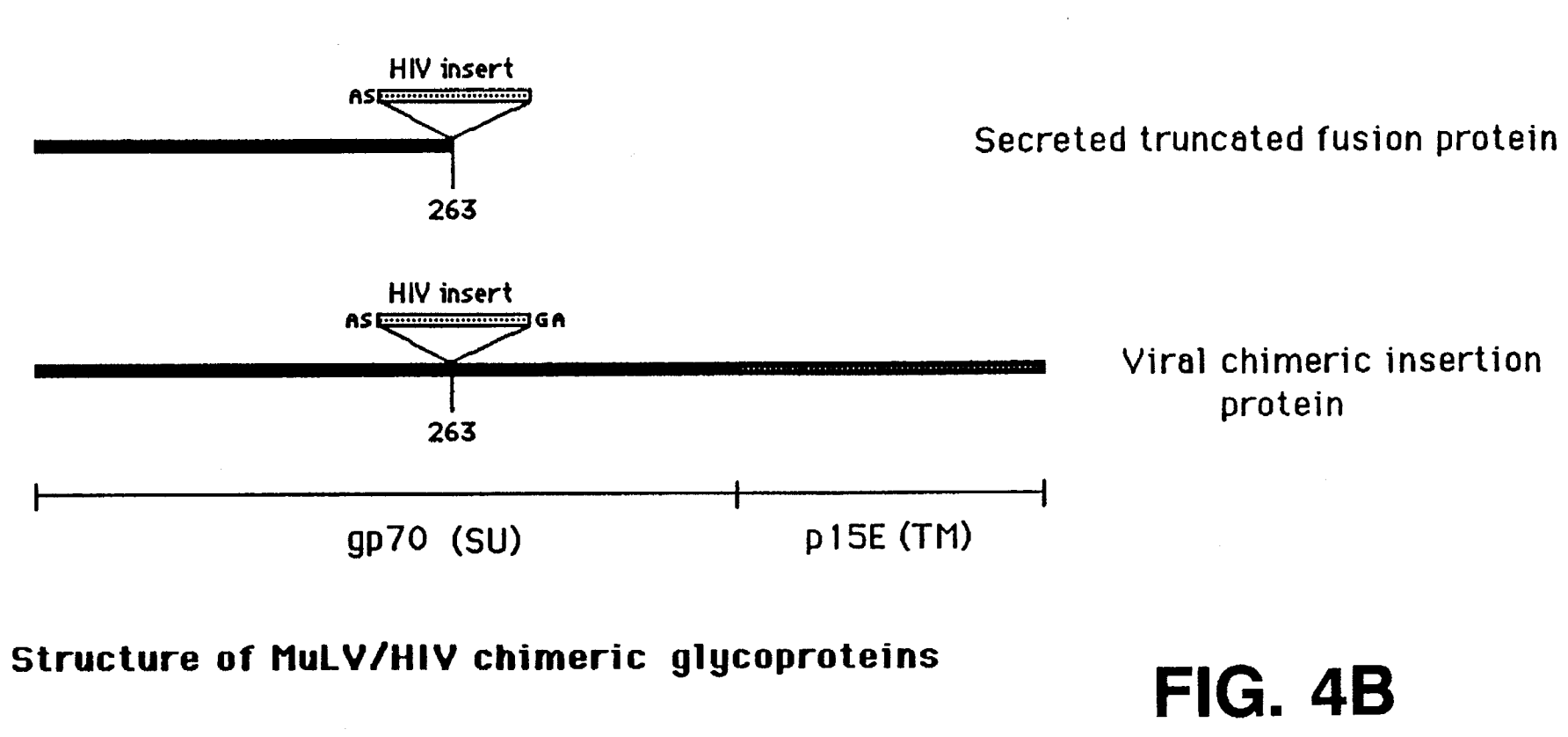

The produced truncation fusion glycoprotein is diagrammed in FIG. 4B.

CONSTRUCTION OF GENES EXPRESSING INSERTION FUSION GLYCOPROTEINS

Two sites within the inter-domain spacer sequence of gp70 were used above as fusion points for soluble chimeric proteins (i.e., insertion sites for heterologous protein fragments). pLRB349 and pLRB350 contain genes for truncation chimeric glycoproteins with insertions of the HXB2 V3 loop sequence following residues 285 and 263 respectively. The insertions were made to include a NarI site adjacent to and in frame with the C-terminal sequence of the truncation fusion proteins. This unique NarI site was then used to replace the missing env gene sequences between the truncation point and the ClaI site near the 3' end of the env gene. The necessary env gene sequences beginning with a NarI site were generated by PCR from pLRB303. The 5' primer for the fragment beginning with residue 263 was 5'-TCCT GGC GCC TCT AAT TCG ACT CCC ACA TT-3'(SEQ ID NO: 12); the 5' primer for the fragment beginning with residue 286 was 5'-TTGC GGC GCC ACG GGA GAC AGG TTA CTA AAT C-3'(SEQ ID NO: 12); the 3' primer for both fragments was 5'-ACTG TCT AGAAAG CGC GCG AAC AGA AGC GAG AAG C-3'(SEQ ID NO: 17). Genes for truncation chimeric fusion glycoproteins containing a selected glycopeptide other than V3 can be converted to insertion chimeras (containing the complete env protein) by the same process used to generate the V3 insertion chimeras provided they contain a NarI or other suitable site at the 3' end of the inserted gene fragment. Alternatively, other heterologous sequences can be incorporated into the V3 insertion chimeras directly by removal of the V3 gene fragment using the NheI and NarI sites and replacing it with the appropriate NheI-NarI bounded gene fragment generated by PCR or otherwise. Using these methods with NheI and NarI sites, the complete insert consists of Ala-Ser-Heterologous Sequence-Gly-Ala.

To generate an insertion chimeric glycoprotein virus plasmid one can also begin with pLRB332 (SEQ ID NO: 9). If a 263/264 insertion is desired, pLRB332 is first modified as described above for the generation of pLRB333. Next, a truncation chimeric glycoprotein plasmid is constructed that incorporates a NarI site at the 3'end of the inserted gene fragment, as described above for the construction of the V3 truncation chimeric glycoprotein genes in pLRB349 and pLRB350. Finally, the truncation chimeric glycoprotein gene is converted to an insertion chimeric glycoprotein gene as described in the preceding paragraph. Using this method, any source of the clone 57 env gene that includes the 3' LTR, in which the designated 3' primer is located, can serve as substrate. A shorter clone that includes the necessary sequences of the env gene, e.g. without unnecessary LTR sequences, can also be used as a source of the C-terminal env sequences by using a different 3' primer.

EXPRESSION OF TRUNCATION FUSION GLYCOPROTEIN VECTORS

Standard cell culture and retrovirological methods were used (see, e.g. Kayman et al, 1991, J. Virol. 65:5323 and references cited therein for general methods and co-culture methods for expression of defective viral genomes).

Column-purified, or boiling mini-prep, glycopeptide fusion vector plasmid DNA (Qiagen or Nest Group kits) is transfected into the amphotropic packaging cell line PA317 (Miller and Buttimore, 1986, Mol. Cell. Biol. 6:2895) by conventional calcium phosphate methods using CellPhect reagents (Pharmacia) (or by Lipofectamine (BRL) transfection according to manufacturer's specifications) and then cells of the ecotropic packaging line psi2 (Mann et al, 1983, Cell 33:153) were added. Amphotropic pseudotypes of the glycopeptide fusion vector from PA317 cells infect psi2 cells and ecotropic pseudotypes from psi2 cells infect PA317 cells, allowing the fusion vector to spread through the culture, resulting in high level expression of the fusion protein in the culture, as well as production of high titers of pseudotyped fusion vector virus particles, usually within three-four days of establishing the co-culture. These co-cultures of PA317 and psi2 cells expressing the fusion glycoprotein can be used directly to characterize the biochemical and immunoreactive properties of the fusion protein. To eliminate the presence of helper virus envelope proteins, the pseudotyped vector virus from these cultures was used to infect NIH 3T3 cells and clonal infected cell lines generated by limiting dilution.

The produced insertion fusion glycoprotein is diagrammed in FIG. 4B.

EXPRESSION OF INSERTION FUSION GLYCOPROTEIN VECTORS

Functional insertion chimeric glycoproteins are expressed by transfection into 3T3 cells. For preparing pseudotypes of infectious chimeras, virus from these cells can be infected into appropriate packaging cell lines. For example, a virus coding for an ecotropic MuLV can be used to infect an amphotropic packaging cell line, such as the PA317 line. This produces pseudotyped virus that will infect, e.g. humans, but will not cause a spreading viremia, except in mice and rats. For non-functional insertion chimeric glycoproteins or for functional insertion chimeric glycoproteins expressed from retroviral vectors without either a functional gag or pol genes, expression is carried out in packaging cocultures as described for truncation chimeric glycoproteins.

GENERAL METHODS FOR ANALYSIS

Characterization of the fusion proteins was done by radioimmunoprecipitation assay (RIPA) and sodium dodecyl sulfate polyacrylamide gel electrophoresis (SDS-PAGE), methods for which are referenced in Kayman et al, 1991, J. Virol. 65:5323, and by ELISA as described herein.

V1/V2 domain synthetic peptides ADP 740.9 through ADP 740.17, which are each 20 amino acids long and offset by 10 amino acids and match HXB2 gp120 sequences from amino acids 82 through 181, were obtained. Additional V2 domain 16mer oligopeptides matching amino acids 135–149 of the HXB2d sequence (ADP 794.2) and the homologous sequences from MN (ADP 794.3) and RF (794.4), each containing an additional C-terminal Cys residue, were also obtained. The analogous peptide matching the consensus sequence for this region as defined in the Los Alamos Human Retroviruses and AIDS database, Ile-Arg-Asp-Lys-Val-Gln-Lys-Glu-Tyr-Ala-Leu-Phe-Tyr-Lys-Lev-(Cys) (ADP 794.1), (SEQ ID NO: 22) was also used. A linear V3 peptide corresponding to the complete sequence between the Cys residues defining the V3 loop of HXB2, Thr-Arg-Pro-Asn-Asn-Asn-Thr-Arg-Lys-Ser-Ile-Arg-Ile-Gln-Arg-Gly-Pro -Gly-Arg-Ala-Phe-Val-Thr-Ile-Gly-Lys-Ile-Gly-Asn-Met-Arg-Gln-Ala-His (SEQ ID NO: 23), was obtained. Peptide ADP 792.3 had the same sequence for the V3 loop and included the defining Cys residues and a C-terminal Asn. It was obtained as the "cyclic" form. An MN V3 peptide, ADP 715, Arg-Lys-Arg-Ile-His-Ile-Gly-Pro-Gly-Arg-Ala-Phe-Tyr-Thr-Thr-Lys-Asn (SEQ ID NO: 24), corresponded to the tip of the V3 loop.

To facilitate purification of the gp(1–263):V3$_{HXB2}$ fusion glycoprotein, His$^8$Gln$^9$ of gp70 were replaced with a sequence of six His residues. PCR overlap mutagenesis (Ho et al., 1989, Gene 77:51–599) was used to construct the appropriate SphI to NheI gene fragment for insertion into the expression vector. Supernatants from 3T3 cells expressing the His$_6$ form of gp(1–263):V3$_{HXB2}$ were dialyzed against PBS (pH 8), NaCl was added to 0.5M, and protein was bound to Ni$^{2+}$-nitrilotriacetate Sepharose (Qiagen) in this buffer. gp(1–263):V3$_{HXB2}$ was eluted with 30 mM imidazole in PBS (pH 7.4) following a 20 mM imidazole wash, and constituted only a small fraction of the Coomassie-staining material in these preparations. Comparison with bovine serum albumin standards yielded an estimate of 3 μg of partially purified gp(1–263):V3$_{HXB2}$ isolated per ml of culture supernatant.

ELISAs were performed in TiterTek Immuno-assay plates (Flow Laboratories). Antigens were adsorbed to wells for 60 min in 100 μl carbonate buffer (pH9.6) washed with PBS/0.05% Tween, blocked for 90 min with 2% BSA in PBS, and washed again with PBS/0.05% Tween. 100 μl of serum diluted in PBS was added for 60 min at RT, and wells were washed with PBS/0.05% Tween, incubated for 60 min with 100 μl alkaline phosphatase coupled goat anti-human IgG (Zymed) diluted in 2% BSA, washed in PBS/0.05% Tween, and 100 μl of 1 mg/ml p-nitrophenol phosphate in diethanolamine buffer (pH 9.8) was added. Absorbance at 405 nm was measured between 30 and 60 min after substrate addition. The amount of partially purified gp(1–263):V3$_{HXB2}$ used per assay was always sufficient to give at least 75% of the maximum achievable signal. Peptides were used at 100 ng per well; assays were insensitive to increased amounts of peptide. Background A$_{405}$ reaction in wells lacking antigen was subtracted from the data obtained.

Figure 5:
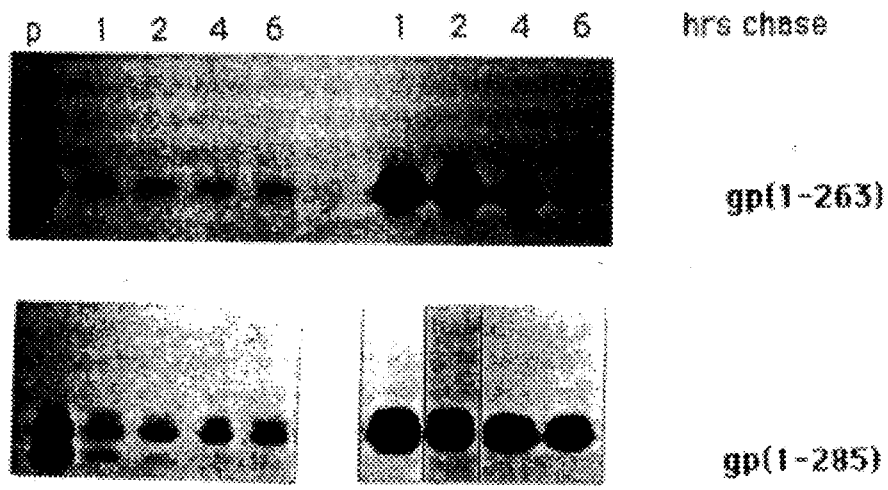
FIG. 5 shows autoradiograms of an SDS-PAGE analysis of immunoprecipitated gp(1–263) and gp(1–285) truncation glycoproteins described in the Examples.

ANALYSIS OF FUSION PRODUCTS a. Analysis of synthesis and secretion of the gp(1–263) and gp(1–285) truncated products 3T3 cells expressing either gp(1–263) (top) or gp(1–285) (bottom) were pulse labeled with 35 $^{35}$S-cysteine for 30 minutes (lanes p) and chased with unlabeled medium for 1, 2, 4 or 6 hrs. Cell lysates and supernatants were then immunoprecipitated with a polyclonal goat anti-gp70 serum (goat anti-Rauscher gp70, Microbiological Associates), and analyzed by SDS-PAGE. Results are shown in FIG. 5.

RESULTS

This experiment documents the efficient synthesis and secretion of both the gp(1–263) and gp(1–285) truncated gp70 products. For the gp(1–263) construct, at the end of the 30 minute pulse a single band of about 38 kD was seen in the cell extract. After the 1 hr chase, greater than 90% of this material was found in the supernatant medium with less than 10% left in the cells. After 2 hrs of chase, a similar level of protein was detected in the medium, while at longer periods the amount recovered starts decreasing, presumably indicating degradation.

Similar results were found for the gp(1–285) construct. In this case two bands were seen in the cell extracts, a major 43 kD band representing the precursor form, and a 48 kD band representing O-glycosylated product. After a 1 hr chase period, almost all of the labeled material had been secreted into the extracellular medium in the form of a major 48 kD band and a minor 50 kD band. The small amount of material left in the cells seems stable, and presumably represents a fraction of misfolded protein which cannot be fully processed and secreted.

b. Analysis of immunoreactivity of gp(1–263)-V1/V2 fusion product.

Figure 6B:
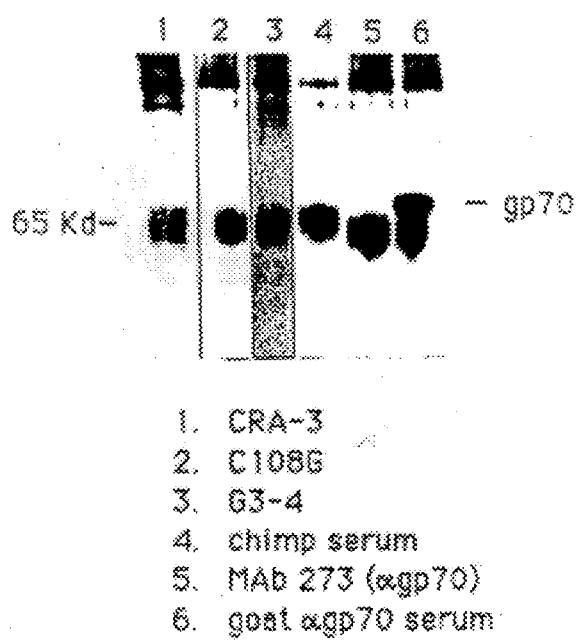
FIG. 6B shows an autoradiogram of an SDS PAGE analysis of immunoprecipitated gp(1–263) V1/V2 fusion glycoprotein described in the Examples.
Figure 6A:
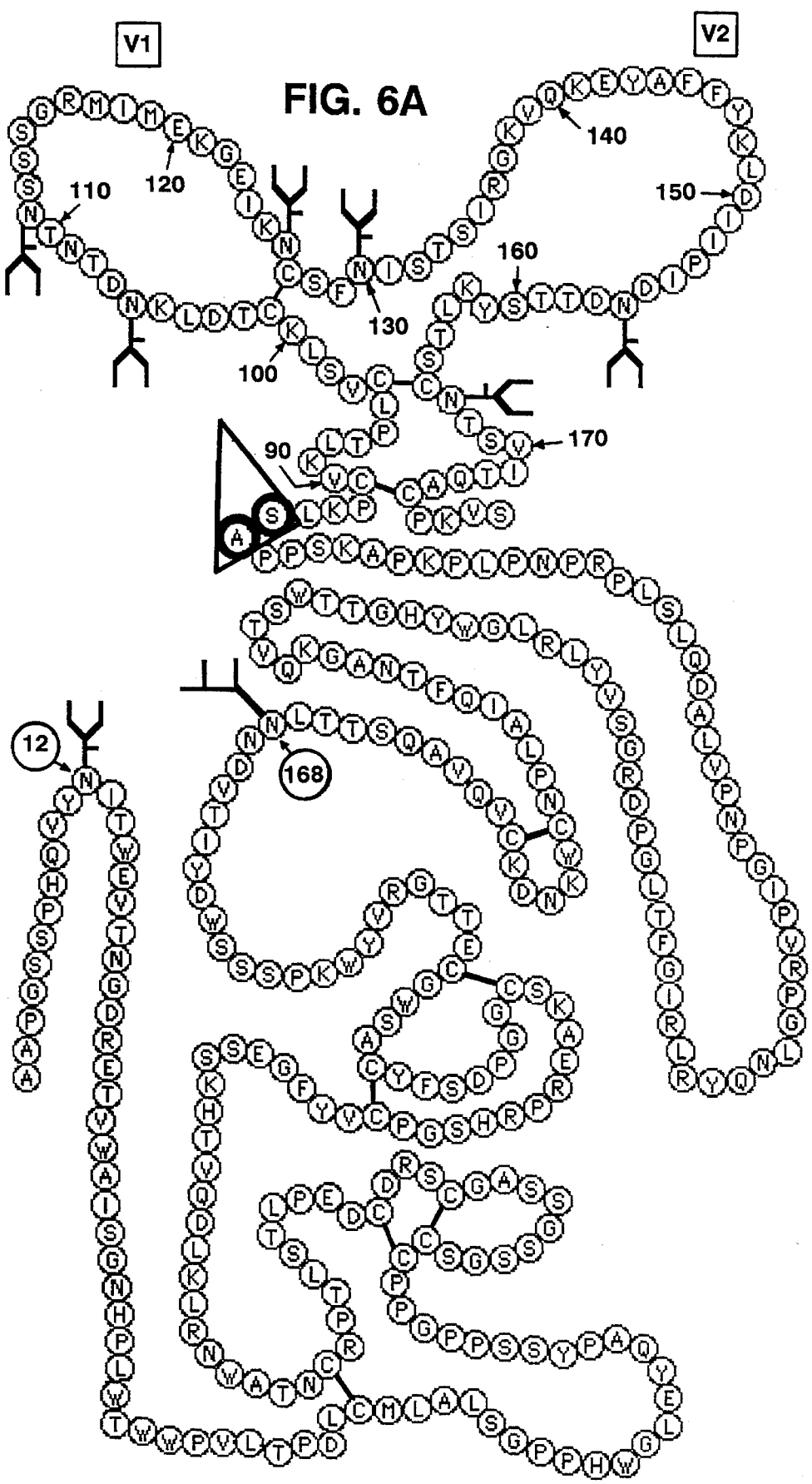
FIG. 6A shows the disulfide bonded structure of gp(1–263) V1/V2 fusion glycoprotein described in the Examples.

FIG. 6A shows the structure of the fusion protein, showing disulfide bonds and glycosylation sites of both the gp70-derived region and the gp120-derived region. The two regions are separated by an ala-ser dipeptide linker marked by a triangle. The two N-linked glycosylation sites in the gp70 region are residues 12 and 168 and are indicated by circled numbers. The glycosylation sites in the V1/V2 domains are indicated by the branched structures.

FIG. 6B shown an analysis of the immunoreactivity of the secreted gp(1–263)-V1/V2 fusion protein. Packaging cell cultures expressing the gp(1–263)-V1/V2 product were labeled with 100 uCi of 35 $^{35}$S-cysteine overnight. Cell supernatants were immunoprecipitated with MAbs CRA-3 (lane 1), C108G (lane 2), G3-4 (lane 3), sera from chimp 087 (lane 4), anti-gp70 MAb 273 (lane 5), and goat anti-gp70 serum (lane 6). Preimmune chimp and goat sera were negative, as were a number of other monoclonals against different sites on gp120. The polyclonal anti-gp70 serum also precipitates a MuLV gp70 band that is derived from the helper virus in the packaging cell line.

RESULTS

The structure of the gp(1–263)-V1/V2 fusion product is indicated in FIG. 6A. FIG. 6B shows that the expressed protein is recognized by anti V1/V2 MAbs that are dependent on glycosylation (CRA3, C108G and G3-4) and conformation (G3-4 and CRA3). This shows that proteins are expressed that are correctly folded and glycosylated.

c. Analysis of sera from HIV-1-seropositive hemophiliacs for antibodies reactive with the HXB2 V1/V2 fusion protein gp(1–263)-V1/V2.

Figure 7:
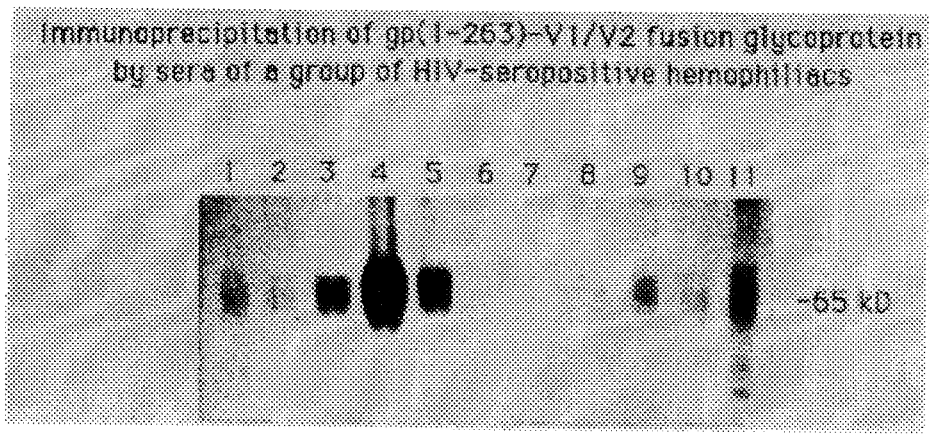
FIG. 7 shows an autoradiogram of an SDS PAGE analysis of immunoprecipitated gp(1–263) V1/V2 fusion glycoprotein described in the Examples.

3T3 cultures expressing the gp(1–263)-V1/V2 fusion product were radiolabeled with 100 uCi of $^{35}$S-cysteine overnight, and supernatant medium was immunoprecipitated with a group of sera of HIV-1-infected hemophiliacs (lanes 1–11). Radioimmunoprecipitations were performed as described for FIG. 6. All sera were tested at a dilution of 1:50. Results are shown in FIG. 7.

RESULTS

A reasonable percentage of HIV seropositive human sera contains low titers of antibodies that recognize the gp(1–263)-V1/V2 protein (lanes 1,3,5,9,11), and one patient serum (lane 4) possessed particularly potent precipitating activity against this construct. This suggests that most humans are capable of producing antibodies against the V1/V2 region. This result further suggests that the HXB2 V1/V2 sequence is either a fairly common component in the panoply of viruses seen by these patients, or it contains epitopes that are crossreactive with those seen in the V1/V2 domains of the viruses infecting these patients.

d. Quantitative immunoprecipitation of gp(1–263)-V1/V2 by goat anti-Rauscher gp70 serum.

Figure 8:
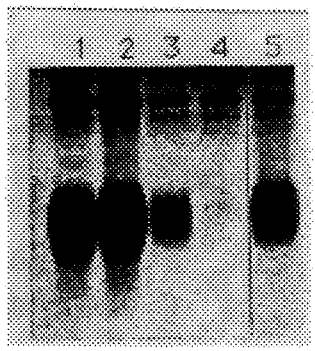
FIG. 8 shows an autoradiogram of an SDS PAGE analysis of immunoprecipitated gp(1–263) V1/V2 fusion glycoprotein described in the Examples.

Supernatant medium containing radiolabeled gp(1–263)-V1/V2 protein was immunoprecipitated sequentially 3 times with a 1:40 dilution of goat anti-gp70 serum (lanes 1–3) and then with a 1:100 dilution of serum from a chimp with a high titer of anti-V1/V2 antibody (lane 4). Results are shown in FIG. 8. Immunoprecipitation by the chimp serum without preclearing with the goat anti-gp70 serum is shown in lane 5.

RESULTS

Figure 9:
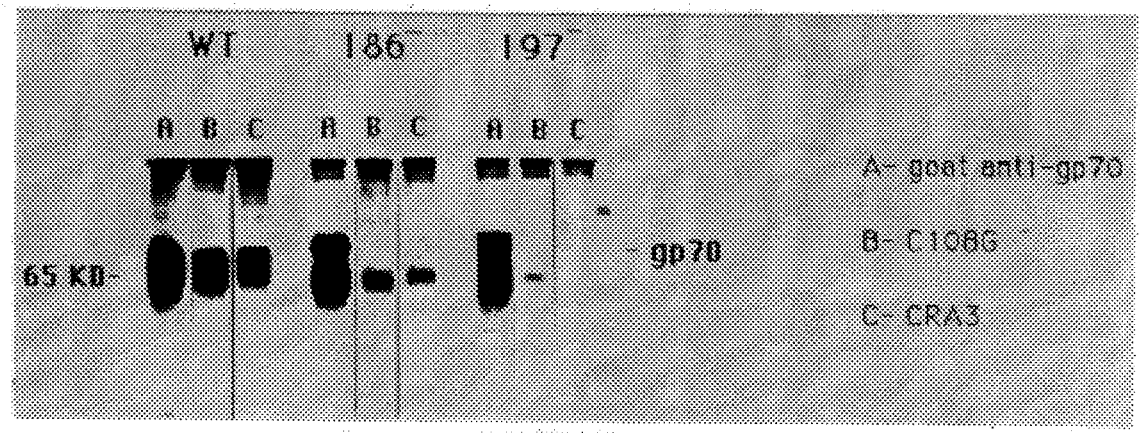
FIG. 9 shows an autoradiogram of an SDS PAGE analysis of immunoprecipitated glycosylation site mutant gp(1–263) V1/V2 fusion glycoprotein described in the Examples.

The complete removal of chimp serum immunoprecipitable material by the goat anti-gp70 serum (lane 4) shows that the goat anti-gp70 serum can quantitatively immunoprecipitate all of the gp(1–263)-V1/V2, including the fraction recognized by the chimp anti-V1/V2 antibodies. Goat serum can therefore be used to purify the fusion proteins by immunoaffinity methods.

e. Analysis of immunoreactivity of glycosylation site mutants of gp(1–263)-V1/V2 (FIG. 9).

Medium containing radiolabeled fusion proteins from cells expressing wild type gp(1–263)-V1/V2 (WT) and gp(1–263)-V1/V2 in which either the asn at position 186 (186⁻) or the one at 197 (197⁻) mutated to gln was immunoprecipitated with either goat anti-gp70 serum (lane A), MAb C108G (lane B), or MAb CRA3 (lane C). The wild type protein runs at a position corresponding to a molecular weight of 65 kD, while the mutant proteins are about 2 kD smaller. The two mutant proteins were grown in the packaging cell cultures, which contain a gp70 band contributed by the packaging virus, that is recognized by the goat anti-gp70 serum.

RESULTS

The wild type gp(1–263)-V1/V2 and the two glycosylation mutants are recognized equally well by the goat anti-gp70 serum, but the mutants are recognized only poorly, if at all, by the two monoclonal antibodies. The 197 mutant was not recognized by CRA3 at all, while both mutants react only weakly with C108G. These results document the fact that both the 186 and 197 sites are glycosylated in the wild type fusion protein, and that both the CRA3 and C108G epitopes are dependent on N-linked glycans at these two positions for proper expression.

f. Structure, expression and immunogenicity of the gp(1–263)-V3 fusion protein (FIG. 10).

Figure 10B:
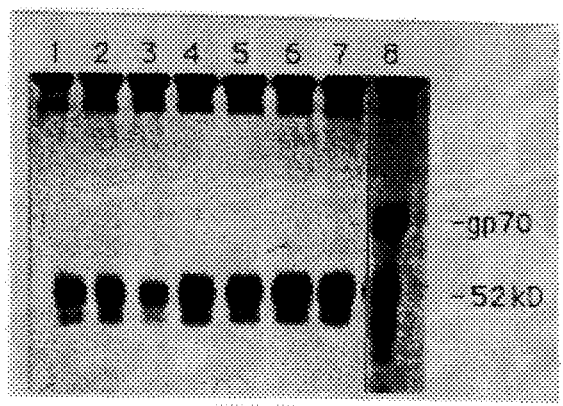
FIG. 10B shows autoradiogram of an SDS PAGE analysis of immunoprecipitated gp(1–263) V3 fusion glycoprotein described in the Examples.
Figure 10A:
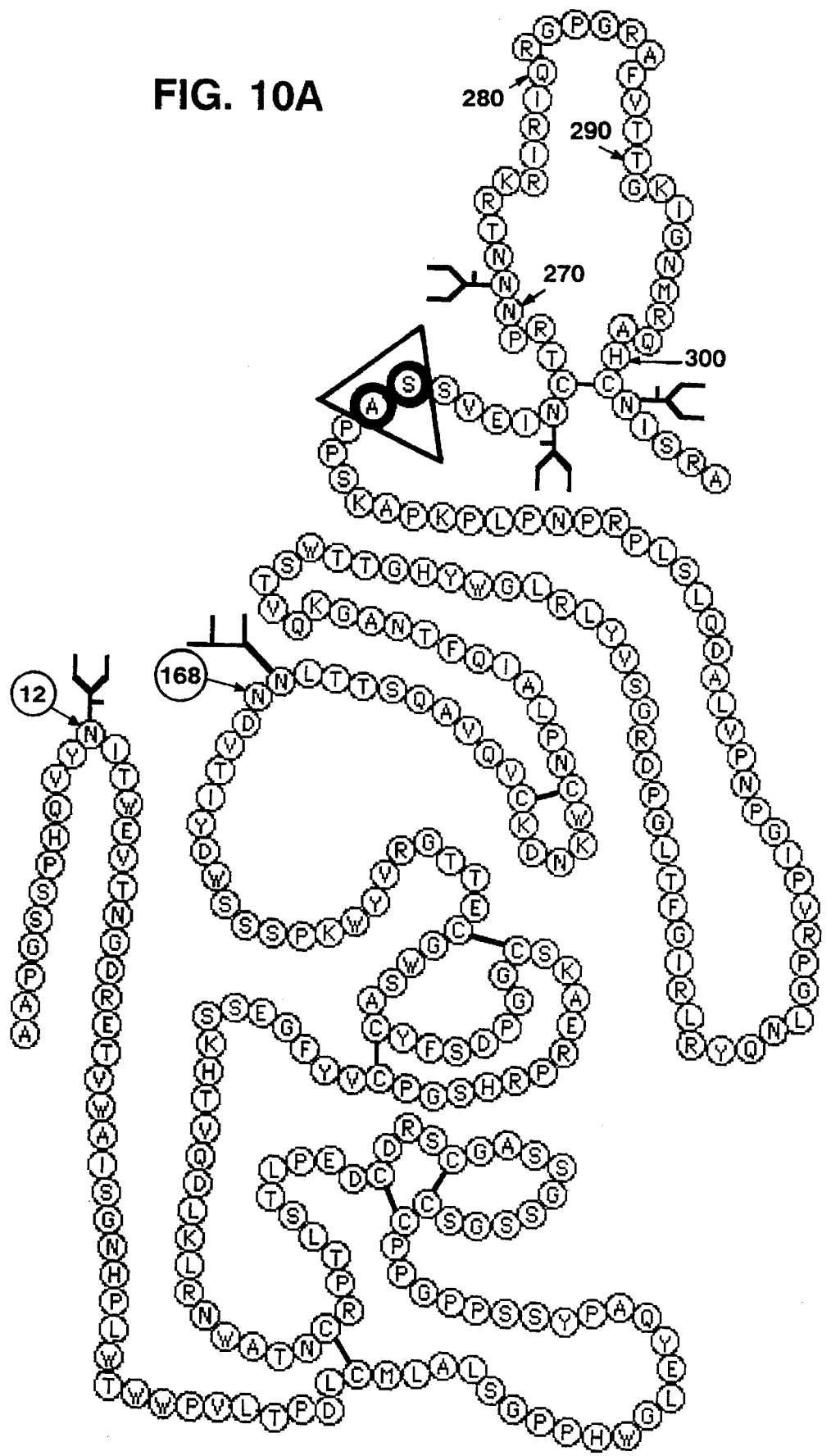
FIG. 10A shows the disulfide bonded structure of gp(1–263) V3 fusion glycoprotein described in the Examples.

In FIG. 10A the sequence of the gp(1–263)-V3 fusion protein is shown, showing the gp70 domain, the ala-ser linker dipeptide (in triangle) and the fragment of HXB2 gp120 containing amino acids 261–306. This region includes the $Cys_{266}$-$Cys_{301}$ disulfide bond, the conserved N-linked glycosylation site inside the V3 loop at position 271, and the two conserved N-linked glycosylation sites immediately outside the V3 loop at positions 265 and 302. FIG. 10B shows an analysis of the structure and immunoreactivity of the expressed fusion product. Cells expressing the V3 fusion protein were labeled with $^{35}$S-cysteine and supernatant medium immunoprecipitated with sera obtained at different dates from an HIV $_{III}$-infected chimp (lanes 1–7) or with goat anti-gp70 serum (lane 8). A fusion product of ~52 kD was recognized by the chimp and goat sera but not by sera from normal chimp or goat sera (not shown).

RESULTS

These experiments demonstrate the efficient synthesis and secretion of the gp(1–263)-V3 fusion construct in immunologically active form. The size of the expressed product suggests that the three glycosylation sites included in the V3 sequences are all utilized.

g. V3 chimeras pLRB386 carries the HXB2 V3 domain at the 263/264 site on the 46 amino acid insert that contains 3 N-linked glycans and forms an 36 amino acid. disulfide-linked loop. The recombinant env for the insertion chimera was produced in an otherwise wild type MuLV genome. When pLRB386 was transfected into 3T3 cells a spreading viral infection resulted. The growth rate of the recombinant virus was similar to that of wild type virus. By immunofluorescence, the recombinant gp70 in the intact virion was shown to present HIV-I epitopes seen by human and chimpanzee type-specific sera and by a potent neutralizing monoclonal antibody, 41.1, that is specific for an epitope in V3 not presented by synthetic peptides. Anti-V3 sera and MAbs were found to also immunoprecipitate intact virions containing the hybrid protein, indicating that these epitopes are highly exposed on the surface of intact virions. Thus, the V3 chimeric virus retains normal infectivity, and expresses a conformational epitope in V3 (the epitope for MAb 41.1) that is a potent target for neutralizing antibodies.

The amount of mature V3 chimeric gp70 produced was similar to the amount of wild type gp70 produced. A large excess of secreted N-terminal protein fragments was cleaved at a site believed to be within the V3 loop from the precursor chimeric gPr80 present in the endoplasmic reticulum. The C-terminal fragment of the cleaved precursor was degraded intracellularly. A percentage of wild type gPr80 was also degraded intracellularly without secretion of detectable fragments.

This V3 insertion chimeric virus appeared to be infectious and immunogenic in rats. Following subcutaneous injection into rats, ELISA titers vs. gp160 were detectable within 4 weeks and rose continuously for at least 18 weeks. Such an extended response to a single exposure strongly suggests that viremia was established in these animals.

A series of V3 insertion chimeras was produced and partially characterized. These included insertion glycoproteins in which the HXB2 V3 peptide was inserted at the 263/264 (pLRB386) and 285/286 sites (pLRB396), between aa 263 and 286 (pLRB395) (i.e., deleting residues 264 through 285, really 265 through 285 since aa 264 is fortuitously restored by the NheI site), and between aa 285 and 264 (pLRB392) (i.e., between repeated sequences of aa 264-285). Also, a mutant sequence in which the Cys residues defining the V3 loop were changed to Ser residues was inserted at the 263/264 site (pLRB393). These constructs had close to normal or normal growth characteristics in tissue culture and expressed the native epitope for MAb 41.1. An infectious insertion chimera carrying the MN-like V3 domain from the Jr-CSF isolate inserted at 263/264 (pLRB410) of HIV-1 was also produced. All of the V3 insertion chimeras generate high levels of a proteolytic fragment cleaved within the V3 loop, as described above.

h. V1/V2 chimeras

The HXB2 V1/V2 domain is contained within the 94 amino acid fragment (amino acids 86–179 of mature gp120) that includes three disulfide bonds. Two of these disulfide bonds generate the V1 and V2 variable loops separated by a short stretch of conserved sequence and the third disulfide bond generates an arm of conserved flanking sequences. The expressed sequence includes six signals for N-linked glycosylation, all of which have been reported to be utilized and one of which (attached to $Asn^{156}$) was found to be necessary for viral growth in cell culture. The 5' primer for producing the V1/V2 fragment was the same as used to produce the fragment for the truncation chimeric glycoprotein. The 3' primer was 5'-ACTG ATC GAT TCA TTA GGC GCC GGA TAC CTT TGG ACA GGC C-3'(SEQ ID NO: 14), which incorporated the NarI site needed for the insertion chimeric glycoprotein that was absent from the 3' primer used to generate the V1/V2 fragment for the truncation chimeric glycoprotein. This gp120 fragment was inserted into the 263/264 site by replacement of the NheI/NarI V3 gene fragment of pLRB386 to produce pLRB401. This vector expresses a viable MuLV with a gp70 of appropriate size that is recognized by type specific chimpanzee sera, by rat anti-V2 MAb 10/76b, and by a human serum that has cross-reactive anti-V1/V2 antibodies.

i. V4/C4 chimeras

The V4/C4 domain of HXB2d is contained within an 80 amino acid fragment (residues 342–421) that includes two disulfide bonds, one of which generates the V4 loop, and both of which are involved in forming the majority of the C4 region into a loop. 21 amino acids of the C3 region are included in this construct, and the last 12 amino acids of the C4 region are not. The sequence includes 5 signals for N-linked glycosylation, all of which have been reported to be utilized and none of which was found to be necessary for viral growth in cell culture. The 5' primer for producing the V4/C4 fragment was 5'-CATC GCT AGC GTA ACG CAC AGT TTT AAT TGT GGA-3' (SEQ ID NO: 15). The 3' primer was 5'-ACTG ATC GAT CTA TTA GGC GCC CCC TGT AAT ATT TGA ACA T-3'(SEQ ID NO: 16). The vector expressing this insertion chimera, pLRB408, was constructed in the same manner as pLRB401. It expresses infectious MuLV with a gp70 of appropriate size that is recognized by rat anti-C4 MAb 38.1

The interdomain linker region of gp70 thus appears to be remarkably tolerant of both insertions and rearrangements.

USE OF CHIMERIC GLYCOPROTEINS TO ANALYZE IMMUNE SERA

A fusion glycoprotein containing the V3 domain of the IIIB strain of HIV-1, gp(1–263):V3$_{HXB2}$, was recognized by sera from a human and a chimpanzee that had been infected by HIV$_{IIIB}$ but not by sera from hemophiliac patients that had been infected with HIV-1 viruses of MN-like V3 serotype. The reactive sera had approximately five-fold higher ELISA titers when assayed on gp(1–263):V3$_{HXB2}$ than on matching V3 peptides. Immunoprecipitation of this fusion glycoprotein by the human serum was only partially blocked by V3 peptide, demonstrating that this infected individual produced antibodies against epitopes in V3 that were expressed on the fusion glycoprotein but not by synthetic peptides. A fusion protein containing the HXB2 V1/V2 domain was recognized by the HIV$_{IIIB}$-infected patient serum as well as by 17 out of 36 HIV-1 seropositive hemophiliac, gay male and intravenous drug user patient sera. Many of these HIV$^+$human sera reacted with V1/V2 domains from several HIV-1 clones expressed in fusion glycoproteins, (Jr-CSF, pLRB357; NL4-3, pLRB359; SF2, pLRB360; MN-ST, pLRB361; Jr-FL, pLRB362). These results indicate the presence of cross-reactive antibodies against epitopes in the V1/V2 domain. Recognition of gp(1–263):V1/V2$_{HXB2}$ by the HIV$_{IIIB}$-infected human patient serum was largely blocked by synthetic peptides matching V1 but not V2 sequences, while recognition of this construct by a broadly cross-reactive hemophiliac patient serum was not blocked by individual V1 or V2 peptides or by mixtures of these peptides. These data demonstrated that the chimeric glycoproteins described here effectively present native epitopes present in the V1/V2 and V3 domains of gp120 and provide efficient methods for detection of antibodies directed against native epitopes in these regions.

EXPRESSION OF FUSION GLYCOPROTEINS USING VACCINIA

One can express a fusion glycoprotein of this invention from a vaccinia virus vector. One such vector is the recently developed NYVAC vector, a highly attenuated strain of vaccinia virus that is able to elicit immune responses to foreign proteins inserted into the viral genome (Tartaglia et al., 1992, Virology 188:217–232). Although unable to replicate on human derived cells, NYVAC does infect various human cells and allows for the expression of foreign proteins in human cells. Virus can be grown, amplified, and manipulated in Vero cells (ATCC No. CCL81) or primary chick embryo fibroblasts. To insert a foreign gene into a vaccinia virus, an intermediate plasmid vector is constructed in which the selected gene is appropriately linked to the thymidine kinase gene (tk) promoter. Plasmids carrying a fragment of the vaccinia genome surrounding the tk gene in which tk gene sequences need to be replaced with a multiple cloning site, such as pSD460 (Tartaglia et al., 1992, Virology 188:217–232), are used for this purpose. Standard recombinant DNA techniques are used to insert the selected fusion glycoprotein gene into such a vector. If an insertion chimeric glycoprotein is to be expressed along with a gag gene to provide for defective particle formation, it is also incorporated into pSD460 or its equivalent between the flanking vaccinia sequences. It also needs to be associated with a promoter, which can be a second copy of the vaccinia tk promoter. Alternatively it can be associated with a heterologous promoter such as the enhancer/promoter sequences from the widely used immediate early gene of human cytomegalovirus. Following construction of the plasmid vector containing the selected gene or genes associated with promoters (and situated between flanking vaccinia sequences from the tk region of the virus genome), in vivo recombination is used to introduce the selected genes into the complete virus genome. This is accomplished by co-transfecting the plasmid vector DNA and NYVAC genomic DNA into a cell line, such as Vero, to allow recombinants to form. Recombinant virus is identified by plaque hybridization with radiolabelled DNA probes for the inserted genes. The recombinant virus is used for inoculation of mammals or infection of cells in culture for production of fusion glycoproteins.

PLASMID VECTORS FOR EXPRESSION OF FUSION GLYCOPROTEINS

One can express a fusion glycoprotein of the invention from a non-replicating vector such as pRc/CMV (Invitrogen, San Diego Calif.). Standard molecular biological techniques are used to insert the gene for the selected env fusion glycoprotein into the multiple cloning site adjacent to the enhancer/promoter sequences from the immediate early gene of the human cytomegalovirus. If it is desired to express a gag gene to allow particle formation, the gag gene could be substituted for the neomycin gene in this vector that is expressed from a Rous sarcoma virus LTR. Following insertion of the selected gene or genes into the plasmid vector, the plasmid DNA is transfected into appropriate mammalian cells, such as mouse 3T3 or Vero monkey, for expression of fusion glycoprotein in culture. If the neomycin gene of the vector has not been removed, transfectant lines are selected for G418 resistance and screened for appropriate production of the fusion glycoprotein. If the neomycin gene has been removed, the plasmid vector for expression of the fusion glycoprotein is co-transfected with 1/25 as much of another vector that carries a drug-selectable marker to allow selection of transfectant cell lines. To use a plasmid vector for expression of fusion glycoproteins in mammals, direct DNA immunization is used. Purified plasmid DNA is inoculated into the mammal by any of a number of methods, for example, by intramuscular injection of non-replicating expression vector DNA. This method has been shown to be effective for immunizing mice with influenza A nucleoprotein (Ulmer et al 1993 Science 259:1745–1749).

PARTICLE BASED PURIFICATION

This invention can be used as a method for the production and purification of specific glycopeptides. The amount of insertion chimeric glycoprotein produced is generally less than the amount of the corresponding truncation chimeric glycoprotein. This is due to the relatively inefficient processing of the precursor protein encoded by complete env genes with or without insertions. The lower amount produced, however, may be balanced by the fact that the insertion chimeric glycoproteins will, in general, be associated with virus particles rather than as soluble proteins like the truncation chimeric glycoproteins. The virus particles and associated insertion chimeric glycoproteins are separated from soluble proteins by, e.g., size exclusion chromatography (Pinter, Honnen and Tilley 1993 J. Virol. In Press) or filtration through substrates with appropriate pore sizes, as well as by sedimentation velocity or sedimentation density methods, methods that are used on preparative scales. Following separation from soluble components, the insertion chimeric glycoproteins are released from the particle by conventional methods such as: reduction of disulfide bonds; treatment with detergents such as octylglucoside, NP40, or Triton X-100; treatment with chaotropic agents such as guanidine hydrochloride, urea, or lithium chloride. Treatments that have a negative impact on the properties of the glycopeptide being produced are avoided. Following release of the insertion chimeric glycoproteins, the glycoproteins are purified away from the other viral proteins. If the viral membrane has not been disrupted, the methods used to separate the particles from soluble proteins can be used to separate the fusion glycoproteins from the other particle associated proteins. If the viral membrane has been solubilized but the viral core remains intact, the insertion chimetic glycoproteins can be separated from the core proteins as above, and the insertion chimeric glycoproteins purified away from the transmembrane vital protein by standard protein chemistry techniques. If the entire viral particle is disrupted and its component proteins solubilized, the insertion chimeric glycoproteins can be purified from the other viral protein by standard protein chemistry techniques. This is easier than purifying a soluble protein from cell supernatants. The fraction of the mixture that is fusion glycoprotein is greater and there are fewer contaminating proteins.

Following purification of the insertion chimeric glycoproteins, the selected glycopeptide can be cleaved from the carrier SU protein domains. To do so, cleavage sites for sequence specific proteases are incorporated into the insertion chimeric glycoproteins both immediately N-terminal and immediately C-terminal to the glycopeptide. Different cleavage targets can be used on either side of the glycopeptide. One site can be the blood coagulation factor Xa cleavage site (see above), and the other can be the Leu-val-pro-arg-gly-ser (SEQ ID NO: 25) cleavage site of thrombin. The selected glycopeptide is then purified from the fragments of SU (and the proteases, unless immobilized proteases are used) by standard protein chemistry techniques.

We claim:

1. In an expression vector for infecting or transfecting a cell to express a glycosylated protein, the improvement wherein said protein is a fusion glycoprotein comprising (a) an amino acid sequence that has a biological activity and is from a protein that lacks a hydrophobic glycosylation signal located about seven residues N-terminal to a Cys-Trp-leu-cys sequence (Seq. ID. No. 18), said amino acid sequence being operably linked to the C-terminus of (b) a retrovirus env surface protein, N-terminal carrier fragment that includes all of the Cys residues of the N-terminal globular domain of said surface protein, and further wherein said env surface protein contains an N-glycan attachment site within a hydrophobic glycosylation signal located about seven residues N-terminal to a Cys-trp-leu-cys sequence (Seq. ID. No. 18).

2. The expression vector of claim 1 wherein said fusion glycoprotein comprises a cleavable linker operably linked between said env fragment and said amino acid sequence.

3. The expression vector of claim 1 wherein said biological activity is dependent on the conformation of said amino acid sequence.

4. The expression vector of claim 1 wherein said amino acid sequence comprises at least one N-glycan dependent epitope.

5. The expression vector of claim 1 wherein said amino acid sequence comprises an immunoreactive or immunogenic epitope.

6. The expression vector of claim 5 wherein the immunoreactivity or immunogenicity of said epitope is dependent on the conformation of said amino acid sequence.

7. The expression vector of claim 5 wherein the immunoreactivity or immunogenicity of said epitode is dependent on the glycosylation of said amino acid sequence.

8. The expression vector of claim 1 wherein said amino acid sequence comprises the V1/V2 region of gp120 of HIV-1 or a glycosylated fragment thereof.

9. The expression vector of claim 1 wherein said fusion glycoprotein has a molecular weight greater than 20,000 daltons.

10. The expression vector of claim 1 wherein said amino acid sequence is less than 150 amino acids long.

11. The expression vector of claim 1 that is a virus for infecting mammalian cells.

12. The expression vector of claim 1 that is a plasmid for transfecting mammalian cells.

13. The expression vector of claim 1 wherein said amino acid sequence comprises the V2 region of gp120 of HIV-1 or a glycosylated fragment thereof.

14. The expression vector of claim 1 wherein said amino acid sequence comprises the V1 region of gp120 of HIV-1 or a glycosylated fragment thereof.

15. The expression vector of claim 1 wherein said amino acid sequence comprises the V3 region of gp120 of HIV-1 or a glycosylated fragment thereof.

16. The expression vector of claim 1 wherein said amino acid sequence comprises the amino acid sequence of the V1/V2 domain of gp120 of HIV-1.

17. The expression vector of claim 1 wherein said amino acid sequence comprises the V3 domain of gp120 of HIV-1.

18. The expression vector of claim 1 wherein said amino acid sequence comprises the V2 domain of gp120 of HIV-1.

19. The expression vector of claim 1 wherein said amino acid sequence is amino acid sequence 86–179 of gp120 of the HXB2d strain, or a corresponding sequence of another HIV-1 strain.

20. The expression vector of claim 1 wherein said amino acid sequence is amino acid sequence 261–306 of gp120 of the HXB2d strain, or a corresponding sequence of another HIV-1 strain.

21. The expression vector of claim 1 wherein said amino acid sequence comprises at least one disulfide linkage.

22. The expression vector of claim 1 wherein said amino acid sequence includes at least one glycosylation site.

23. The expression vector of claim 1 wherein said biological activity is dependent on glycosylation of said amino acid sequence.

24. The expression vector of claim 1 wherein said amino acid sequence binds a receptor.

25. The expression vector of claim 1 wherein said amino acid sequence is a receptor ligand.

26. The expression vector of claim 1 wherein said amino acid sequence binds a hormone.

27. The expression vector of claim 1 wherein said amino acid sequence participates in an immunoreaction.

28. The expression vector of claim 1 further wherein said env surface protein comprises at least a portion of an interdomain linker region extending from the last Cys residue of said N-terminal globular domain to said N-glycan attachment site.

29. The expression vector of claim 28 wherein said fusion glycoprotein further comprises the C-terminal globular domain of the env surface protein operably linked to the C-terminus of said amino acid sequence.

30. The expression vector of claim 29 wherein said expression vector expresses env trans-membrane protein.

31. The expression vector of claim 30 wherein said fusion glycoprotein is incorporated into a viral envelope when said fusion glycoprotein is coexpressed with a gag gene.

32. The expression vector of claim 29 wherein said amino acid sequence is operably inserted in said at least a portion of the interdomain linker region.

33. The expression vector of claim 32 wherein said N-terminal fragment includes the env receptor binding domain.

34. The expression vector of claim 29 comprising genes for expressing a particle of said retrovirus.

35. The expression vector of claim 29 comprising genes for expressing a non-infectious viral particle.

36. The expression vector of claim 35 wherein said fusion protein lacks the activity of SU in mediating viral infection.

37. The expression vector of claim 35 wherein said viral particle contains a defective viral genome.

38. The expression vector of claim 35 wherein said fusion protein is incorporated into the membrane of a pseudotyped viral particle containing a defective viral genome.

39. The expression vector of claim 29 comprising genes for expressing an infectious particle.

40. The expression vector of claim 39 wherein said fusion protein retains the activity of SU in mediating viral infection.

41. The expression vector of claim 39 comprising a complete viral genome wherein said fusion glycoprotein replaces the viral env protein.

42. The expression vector of claim 39 wherein said amino acid sequence binds a receptor.

43. The expression vector of claim 39 wherein said amino acid sequence is a receptor ligand.

44. The expression vector of claim 39 wherein said amino acid sequence participates in an immunoreaction.

45. The expression vector of claim 39 wherein said viral particle is a pseudotyped viral particle.

46. The expression vector of claim 39 comprising genes for expressing a viral particle that is infectious in humans.

47. The expression vector of claim 46 wherein said viral particle causes viremia.

48. The expression vector of claim 46 wherein said viral particle is a pseudotyped viral particle.

49. The expression vector of claim 39 comprising genes for expressing a viral particle that is infectious in a human cell line.

50. The expression vector of claim 34 wherein said fusion glycoprotein is not incorporated into said retroviral particle during expression.

51. The expression vector of claim 35 comprising a gag gene and lacking a complete pol gene.

52. The expression vector of claim 28 wherein said N-terminal fragment is an N-terminal fragment of MuLV env protein gp70.

53. The expression vector of claim 52 wherein said N-terminal fragment includes the MuLV env receptor binding domain.

54. The expression vector of claim 52 wherein said fusion glycoprotein further comprises the C-terminal globular domain of said gp70 operably linked to the C-terminus of said amino acid sequence, said expression vector further expressing env anchor protein p15e.

55. The expression vector of claim 53 wherein said N-terminal fragment is the N-terminal 263 amino acids of MuLV env.

56. The expression vector of claim 53 wherein said N-terminal fragment is the N-terminal 285 amino acids of MuLV env.

57. The expression vector of claim 28 wherein said N-terminal fragment comprises at least a portion of said interdomain linker region.

58. The expression vector of claim 54 wherein said amino acid sequence is operably inserted in said at least a portion of the interdomain linker region.

59. The expression vector of claim 52 wherein said N-terminal fragment comprises at least a portion of the interdomain linker region.

60. The expression vector of claim 59 which is a MuLV vector comprising MuLV sequences from the plasmid designated pLRB332 having ATCC accession number 69057, and wherein said fusion glycoprotein comprises amino acids 86–179 of gp120 of the HXB2d strain, or a corresponding sequence of another HIV-1 strain, operably linked to the C-terminus of said N-terminal env fragment.

61. The expression vector of claim 58 which is a MuLV vector comprising MuLV sequences from the plasmid designated pLRB332 having ATCC accession number 69057, and wherein said fusion glycoprotein comprises amino acids 261–306 of gp120 of the HXB2d strain, or a corresponding sequence of another HIV-1 strain, operably linked to the C-terminus of said N-terminal env fragment.

62. The expression vector of claim 52 wherein the MuLV virus is the Friend strain.

63. The expression vector of claim 28 further wherein said interdomain linker region includes a region that is Pro-rich.

64. A mammalian cell line infected or transfected by the expression vector of claim 1.

65. A mammalian cell line infected or transfected by the expression vector of claim 53.

66. 3T3 cells transfected or infected by the expression vector of claim 52.

67. A mammalian cell line infected or transfected by the expression vector of claim 29.

68. A mammalian cell line infected or transfected by the expression vector of claim 34.

69. A process for the preparation of a fusion glycoprotein comprising:

(a) inoculating an appropriate medium with cells of the mammalian cell line according to claim 64;

(b) culturing said cells;

(c) recovering the fusion glycoprotein.

70. The process according to claim 69 wherein said fusion glycoprotein is recovered from the supernatant of said medium.

71. The process according to claim 70 wherein said fusion glycoprotein is recovered using an antibody, said antibody binding an epitope of said amino acid sequence in an immunoreaction, and said epitope being dependent on the conformation or glycosylation of said amino acid sequence.

72. A process for the preparation of a fusion glycoprotein comprising:

(a) inoculating an appropriate medium with cells of the mammalian cell line according to claim 68;

(b) culturing said cells; and (c) recovering viral particles containing said fusion glycoprotein.

73. A process for the preparation of a fusion glycoprotein comprising:

(a) inoculating an appropriate medium with cells of the mammalian cell line according to claim 67, wherein said cells comprise genes for expressing a virus particle and express said genes;

(b) culturing said cells; and (c) recovering viral particles containing the fusion glycoprotein.

74. The process according to claim 73, wherein said viral particles are pseudotyped viral particles.

* * * * *

UNITED STATES PATENT AND TRADEMARK OFFICE
CERTIFICATE OF CORRECTION

PATENT NO.   : 5,643,756
DATED        : July 1, 1997
INVENTOR(S)  : Samuel Kayman and Abraham Pinter It is certified that error appears in the above-identified patent and that said Letters Patent is hereby corrected as shown below:

In the claims

Delete claim 1 (col. 55, lines 16-31) and substitute therefor:

--1. In an expression vector for infecting or transfecting a cell to express a glycosylated protein, the improvement wherein said protein is a fusion glycoprotein comprising (a) an amino acid sequence that has a biological activity and is from a protein that lacks a hydrophobic glycosylation signal located about seven residues N-terminal to a Cys-Trp-leu-cys sequence (Seq. ID. No. 18), said amino acid sequence being operably linked to the C-terminus of (b) a retrovirus *env* surface protein N-terminal carrier fragment that includes all of the Cys residues of the N-terminal globular domain of said surface protein, and further wherein said *env* surface protein contains an N-glycan attachment site within a hydrophobic glycosylation signal located about seven residues N-terminal to a Cys-trp-leu-cys sequence (Seq. ID. No. 18).--

Signed and Sealed this

Thirty-first Day of March, 1998

Attest:

BRUCE LEHMAN

*Attesting Officer*          *Commissioner of Patents and Trademarks*

UNITED STATES PATENT AND TRADEMARK OFFICE
CERTIFICATE OF CORRECTION

PATENT NO.   : 5,643,756

DATED        : July 1, 1997

INVENTOR(S)  : Samuel Kayman et al.

It is certified that error appears in the above-identified patent and that said Letters Patent is hereby corrected as shown below:

<u>In the claims</u>:

Claim 7, line 2, "epitode" should be --epitope--.

Claim 61, line 1, "claim 58" should be --claim 59--.

Signed and Sealed this

Second Day of February, 1999

Attest:

Attesting Officer

Acting Commissioner of Patents and Trademarks

UNITED STATES PATENT AND TRADEMARK OFFICE
CERTIFICATE OF CORRECTION

PATENT NO. : 5,643,756
DATED : JULY 1, 1997
INVENTOR(S) : SAMUEL KAYMAN AND ABRAHAM PINTER

It is certified that error appears in the above-identified patent and that said Letters Patent is hereby corrected as shown below:

Col. 2, line 19, replace "FIG. 1 shows" with --FIGS. 1A-1E show--.
Col. 2, line 19, delete "and amino acid".
Col. 2, line 22, replace "FIG. 3A shows" with --FIGS. 3A-3F show--.
Col. 2, line 27, replace "FIG. 3B shows" with --FIGS. 3G-3H show--.
Col. 2, line 31, after "top sequence" insert --(FIG. 3G)--.
Col. 2, line 32, after "bottom sequence" insert --(FIG. 3H)--.
Col 12, line 55, replace "FIG. 1 shows" with --FIGS. 1A-1E show--.
Col 13, line 55, replace "FIG. 3A shows" with --FIGS. 3A-3F show--.
Col. 13, line 57, replace "FIG. 3B shows" with --FIGS. 3G and 3H show--.
Col. 18, line 58, replace "FIG. 6" with --FIG. 6B--.
Col. 19, line 53, replace "(FIG. 10)" with --(FIG. 10A and 10B)--.

Signed and Sealed this

Twentieth Day of February, 2001

*Attest:*

NICHOLAS P. GODICI

*Attesting Officer*   Acting Director of the United States Patent and Trademark Office

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

CTCAGCCCCC GCCAGCAGGA GCTAGCTAAT GAATCGATAA CC 42

( 2 ) INFORMATION FOR SEQ ID NO:2:

( i ) SEQUENCE CHARACTERISTICS:
( A ) LENGTH: 42 base pairs ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

GGTTATCGAT TCATTAGCTA GCGGGGGGAG ACTTGGCAGG TT                         42

( 2 ) INFORMATION FOR SEQ ID NO:3:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

CCAAGAAGCT TCTAGAAGAA A                                               21

( 2 ) INFORMATION FOR SEQ ID NO:4:

( i ) SEQUENCE CHARACTERISTICS:
                ( A ) LENGTH: 31 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

CATCGCTAGC CTAAAGCCAT GTGTAAAATT A                                    31

( 2 ) INFORMATION FOR SEQ ID NO:5:

( i ) SEQUENCE CHARACTERISTICS:
                ( A ) LENGTH: 35 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

ACTGATCGAT TCATTAGGAT ACCTTTGGAC AGGCC                                35

( 2 ) INFORMATION FOR SEQ ID NO:6:

( i ) SEQUENCE CHARACTERISTICS:
                ( A ) LENGTH: 28 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

| | | | |
|---|---|---|---|
| CGGTGCTAGC TCTGTAGAAA TTAATTGT | | | 2 8 |

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

CTAGATCGAT CTATTAGGCG CCTGCTCTAC TAATGTTACA        40

( 2 ) INFORMATION FOR SEQ ID NO:8:

( i ) SEQUENCE CHARACTERISTICS:
        ( A ) LENGTH: 8323 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

| | | | | | |
|---|---|---|---|---|---|
| GCGCCAGTCC | TCCGATAGAC | TGAGTCGCCC | GGGTACCCGT | GTATCCAATA | AATCCTCTTG | 60 |
| CTGTTGCATC | CGACTCGTGG | TCTCGCTGTT | CCTTGGGAGG | GTCTCCTCAG | AGTGATTGAC | 120 |
| TACCCGTCTC | GGGGGTCTTT | CATTTGGGGG | CTCGTCCGGG | ATCTGGAGAC | CCCTGCCCAG | 180 |
| GGACCACCGA | CCCACCACCG | GGAGGTAAGC | TGGCCAGCAA | TTGTTCTGTG | TCTGTCCATT | 240 |
| GTCCTGTGTC | TTTGATTGAT | TTATGCGCC | TGTGTCTGTA | CTAGTTGGCC | GACTAGATTG | 300 |
| GTATCTGGCG | GATCCGTGGT | GGAACTGACG | AGTTCGAGAC | ACCCGGCCGC | AACCCTGGGA | 360 |
| GACGTCCCAG | GGACTTCGGG | GGCCATTTTT | GTGGCCCGGC | CAGAGTCCAA | CCATCCCGAT | 420 |
| CGTTTTGGAC | TCTTTGGTGC | ACCCCCCTTA | GAGGAGGGGT | ATGTGGTTCT | GGTAGGAGAC | 480 |
| AGAGGGCTAA | AACGGTTTCC | GCCCCCGTCT | GAGTTTTTGC | TTTCGGTTTG | GAACCGAAGC | 540 |
| CGCGCCGCGC | GTCTTGTCTG | CTGCAGCATC | GTTCTGTGTT | GTCTCTGTTT | GACTGTTTTT | 600 |
| CTGTATTTGT | CTGAAAACAT | GGGCCAGGCT | GTTACCACCC | CTTAAGTTT | GACTTTAGAC | 660 |
| CACTGGAAGG | ATGTCGAACG | GACAGCCCAC | AACCTGTCGG | TAGAGGTTAG | AAAAAGGCGC | 720 |
| TGGGTTACAT | TCTGCTCTGC | AGAATGGCCA | ACCTTAACG | TCGGATGGCC | ACGAGACGGC | 780 |
| ACTTTTAACC | CAGACATTAT | TACACAGGTT | AAGATCAAGG | TCTTCTCACC | TGGCCCACAT | 840 |
| GGACATCCGG | ATCAGGTCCC | CTACATCGTG | ACCTGGGAAG | CTATAGCAGT | AGACCCCCT | 900 |
| CCCTGGGTCA | GACCCTTCGT | GCACCCTAAA | CCTCCCTCT | CTCTTCCCCC | TTCAGCCCCC | 960 |
| TCTCTCCCAC | CTGAACCCCC | ACTCTCGACC | CCGCCCCAGT | CCTCCCTCTA | TCCGGCTCTC | 1020 |

-continued

```
ACTTCTCCTT TAAACACCAA ACCTAGGCCT CAAGTCCTTC CTGATAGCGG AGGACCACTC    1080
ATTGATCTAC TCACGGAGGA CCCTCCGCCT TACCGGGACC CAGGGCCACC CTCTCCTGAC    1140
GGGAACGGCG ATAGCGGAGA AGTGGCCCCT ACAGAAGGAG CCCCTGACCC TTCCCCAATG    1200
GTATCCCGCC TGCGGGGAAG AAAAGAACCC CCCGTGGCGG ATTCTACTAC CTCTCAGGCG    1260
TTCCCCCTTC GCCTGGGAGG GAATGGACAG TATCAATACT GGCCATTTTC CTCCTCTGAC    1320
CTCTATAACT GGAAAAATAA CAACCCCTCT TTCTCCGAGG ACCCAGCTAA ATTGACAGCT    1380
TTGATCGAGT CCGTTCTCCT TACTCATCAG CCCACTTGGG ATGACTGCCA ACAGCTATTA    1440
GGGACCCTGC TGACGGGAGA AGAAAAACAG CGAGTGCTCC TAGAGGCCCG AAAGGCGGTT    1500
CGAGGGGAGG ACGGACGCCC AACTCAGCTG CCCAATGACA TTAATGATGC TTTTCCCTTG    1560
GAACGTCCCG ACTGGGACTA CAACACCCAA CGAGGTAGGA ACCACCTAGT CCACTATCGC    1620
CAGTTGCTCC TAGCGGGTCT CCAAAACGCG GGCAGAAGCC CCACCAATTT GGCCAAGGTA    1680
AAAGGGATAA CCCAGGGACC TAATGAGTCT CCCTCAGCCT TTTTAGAGAG ACTCAAGGAG    1740
GCCTATCGCA GATACACTCC TTATGACCCT GAGGACCCAG GGCAAGAAAC CAATGTGGCC    1800
ATGTCATTCA TCTGGCAGTC CGCCCCGGAT ATCGGGCGAA AGTTAGAGCG GTTAGAAGAT    1860
TTGAAGAGTA AGACCTTAGG AGACTTAGTG AGGGAAGCTG AAAAGATCTT TAATAAACGA    1920
GAAACCCCGG AAGAAAGAGA GGAACGTATT AGGAGAGAAA CAGAGGAAAA GGAAGAACGC    1980
CGTAGGGCAG AGGATGTGCA GAGAGAGAAG GAGAGGGACC GCAGAAGACA TAGAGAAATG    2040
AGTAAGTTGC TGGCTACTGT CGTTAGCGGG CAGAGACAGG ATAGACAGGG AGGAGAGCGA    2100
AGGAGGCCCC AACTCGACCA CGACCAGTGT GCCTACTGCA AAGAAAGGG ACATTGGGCT    2160
AGAGATTGCC CCAAGAAGCC AAGAGGACCC CGGGGACCAC GACCCCAGGC CTCCCTCCTG    2220
ACCTTAGACG ATTAGGGAGG TCAGGGTCAG GAGCCCCCCC CTGAACCCAG ATAACCCTC     2280
AGAGTCGGGG GGCAACCCGT CACCTTCCTA GTGGATACTG GGCCCAACA CTCCGTGCTG    2340
ACCCAAAATC CTGGACCCCT AAGTGACAAG TCTGCCTGGG TCCAAGGGGC TACTGGAGGG    2400
AAGCGGTATC GCTGGACCAC GGATCGCCGA GTGCACCTAG CCACCGGTAA GGTCACCCAT    2460
TCTTTCCTCC ATGTACCAGA TTGCCCCTAT CCTCTGCTAG GAAGAGATTT GCTGACTAAA    2520
CTAAAAGCCC AAATTCACTT TGAGGGATCA GGAGCTCAGG TTGTGGGACC AATGGGACAG    2580
CCCCTGCAAG TGCTGACCCT AAACATAGAA GATGAGTATC GGCTACATGA GACCTCAAAA    2640
GGGCCAGATG TGCCTCTAGG GTCCACATGG CTCTCTGATT TTCCCCAGGC CTGGGCAGAA    2700
ACCGGGGGCA TGGGGCTGGC CGTTCGCCAA GCTCCTCTGA TCATACCTCT GAAGGCAACC    2760
TCTACCCCCG TGTCCATAAA ACAATACCCC ATGTCACAAG AAGCCAGACT GGGGATCAAG    2820
CCCCACATAC AGAGACTGCT GGATCAGGGA ATTCTGGTAC CCTGCCAGTC CCCCTGGAAC    2880
ACGCCCTGC TACCCGTTAA GAAACCGGGG ACTAATGATT ATAGGCCTGT CCAGGATCTG    2940
AGAGAAGTCA ACAAGCGGGT GGAAGACATC CACCCCACCG TGCCCAACCC TTACAACCTC    3000
TTGAGCGGGC TCCCACCGTC CCACCAGTGG TACACTGTGC TTGACTTAAA AGATGCTTTT    3060
TTCTGCCTGA GACTCCACCC CACCAGTCAG TCTCTCTTCG CCTTTGAGTG GAGAGATCCA    3120
GAGATGGGAA TCTCAGGACA ATTAACCTGG ACCAGACTCC CGCAGGGTTT CAAAAACAGT    3180
CCCACCCTGT TTGATGAAGC CCTGCACAGG GACCTCGCAG ACTTCCGGAT CCAGCACCCA    3240
GACCTGATTC TGCTCCAGTA TGTAGATGAC TTACTGCTGG CCGCCACTTC TGAGCTTGAC    3300
TGTCAACAAG GTACGCGGGC CCTGTTACAA ACCCTAGGGG ACCTCGGATA TCGGGCCTCG    3360
GCCAAGAAAG CCCAAATTTG CCAGAAACAG GTCAAGTATC TGGGGTATCT TCTAAAAGAG    3420
```

-continued

| | | | | | |
|---|---|---|---|---|---|
| GGTCAGAGAT | GGCTGACTGA | GGCCAGAAAA | GAGACTGTGA | TGGGGCAGCC | TACTCCGAAG | 3480 |
| ACCCCTCGAC | AACTAAGGGA | GTTCCTAGGG | ACGGCAGGCT | TCTGTCGCCT | CTGGATCCCT | 3540 |
| GGGTTTGCAG | AAATGGCAGC | CCCCTTGTAC | CCTCTCACCA | AAACGGGGAC | TCTGTTTGAG | 3600 |
| TGGGGCCCAG | ACCAGCAAAA | GGCCTACCAA | GAGATCAAGC | AGGCTCTCTT | AACTGCCCCT | 3660 |
| GCCCTGGGAT | TGCCAGACTT | GACTAAGCCC | TTCGAACTTT | TTGTTGACGA | GAAGCAGGGC | 3720 |
| TACGCCAAAG | GTGTCCTAAC | GCAAAACTG | GGGCCTTGGC | GTCGGCCGGT | GGCCTACCTG | 3780 |
| TCCAAAAAGC | TAGACCCAGT | GGCAGCTGGG | TGGCCCCCTT | GCCTACGGAT | GGTAGCAGCC | 3840 |
| ATCGCCGTTC | TGACCAAAGA | CGCTGGCAAG | CTCACCATGG | GACAGCCACT | AGTCATTCTG | 3900 |
| GCCCCCCATG | CAGTAGAGGC | ACTAGTTAAG | CAACCCCCTG | ATCGCTGGCT | CTCCAACGCC | 3960 |
| CGAATGACCC | ACTACCAGGC | TCTGCTTCTG | GACACGGACC | GAGTCCAGTT | CGGACCAATA | 4020 |
| GTGGCCCTAA | ACCCAGCTAC | GCTGCTCCCT | CTACCTGAGG | AGGGGCTGCA | ACATGACTGC | 4080 |
| CTTGACATCT | TGGCTGAAGC | CCACGGAACT | AGACCAGATC | TTACGGACCA | GCCTCTCCCA | 4140 |
| GACGCTGACC | ACACCTGGTA | CACAGATGGG | AGCAGCTTCC | TGCAAGAGGG | GCAGCGCAAG | 4200 |
| GCCGGAGCAG | CAGTAACCAC | CGAGACCGAG | GTAGTCTGGG | CCAAAGCACT | GCCAGCCGGG | 4260 |
| ACATCGGCCC | AAAGAGCTGA | GTTGATAGCG | CTCACCCAAG | CCTTAAAAAT | GGCAGAAGGT | 4320 |
| AAGAAGCTGA | ATGTTTACAC | CGATAGCCGT | TATGCTTTTG | CCACTGCCCA | TATTCACGGA | 4380 |
| GAAATATATA | GAAGGCGCGG | GTTGCTCACA | TCAGAAGGAA | AAGAAATCAA | AATAAGGAC | 4440 |
| GAGATCTTGG | CCCTACTGAA | GGCTCTCTTC | CTGCCCAAAA | GACTTAGCAT | AATTCATTGC | 4500 |
| CCGGGACATC | AGAAGGGAAA | CCGCGCGGAG | GCAAGGGCA | ACAGGATGGC | CGACCAAGCG | 4560 |
| GCCCGAGAAG | TAGCCACTAG | AGAAACTCCA | GAGACTTCCA | CACTTCTGAT | AGAAAATTCA | 4620 |
| GCCCCCTATA | CTCATGAACA | TTTTCACTAT | ACGGTGACTG | ACATAAAGA | TCTGACTAAA | 4680 |
| CTAGGGGCCA | CTTATGACGA | TGCAAAGAAG | TGTTGGGTTT | ATCAGGGAAA | GCCTGTAATG | 4740 |
| CCTGATCAAT | TCACCTTTGA | ACTATTAGAT | TTTCTTCATC | AATTGACCCA | CCTCAGTTTC | 4800 |
| TCAAAAACAA | AGGCTCTTCT | AGAAAGGAAC | TACTGTCCTT | ATTACATGCT | GAACCGGGAT | 4860 |
| CGAACGCTCA | AAGACATCAC | TGAGACTTGC | CAAGCCTGTG | CACAGGTCAA | TGCCAGCAAG | 4920 |
| TCTGCCGTCA | AACAAGGGAC | TAGAGTTCGA | GGGCACCGAC | CCGGCACCCA | CTGGGAAATT | 4980 |
| GATTTCACTG | AGGTAAAACC | TGGCCTGTAT | GGGTATAAAT | ATCTTTTAGT | TTTCATAGAC | 5040 |
| ACTTTCTCTG | GATGGGTAGA | AGCTTTCCCA | ACCAAGAAAG | AAACTGCCAA | AGTTGTAACC | 5100 |
| AAGAAGCTAC | TAGAAGAAAT | CTTCCCCAGA | TTCGGCATGC | CACAGGTATT | GGGAACCGAC | 5160 |
| AATGGGCCTG | CCTTCGTCTC | CAAGGTAAGT | CAGACAGTAG | CCGATTTACT | GGGGGTTGAT | 5220 |
| TGGAAACTAC | ATTGTGCTTA | CAGACCCCAG | AGTTCAGGTC | AGGTAGAAAG | AATGAATAGG | 5280 |
| ACAATCAAGG | AGACTTTAAC | TAAATTGACG | CTTGCAACTG | GCTCTAGGGA | CTGGGTGCTC | 5340 |
| CTGCTTCCCC | TAGCCCTGTA | TCGAGCCCGC | AACACGCCGG | GCCCCATGG | TCTCACCCCA | 5400 |
| TATGAAATCT | TATATGGGGC | ACCCCCGCCC | CTTGTAAACT | TCCCTGATCC | TGACATGGCA | 5460 |
| AAGGTTACTC | ATAACCCCTC | TCTCCAAGCC | CATTTACAGG | CACTCTACCT | GGTCCAGCAC | 5520 |
| GAAGTCTGGA | GACCGTTGGC | GGCAGCTTAC | CAAGAACAAC | TGGACCGGCC | GGTAGTGCCT | 5580 |
| CACCCTTTCC | GAGTCGGTGA | CACAGTGTGG | GTCCGCAGAC | ACCAAACTAA | AAATCTAGAA | 5640 |
| CCCCGCTGGA | AAGGACCTTA | TACCGTCCTA | CTGACTACCC | CCACCGCTCT | CAAAGTGGAC | 5700 |
| GGCATTGCAG | CGTGGATCCA | CGCTGCCCAC | GTAAAGGCTG | CCGACACCAG | GATTGAGCCA | 5760 |
| CCATCGGAAT | CGACATGGCG | TGTTCAACGC | TCTCAAAATC | CCCTAAAGAT | AAGATTGACC | 5820 |

```
CGCGGGACCT CCTAATCCCC TTAATTCTCT TCCTGTCTCT CAAAGGGGCC AGATCCGCAG    5880
CACCCGGCTC CAGCCCTCAC CAGGTCTACA ACATTACCTG GGAAGTGACC AATGGGGATC    5940
GGGAGACAGT ATGGGCAATA TCAGGCAACC ACCCTCTGTG GACTTGGTGG CCAGTCCTCA    6000
CCCCAGATTT GTGTATGTTA GCTCTCAGTG GGCCGCCCCA CTGGGGGCTA GAGTATCAGG    6060
CCCCCTATTC CTCGCCCCCG GGGCCCCCTT GTTGCTCAGG GAGCAGCGGG AACGTTGCAG    6120
GCTGTGCCAG AGACTGCAAC GAGCCCTTGA CCTCCCTCAC CCCTCGGTGC AACACTGCCT    6180
GGAACAGACT TAAGCTGGAC CAGGTAACTC ATAAATCAAG TGAGGGATTT TATGTCTGCC    6240
CCGGGTCACA TCGCCCCGG GAAGCCAAGT CCTGTGGGGG TCCAGACTCC TTCTACTGTG     6300
CCTCTTGGGG CTGCGAGACA ACCGGTAGAG TATACTGGAA GCCCTCCTCT TCTTGGGACT    6360
ACATCACAGT AGACAACAAT CTCACCTCTA ACCAGGCTGT TCAGGTATGC AAAGACAATA    6420
AGTGGTGCAA TCCCTTGGCT ATCCGGTTTA CAAACGCCGG GAAACAGGTC ACCTCATGGA    6480
CAACTGGACA CTATTGGGGT CTACGTCTTT ATGTCTCTGG ACAGGACCCA GGGCTTACTT    6540
TCGGGATCCG ACTCAGTTAT CAAAATCTAG GACCTCGGAT CCAATAGGA CCAAACCCCG     6600
TCCTGGCAGA CCAACTTTCG TTCCCGCTAC CTAATCCCCT ACCCAAACCT GCCAAGTCTC    6660
CCCCCGCCTC TAGTTCGACT CCCACATTGA TTTCCCCGTC CCCCACTCCC ACTCAGCCCC    6720
CGCCAGCAGG AACGGGAGAC AGATTACTAA ATCTAGTACA GGGAGCTTAC CAGGCACTCA    6780
ACCTTACCAA CCCTGATAAA ACTCAAGAGT GCTGGTTATG CCTAGTGTCT GGACCCCCT     6840
ATTACGAGGG GGTTGCCGTC CTAGGTACTT ATTCCAACCA TACCTCTGCC CCAGCTAACT    6900
GCTCCGTGGC CTCCCAACAC AAGCTGACCC TGTCCGAAGT GACTGGACGG GACTCTGCA    6960
TAGGAACAGT CCCAAAAACT CACCAGGCCC TGTGCAACAC TACCCTTAAG GCAGGCAAAG    7020
GGTCTTACTA TCTAGTTGCC CCCACAGGAA CTATGTGGGC ATGTAACACT GGACTCACTC    7080
CATGCCTATC TGCCACCGTG CTTAATCGCA CCACTGACTA TTGCGTTCTC GTGGAATTAT    7140
GGCCCAGGGT CACCTACCAT CCTCCCAGTT ACGTCTATAG CCAGTTTGAA AAATCCCATA    7200
GACATAAAAG AGAACCAGTG TCCTTAACCT TGGCCTTATT ATTAGGTGGG CTAACTATGG    7260
GTGGCATCGC CGCGGGAGTA GGGACAGGAA CTACCGCCCT GGTCGCCACC AGCAGTTTC    7320
AGCAGCTCCA TGCTGCCGTA CAAGATGATC TCAAAGAAGT CGAAAAGTCA ATTACTAACC    7380
TAGAAAAGTC TCTTACTTCG TTGTCTGAGG TTGTACTGCA GAATCGACGA GGCCTAGACC    7440
TGTTGTTCCT AAAAGAGGGA GGACTGTGTG CTGCCCTAAA AGAAGAATGT TGTTTCTATG    7500
CTGACCATAC AGGCCTAGTA AGAGATAGTA TGGCCAAATT AAGAGAGAGA CTCTCTCAGA    7560
GACAAAAACT ATTTGAGTCG AGCCAAGGAT GGTTCGAAGG ATGGTTTAAC AGATCCCCT     7620
GGTTTACCAC GTTGATATCC ACCATCATGG GGCCTCTCAT TATACTCCTA CTAATTCTGC    7680
TTTTTGGACC CTGCATTCTT AATCGATTAG TTCAATTTGT TAAAGACAGG ATCTCAGTAG    7740
TCCAGGCTTT AGTCCTGACT CAACAATACC ACCAGCTAAA ACCACTAGAA TACGAGCCAC    7800
AATAAATAAA AGATTTTATT TAGTTTCCAG AAAAAGGGGG GAATGAAAGA CCCCACCAAA    7860
TTGCTTAGCC TGATAGCCGC AGTAACGCCA TTTTGCAAGG CATGGAAAAA TACCAAACCA    7920
AGAATAGAGA AGTTCAGATC AAGGGCGGGT ACACGAAAAC AGCTAACGTT GGGCCAAACA    7980
GGATATCTGC GGTGAGCAGT TTCGGCCCCG GCCCGGGGCC AAGAACAGAT GGTCACCGCG    8040
GTTCGGCCCC GGCCCGGGGC CAAGAACAGA TGGTCCCCAG ATATGGCCCA ACCCTCAGCA    8100
GTTTCTTAAG ACCCATCAGA TGTTTCCAGG CTCCCCCAAG GACCTGAAAT GACCCTGTGC    8160
CTTATTTGAA TTAACCAATC AGCCTGCTTC TCGCTTCTGT TCGCGCGCTT CTGCTTCCCG    8220
```

| | | | | | | |
|---|---|---|---|---|---|---|
| AGCTCTATAA | AAGAGCTCAC | AACCCCTCAC | TCGGCGCGCC | AGTCCTCCGA | TAGACTGAGT | 8280 |
| CGCCCGGGTA | CCCGTGTATC | CAATAAATCC | TCTTGCTGTT | GCA | | 8323 |

( 2 ) INFORMATION FOR SEQ ID NO:9:

( i ) SEQUENCE CHARACTERISTICS:
        ( A ) LENGTH: 10367 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

| | | | | | | |
|---|---|---|---|---|---|---|
| GAACTCGAGC | AGGGCTAGTA | CAGACACAGG | CGCATAAAAT | CAATCAAAGA | CACAGGACAA | 60 |
| TGGACAGACA | CAGAACAATT | GCTGGCCAGC | TTACCTCCCG | GTGGTGGGTC | GGTGGTCCCT | 120 |
| GGGCAGGGGT | CTCCAGATCC | CGGACGAGCC | CCCAAATGAA | AGACCCCGA | GACGGGTAGT | 180 |
| CAATCACTCT | GAGGAGACCC | TCCCAAGGAA | CAGCGAGACC | ACGAGTCGGA | TGCAACAGCA | 240 |
| AGAGGATTTA | TTGGATACAC | GGGTACCCGG | GCGACTCAGT | CTATCGGAGG | ACTGGCGCGC | 300 |
| CGAGTGAGGG | GTTGTGAGCT | CTTTTATAGA | GCTCGGGAAG | CAGAAGCGCG | CGAACAGAAG | 360 |
| CGAGAAGCAG | GCTGATTGGT | TAATTCAAAT | AAGGCACAGG | GTCATTTCAG | GTCCTTGGGG | 420 |
| GAGCCTGGAA | ACATCTGATG | GGTCTTAAGA | AACTGCTGAG | GGTTGGGCCA | TATCTGGGA | 480 |
| CCATCTGTTC | TTGGCCCCGG | GCCGGGGCCG | AACCGCGGTG | ACCATCTGTT | CTTGGCCCCG | 540 |
| GGCCGGGGCC | GAAACTGCTC | ACCGCAGATA | TCCTGTTTGG | CCCAACGTTA | GCTGTTTTCG | 600 |
| TGTACCCGCC | CTTGATCTGA | ACTTCTCTAT | TCTTGGTTTG | GTATTTTCC | ATGCCTTGCA | 660 |
| AAATGGCGTT | ACTGCGGCTA | TCAGGCTAAG | CAACTTGGTG | GGGTCTTTCA | TTCCCCCCTT | 720 |
| TTTCTGGAAA | CTAAATAAAA | TCTTTTATTT | ATCATGGCTC | GTATTCTAGT | GGTTTTAGCT | 780 |
| GGTGGTATTG | TTGAGTCAGG | ACTAAAGCCT | GGACTACTGA | GATCCTGTCT | TTAACAAATT | 840 |
| GAACTAATCG | ATTCATTAGC | TAGCTCCTGC | TGGCGGGGGC | TGAGTGGGAG | TGGGGGACGG | 900 |
| GGAAATCAAT | GTGGGAGTCG | AATTAGAGGC | GGGGGGAGAC | TTGGCAGGTT | TGGGTAGGGG | 960 |
| ATTAGGTCGC | GGGAGCGAAA | GTTGGTCTGC | CAGGACGGGG | TTCGGTCCTA | TCGGGACCCG | 1020 |
| AGGTCCTAGA | TTTTGATATC | TGAGTCGGAT | CCCGAAAGTA | AGCCCGGGT | CCCGCCCAGA | 1080 |
| GACATAAAGA | CGTAGACCCC | AATAGTGTCC | AGTTGTCCAT | GAGGTGACCT | GTTTCCCGGC | 1140 |
| GTTTGTAAAC | TGGATAGCCA | AGGGATTGCA | CCACTTATTG | TCTTTGCATA | CCTGGACAGC | 1200 |
| CTGGCTAGTG | GTGAGATTGT | TGTCCACTGT | GATGTAGTCC | CAAGAGGAGG | AGGGCTTCCA | 1260 |
| GTATACTCTA | CCGGTTGTCT | CGCAGCCCCA | AGAGGCACAG | TAGAAGGAGT | CTGGACCTCC | 1320 |
| ACAGGACTTG | GCTTCCCGGG | GGCGATGTGA | CCCGGGGCAG | ACATAAAATC | CCTCACTTGA | 1380 |
| TTTATGAGTT | ACCTGGTCTA | GCTTAAGTCT | GTTCCAGGCA | GTGTTGCACC | GAGGGGTGAG | 1440 |
| GGAGGTCAAG | GGCTCGTCGC | AGTCTCTGGA | ACAGCCTGCA | CTGCTCCCGC | TGCTCCCTGA | 1500 |
| GCAACAAGGG | GGCCCCGGGG | GCGAGGAATA | GGGGGCCTGA | TACTCTAGCC | CCCAGTGGGG | 1560 |
| CGGCCCACTG | AGAGCTAACA | TACACAAATC | TGGGGTGAGG | ACTGGCCACC | AAGTCCACAG | 1620 |
| AGGGTGGTTG | CCTGATATTG | CCCATACTGT | CTCCCGATCC | CCATTGGTCA | CTTCCCAGGT | 1680 |
| AATGTTGTAG | ACCTGGTGAG | GGCTGGAGCC | GGGTGCTGCG | GATCTGGCCC | CTTTGAGAGA | 1740 |
| CAGGAAGAGA | ATTAAGGGGA | TTAGGAGGTC | CCGCGGGTCA | ATCTTATCTT | TAGGGGATTT | 1800 |

| | | | | | |
|---|---|---|---|---|---|
| TGGGAGCGTT | GAACACGCCA | TGTCGATTCT | GCTGGTGGCT | CAATCCTGGT | GTCGGCAGCC | 1860 |
| TTTACGTGGG | CAGCGTGGAT | CCACGCTGCA | ATGCCGTCTA | CTTTGAGAGC | GGTGGGGGTA | 1920 |
| GTCAGTAGGA | CGGTATAGGG | TCCTTTCCAG | CGGGGTTCTA | GATTTTTAGT | TTGGTGTCTG | 1980 |
| CGGACCCACA | CTGTGTCACC | GACCCGGAAA | GGGTGAGGTA | CTACCGGCCG | GTCTAGTTGC | 2040 |
| TCTTGGTAAG | CTGCCGCCAA | CGGTCTCCAG | ACTTCGTGCT | GGACCAGGTA | GAGTGCCTGT | 2100 |
| AAATGAGCTT | GGAGAGAGGG | GTTATGAGTA | ACCTTTGCCA | TGTCAGGATC | AGGGAAGTTT | 2160 |
| ACAAGGGGCG | GGGGTGCCCC | ATATAAGATT | TCATATGGGG | TGAGACCGTG | GGGCCCGGC | 2220 |
| GTGTTGCGGG | CTCGATACAG | GGCAAGGGA | AGCAGGAGCA | CCCAGTCCCT | AGAGCCAGTT | 2280 |
| GCAAGCGTCA | ATTTAGTTAA | AGTCTCCTTG | ATTGTCCTAT | TCATTCTTTC | TACCTGACCT | 2340 |
| GAACTCTGGG | GTCTGTAAGC | ACAATGTAGT | TTCCAATCAA | CCCCCAATAA | ATCGGCTACT | 2400 |
| GTCTGACTTA | CCTTGGAGAC | GAAGGCAGGC | CCATTGTCGG | TTCCCAATAC | CTGTGGCATG | 2460 |
| CCGAATCTGG | GGAAGATTTC | TTCTAGTAGC | TTCTTGGTTA | CAACTTTGGC | AGTTTCTTTC | 2520 |
| TTGGTTGGGA | AAGCTTCTAC | CCATCCAGAG | AAAGTGTCTA | TGAAAACTAA | AAGATATTTA | 2580 |
| TACCCATACA | GGCCAGGTTT | TACCTCAGTG | AAATCAATTT | CCCAGTGGGT | GCCGGGTCGG | 2640 |
| TGCCCTCGAA | CTCTAGTCCC | TTGTTTGACG | GCAGACTTGC | TGGCATTGAC | CTGTGCACAG | 2700 |
| GCTTGGCAAG | TCTCAGTGAT | GTCTTTGAGC | GTTCGATCCC | GGTTCAGCAT | GTAATAAGGA | 2760 |
| CAGTAGTTCC | TTTCTAGAAG | AGCCTTTGTT | TTTGAGAAAC | TGAGGTGGGT | CAATTGATGA | 2820 |
| AGAAAATCTA | ATAGTTCAAA | GGTGAATTGA | TCAGGCATTA | CAGGCTTTCC | CTGATAAACC | 2880 |
| CAACACTTCT | TTGCATCGTC | ATAAGTGGCC | CCTAGTTTAG | TCAGATCTTT | TATGTCAGTC | 2940 |
| ACCGTATAGT | GAAAATGTTC | ATGAGTATAG | GGGGCTGAAT | TTTCTATCAG | AAGTGTGGAA | 3000 |
| GTCTCTGGAG | TTTCTCTAGT | GGCTACTTCT | CGGGCCGCTT | GGTCGGCCAT | CCTGTTGCCC | 3060 |
| CTTGCCTCCG | CGCGGTTTCC | CTTCTGATGT | CCCGGGCAAT | GAATTATGCT | AAGTCTTTTG | 3120 |
| GGCAGGAAGA | GAGCCTTCAG | TAGGGCCAAG | ATCTCGTCCT | TATTTTGAT | TTCTTTTCCT | 3180 |
| TCTGATGTGA | GCAACCCGCG | CCTTCTATAT | ATTTCTCCGT | GAATATGGGC | AGTGGCAAAA | 3240 |
| GCATAACGGC | TATCGGTGTA | AACATTCAGC | TTCTTACCTT | CTGCCATTTT | TAAGGCTTGG | 3300 |
| GTGAGCGCTA | TCAACTCAGC | TCTTTGGGCC | GATGTCCCGG | CTGGCAGTGC | TTTGGCCAG | 3360 |
| ACTACCTCGG | TCTCGGTGGT | TACTGCTGCT | CCGGCCTTGC | GCTGCCCCTC | TTGCAGGAAG | 3420 |
| CTGCTCCCAT | CTGTGTACCA | GGTGTGGTCA | GCGTCTGGGA | GAGGCTGGTC | CGTAAGATCT | 3480 |
| GGTCTAGTTC | CGTGGGCTTC | AGCCAAGATG | TCAAGGCAGT | CATGTTGCAG | CCCCTCCTCA | 3540 |
| GGTAGAGGGA | GCAGCGTAGC | TGGGTTTAGG | GCCACTATTG | GTCCGAACTG | GACTCGGTCC | 3600 |
| GTGTCCAGAA | GCAGAGCCTG | GTAGTGGGTC | ATTCGGGCGT | TGGAGAGCCA | GCGATCAGGG | 3660 |
| GGTTGCTTAA | CTAGTGCCTC | TACTGCATGG | GGGGCCAGAA | TGACTAGTGG | CTGTCCCATG | 3720 |
| GTGAGCTTGC | CAGCGTCTTT | GGTCAGAACG | GCGATGGCTG | CTACCATCCG | TAGGCAAGGG | 3780 |
| GGCCACCCAG | CTGCCACTGG | GTCTAGCTTT | TTGGACAGGT | AGGCCACCGG | CCGACGCCAA | 3840 |
| GGCCCCAGTT | TTTGCGTTAG | GACACCTTTG | GCGTAGCCCT | GCTTCTCGTC | AACAAAAAGT | 3900 |
| TCGAAGGGCT | TAGTCAAGTC | TGGCAATCCC | AGGGCAGGGG | CAGTTAAGAG | AGCCTGCTTG | 3960 |
| ATCTCTTGGT | AGGCCTTTTG | CTGGTCTGGG | CCCCACTCAA | ACAGAGTCCC | CGTTTGGTG | 4020 |
| AGAGGGTACA | AGGGGGCTGC | CATTTCTGCA | AACCCAGGGA | TCCAGAGGCG | ACAGAAGCCT | 4080 |
| GCCGTCCCTA | GGAACTCCCT | TAGTTGTCGA | GGGGTCTTCG | GAGTAGGCTG | CCCCATCACA | 4140 |
| GTCTCTTTTC | TGGCCTCAGT | CAGCCATCTC | TGACCCTCTT | TTAGAAGATA | CCCCAGATAC | 4200 |

| | | | | | |
|---|---|---|---|---|---|
| TTGACCTGTT | TCTGGCAAAT | TTGGGCTTTC | TTGGCCGAGG | CCCGATATCC | GAGGTCCCCT | 4260
| AGGGTTTGTA | ACAGGGCCCG | CGTACCTTGT | TGACAGTCAA | GCTCAGAAGT | GGCGGCCAGC | 4320
| AGTAAGTCAT | CTACATACTG | GAGCAGAATC | AGGTCTGGGT | GCTGGATCCG | GAAGTCTGCG | 4380
| AGGTCCCTGT | GCAGGGCTTC | ATCAAACAGG | GTGGGACTGT | TTTTGAAACC | CTGCGGGAGT | 4440
| CTGGTCCAGG | TTAATTGTCC | TGAGATTCCC | ATCTCTGGAT | CTCTCCACTC | AAAGGCGAAG | 4500
| AGAGACTGAC | TGGTGGGGTG | GAGTCTCAGG | CAGAAAAAG | CATCTTTTAA | GTCAAGCACA | 4560
| GTGTACCACT | GGTGGGACGG | TGGGAGCCCG | CTCAAGAGGT | TGTAAGGGTT | GGGCACGGTG | 4620
| GGGTGGATGT | CTTCCACCCG | CTTGTTGACT | TCTCTCAGAT | CCTGGACAGG | CCTATAATCA | 4680
| TTAGTCCCCG | GTTTCTTAAC | GGGTAGCAGG | GGCGTGTTCC | AGGGGACTG | GCAGGGTACC | 4740
| AGAATTCCCT | GATCCAGCAG | TCTCTGTATG | TGGGGCTTGA | TCCCCAGTCT | GGCTTCTTGT | 4800
| GACATGGGGT | ATTGTTTTAT | GGACACGGGG | GTAGAGGTTG | CCTTCAGAGG | TATGATCAGA | 4860
| GGAGCTTGGC | GAACGGCCAG | CCCCATGCCC | CCGGTTTCTG | CCCAGGCCTG | GGAAAATCA | 4920
| GAGAGCCATG | TGGACCCTAG | AGGCACATCT | GGCCCTTTTG | AGGTCTCATG | TAGCCGATAC | 4980
| TCATCTTCTA | TGTTTAGGGT | CAGCACTTGC | AGGGGCTGTC | CCATTGGTCC | CACAACCTGA | 5040
| GCTCCTGATC | CCTCAAAGTG | AATTTGGGCT | TTTAGTTTAG | TCAGCAAATC | TCTTCCTAGC | 5100
| AGAGGATAGG | GGCAATCTGG | TACATGGAGG | AAAGAATGGG | TGACCTTACC | GGTGGCTAGG | 5160
| TGCACTCGGC | GATCCGTGGT | CCAGCGATAC | CGCTTCCCTC | CAGTAGCCCC | TTGGACCCAG | 5220
| GCAGACTTGT | CACTTAGGGG | TCCAGGATTT | TGGGTCAGCA | CGGAGTGTTG | GGCCCCAGTA | 5280
| TCCACTAGGA | AGGTGACGGG | TTGCCCCCCG | ACTCTGAGGG | TTATCCTGGG | TTCAGGGGGG | 5340
| GGCTCCTGAC | CCTGACCTCC | CTAATCGTCT | AAGGTCAGGA | GGGAGGCCTG | GGGTCGTGGT | 5400
| CCCCGGGGTC | CTCTTGGCTT | CTTGGGGCAA | TCTCTAGCCC | AATGTCCCTT | TTCTTTGCAG | 5460
| TAGGCACACT | GGTCGTGGTC | GAGTTGGGGC | CTCCTTCGCT | CTCCTCCCTG | TCTATCCTGT | 5520
| CTCTGCCCGC | TAACGACAGT | AGCCAGCAAC | TTACTCATTT | CTCTATGTCT | TCTGCGGTCC | 5580
| CTCTCCTTCT | CTCTCTGCAC | ATCCTCTGCC | CTACGGCGTT | CTTCCTTTTC | CTCTGTTTCT | 5640
| CTCCTAATAC | GTTCCTCTCT | TTCTTCCGGG | GTTTCTCGTT | TATTAAAGAT | CTTTTCAGCT | 5700
| TCCCTCACTA | AGTCTCCTAA | GGTCTTACTC | TTCAAATCTT | CTAACCGCTC | TAACTTTCGC | 5760
| CCGATATCCG | GGGCGGACTG | CCAGATGAAT | GACATGGCCA | CATTGGTTTC | TTGCCCTGGG | 5820
| TCCTCAGGGT | CATAAGGAGT | GTATCTGCGA | TAGGCCTCCT | TGAGTCTCTC | TAAAAAGGCT | 5880
| GAGGGAGACT | CATTAGGTCC | CTGGGTTATC | CCTTTTACCT | TGGCCAAATT | GGTGGGGCTT | 5940
| CTGCCCGCGT | TTTGGAGACC | CGCTAGGAGC | AACTGGCGAT | AGTGGACTAG | GTGGTTCCTA | 6000
| CCTCGTTGGG | TGTTGTAGTC | CCAGTCGGGA | CGTTCCAAGG | GAAAAGCATC | ATTAATGTCA | 6060
| TTGGGCAGCT | GAGTTGGGCG | TCCGTCCTCC | CCTCGAACCG | CCTTTCGGGC | CTCTAGGAGC | 6120
| ACTCGCTGTT | TTTCTTCTCC | CGTCAGCAGG | GTCCCTAATA | GCTGTTGGCA | GTCATCCCAA | 6180
| GTGGGCTGAT | GAGTAAGGAG | AACGGACTCG | ATCAAAGCTG | TCAATTTAGC | TGGGTCCTCG | 6240
| GAGAAAGAGG | GGTTGTTATT | TTTCCAGTTA | TAGAGGTCAG | AGGAGGAAAA | TGGCCAGTAT | 6300
| TGATACTGTC | CATTCCCTCC | CAGGCGAAGG | GGGAACGCCT | GAGAGGTAGT | AGAATCCGCC | 6360
| ACGGGGGTT | CTTTCTTCC | CCGCAGGCGG | GATACCATTG | GGAAGGGTC | AGGGGCTCCT | 6420
| TCTGTAGGGG | CCACTTCTCC | GCTATCGCCG | TTCCCGTCAG | GAGAGGGTGG | CCCTGGGTCC | 6480
| CGGTAAGGCG | GAGGGTCCTC | CGTGAGTAGA | TCAATGAGTG | GTCCTCCGCT | ATCAGGAAGG | 6540
| ACTTGAGGCC | TAGGTTTGGT | GTTTAAAGGA | GAAGTGAGAG | CCGGATAGAG | GGAGGACTGG | 6600

```
GGCGGGGTCG AGAGTGGGGG TTCAGGTGGG AGAGAGGGGG CTGAAGGGGG AAGAGAGAGG   6660
GGAGGTTTAG GGTGCACGAA GGGTCTGACC CAGGGAGGGG GGTCTACTGC TATAGCTTCC   6720
CAGGTCACGA TGTAGGGGAC CTGATCCGGA TGTCCATGTG GGCCAGGTGA AAGACCTTG    6780
ATCTTAACCT GTGTAATAAT GTCTGGGTTA AAAGTGCCGT CTCGTGGCCA TCCGACGTTG   6840
AAGGTTGGCC ATTCTGCAGA GCAGAATGTA ACCCAGCGCC TTTTCTAAC  CTCTACCGAC   6900
AGGTTGTGGG CTGTCCGTTC GACATCCTTC CAGTGGTCTA AAGTCAAACT TAAGGGGGTG   6960
GTAACAGCCT GGCCCATGTT TTCAGACAAA TACAGAAAAA CAGTCAAACA GAGACAACAC   7020
AGAACGATGC TGCAGCAGAC AAGACGCGCG GCGCGGCTTC GGTTCCAAAC CGAAAGCAAA   7080
AACTCAGACG GGGGCGGAAA CCGTTTTAGC CCTCTGTCTC CTACCAGAAC CACATACCCC   7140
TCCTCTAAGG GGGGTGCACC AAAGAGTCCA AAACGATCGG GATGGTTGGA CTCTGGCCGG   7200
GCCACAAAAA TGGCCCCCGA AGTCCCTGGG ACGTCTCCCA GGGTTGCGGC CGGGTGTCTC   7260
GAACTCGTCA GTTCCACCAC GGATCCGCCA GATACCAATC TAGTCGGCCA ACTAGTACAG   7320
ACACAGGCGC ATAAAATCAA TCAAAGACAC AGGACAATGG ACAGACACAG AACAATTGCT   7380
GGCCAGCTTA CCTCCCGGTG GTGGGTCGGT GGTCCCTGGG CAGGGGTCTC CAGATCCCGG   7440
ACGAGCCCCC AAATGAAAGA CCCCCGAGAC GGGTAGTCAA TCACTCTGAG GAGACCCTCC   7500
CAAGGAACAG CGAGACCACG AGTCGGATGC AACAGCAAGA GGATTTATTG GATACACGGG   7560
TACCCGGGCG ACTCAGTCTA TCGGAGGACT GGCGCGCCGA GTGAGGGGTT GTGAGCTCTT   7620
TTATAGAGCT CGGGAAGCAG AAGCGCGCGA ACAGAAGCGA GAAGCAGGCT GATTGGTTAA   7680
TTCAAATAAG GCACAGGGTC ATTTCAGGTC CTTGGGGGAG CCTGGAAACA TCTGATGGGT   7740
CTTAAGAAAC TGCTGAGGGT TGGGCCATAT CTGGGGACCA TCTGTTCTTG GCCCCGGGCC   7800
GGGGCCGAAC CGCGGTGACC ATCTGTTCTT GGCCCCGGGC CGGGGCCGAA ACTGCTCACC   7860
GCAGATATCC TGTTTGGCCC AACGTTAGCT GTTTTCGTGT ACCCGCCCTT GATCTGAACT   7920
TCTCTATTCT TGGTTTGGTA TTTTTCCATG CCTTGCAAAA TGGCGTTACT GCGGCTATCA   7980
GGCTAAATCA GATCTGCCGG TCTCCCTATA GTGAGTCGTA TTAATTTCGA TAAGCCAGGT   8040
TAACCTGCAT TAATGAATCG GCCAACGCGC GGGGAGAGGC GGTTTGCGTA TTGGGCGCTC   8100
TTCCGCTTCC TCGCTCACTG ACTCGCTGCG CTCGGTCGTT CGGCTGCGGC GAGCGGTATC   8160
AGCTCACTCA AAGGCGGTAA TACGGTTATC CACAGAATCA GGGGATAACG CAGGAAAGAA   8220
CATGTGAGCA AAAGGCCAGC AAAAGGCCAG GAACCGTAAA AAGGCCGCGT TGCTGGCGTT   8280
TTTCCATAGG CTCCGCCCCC CTGACGAGCA TCACAAAAAT CGACGCTCAA GTCAGAGGTG   8340
GCGAAACCCG ACAGGACTAT AAAGATACCA GGCGTTTCCC CCTGGAAGCT CCCTCGTGCG   8400
CTCTCCTGTT CCGACCCTGC CGCTTACCGG ATACCTGTCC GCCTTTCTCC CTTCGGGAAG   8460
CGTGGCGCTT TCTCAATGCT CACGCTGTAG GTATCTCAGT TCGGTGTAGG TCGTTCGCTC   8520
CAAGCTGGGC TGTGTGCACG AACCCCCCGT TCAGCCCGAC CGCTGCGCCT TATCCGGTAA   8580
CTATCGTCTT GAGTCCAACC CGGTAAGACA CGACTTATCG CCACTGGCAG CAGCCACTGG   8640
TAACAGGATT AGCAGAGCGA GGTATGTAGG CGGTGCTACA GAGTTCTTGA AGTGGTGGCC   8700
TAACTACGGC TACACTAGAA GGACAGTATT TGGTATCTGC GCTCTGCTGA AGCCAGTTAC   8760
CTTCGGAAAA AGAGTTGGTA GCTCTTGATC CGGCAAACAA ACCACCGCTG GTAGCGGTGG   8820
TTTTTTTGTT TGCAAGCAGC AGATTACGCG CAGAAAAAAA GGATCTCAAG AAGATCCTTT   8880
GATCTTTTCT ACGGGGTCTG ACGCTCAGTG GAACGAAAAC TCACGTTAAG GGATTTTGGT   8940
CATGAGATTA TCAAAAAGGA TCTTCACCTA GATCCTTTTA AATTAAAAAT GAAGTTTTAA   9000
```

-continued

| | | | | | |
|---|---|---|---|---|---|
| ATCAATCTAA | AGTATATATG | AGTAAACTTG | GTCTGACAGT | TACCAATGCT | TAATCAGTGA | 9060 |
| GGCACCTATC | TCAGCGATCT | GTCTATTTCG | TTCATCCATA | GTTGCCTGAC | TCCCCGTCGT | 9120 |
| GTAGATAACT | ACGATACGGG | AGGGCTTACC | ATCTGGCCCC | AGTGCTGCAA | TGATACCGCG | 9180 |
| AGACCCACGC | TCACCGGCTC | CAGATTTATC | AGCAATAAAC | CAGCCAGCCG | GAAGGGCCGA | 9240 |
| GCGCAGAAGT | GGTCCTGCAA | CTTTATCCGC | CTCCATCCAG | TCTATTAATT | GTTGCCGGGA | 9300 |
| AGCTAGAGTA | AGTAGTTCGC | CAGTTAATAG | TTTGCGCAAC | GTTGTTGCCA | TTGCTACAGG | 9360 |
| CATCGTGGTG | TCACGCTCGT | CGTTTGGTAT | GGCTTCATTC | AGCTCCGGTT | CCCAACGATC | 9420 |
| AAGGCGAGTT | ACATGATCCC | CCATGTTGTG | CAAAAAGCG | GTTAGCTCCT | TCGGTCCTCC | 9480 |
| GATCGTTGTC | AGAAGTAAGT | TGGCCGCAGT | GTTATCACTC | ATGGTTATGG | CAGCACTGCA | 9540 |
| TAATTCTCTT | ACTGTCATGC | CATCCGTAAG | ATGCTTTCT | GTGACTGGTG | AGTACTCAAC | 9600 |
| CAAGTCATTC | TGAGAATAGT | GTATGCGGCG | ACCGAGTTGC | TCTTGCCCGG | CGTCAATACG | 9660 |
| GGATAATACC | GCGCCACATA | GCAGAACTTT | AAAAGTGCTC | ATCATTGGAA | AACGTTCTTC | 9720 |
| GGGGCGAAAA | CTCTCAAGGA | TCTTACCGCT | GTTGAGATCC | AGTTCGATGT | AACCCACTCG | 9780 |
| TGCACCCAAC | TGATCTTCAG | CATCTTTTAC | TTTCACCAGC | GTTTCTGGGT | GAGCAAAAAC | 9840 |
| AGGAAGGCAA | AATGCCGCAA | AAAAGGGAAT | AAGGGCGACA | CGGAAATGTT | GAATACTCAT | 9900 |
| ACTCTTCCTT | TTTCAATATT | ATTGAAGCAT | TTATCAGGGT | TATTGTCTCA | TGAGCGGATA | 9960 |
| CATATTTGAA | TGTATTTAGA | AAAATAAACA | AATAGGGGTT | CCGCGCACAT | TTCCCCGAAA | 10020 |
| AGTGCCACCT | GACGTCTAAG | AAACCATTAT | TATCATGACA | TTAACCTATA | AAAATAGGCG | 10080 |
| TATCACGAGG | CCCTTTCGTC | TCGCGCGTTT | CGGTGATGAC | GGTGAAAACC | TCTGACACAT | 10140 |
| GCAGCTCCCG | GAGACGGTCA | CAGCTTGTCT | GTAAGCGGAT | GCCGGGAGCA | GACAAGCCCG | 10200 |
| TCAGGGCGCG | TCAGCGGGTG | TTGGCGGGTG | TCGGGCTGG | CTTAACTATG | CGGCATCAGA | 10260 |
| GCAGATTGTA | CTGAGAGTGC | ACCATATGGA | CATATTGTCG | TTAGAACGCG | GCTACAATTA | 10320 |
| ATACATAACC | TTATGTATCA | TACACATACG | ATTTAGGTGA | CACTATA | | 10367 |

( 2 ) INFORMATION FOR SEQ ID NO:10:

( i ) SEQUENCE CHARACTERISTICS:
( A ) LENGTH: 323 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( x i ) SEQUENCE DESCRIPTION: SEQ ID NO:10:

```
Met Ala Cys Ser Thr Leu Pro Lys Ser Pro Lys Asp Lys Ile Asp Pro
 1               5                  10                  15

Arg Asp Leu Leu Ile Pro Leu Ile Leu Phe Leu Ser Leu Lys Gly Ala
             20                  25                  30

Arg Ser Ala Ala Pro Gly Ser Ser Pro His Gln Val Tyr Asn Ile Thr
                 35                  40                  45

Trp Glu Val Thr Asn Gly Asp Arg Glu Thr Val Trp Ala Ile Ser Gly
     50                  55                  60

Asn His Pro Leu Trp Thr Trp Trp Pro Val Leu Thr Pro Asp Leu Cys
 65                  70                  75                  80

Met Leu Ala Leu Ser Gly Pro Pro His Trp Gly Leu Glu Tyr Gln Ala
                         85                  90                  95
```

```
Pro  Tyr  Ser  Ser  Pro  Pro  Gly  Pro  Pro  Cys  Cys  Ser  Gly  Ser  Ser  Gly
          100            105                           110

Ser  Ser  Ala  Gly  Cys  Ser  Arg  Asp  Cys  Asp  Glu  Pro  Leu  Thr  Ser  Leu
          115                      120                      125

Thr  Pro  Arg  Cys  Asn  Thr  Ala  Trp  Asn  Arg  Leu  Lys  Leu  Asp  Gln  Val
     130                 135                      140

Thr  His  Lys  Ser  Ser  Glu  Gly  Phe  Tyr  Val  Cys  Pro  Gly  Ser  His  Arg
145                      150                 155                           160

Pro  Arg  Glu  Ala  Lys  Ser  Cys  Gly  Gly  Pro  Asp  Ser  Phe  Tyr  Cys  Ala
               165                      170                           175

Ser  Trp  Gly  Cys  Glu  Thr  Thr  Gly  Arg  Val  Tyr  Trp  Lys  Pro  Ser  Ser
          180                      185                      190

Ser  Trp  Asp  Tyr  Ile  Thr  Val  Asp  Asn  Asn  Leu  Thr  Thr  Ser  Gln  Ala
          195                 200                      205

Val  Gln  Val  Cys  Lys  Asp  Asn  Lys  Trp  Cys  Asn  Pro  Leu  Ala  Ile  Gln
     210                 215                      220

Phe  Thr  Asn  Ala  Gly  Lys  Gln  Val  Thr  Ser  Trp  Thr  Thr  Gly  His  Tyr
225                      230                      235                      240

Trp  Gly  Leu  Arg  Leu  Tyr  Val  Ser  Gly  Arg  Asp  Pro  Gly  Leu  Thr  Phe
               245                      250                      255

Gly  Ile  Arg  Leu  Arg  Tyr  Gln  Asn  Leu  Gly  Pro  Arg  Val  Pro  Ile  Gly
               260                 265                      270

Pro  Asn  Pro  Val  Leu  Ala  Asp  Gln  Leu  Ser  Leu  Pro  Arg  Pro  Asn  Pro
          275                 280                      285

Leu  Pro  Lys  Pro  Ala  Lys  Ser  Pro  Pro  Ala  Ser  Asn  Ser  Thr  Pro  Thr
     290                 295                      300

Leu  Ile  Ser  Pro  Ser  Pro  Thr  Pro  Thr  Gln  Pro  Pro  Pro  Ala  Gly  Ala
305                      310                 315                           320

Ser  Glx  Glx
```

(2) INFORMATION FOR SEQ ID NO:11:

(i) SEQUENCE CHARACTERISTICS:
        (A) LENGTH: 289 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:11:

```
Ala  Ala  Pro  Gly  Ser  Ser  Pro  His  Gln  Val  Tyr  Asn  Ile  Thr  Trp  Glu
1              5                      10                      15

Val  Thr  Asn  Gly  Asp  Arg  Glu  Thr  Val  Trp  Ala  Ile  Ser  Gly  Asn  His
          20                      25                      30

Pro  Leu  Trp  Thr  Trp  Trp  Pro  Val  Leu  Thr  Pro  Asp  Leu  Cys  Met  Leu
          35                 40                      45

Ala  Leu  Ser  Gly  Pro  Pro  His  Trp  Gly  Leu  Glu  Tyr  Gln  Ala  Pro  Tyr
     50                      55                      60

Ser  Ser  Pro  Pro  Gly  Pro  Pro  Cys  Cys  Ser  Gly  Ser  Ser  Gly  Ser  Ser
65                      70                      75                      80

Ala  Gly  Cys  Ser  Arg  Asp  Cys  Asp  Glu  Pro  Leu  Thr  Ser  Leu  Thr  Pro
               85                      90                      95

Arg  Cys  Asn  Thr  Ala  Trp  Asn  Arg  Leu  Lys  Leu  Asp  Gln  Val  Thr  His
               100                     105                     110
```

|     |     |     |     |     |     |     |     |     |     |     |     |     |     |     |
|-----|-----|-----|-----|-----|-----|-----|-----|-----|-----|-----|-----|-----|-----|-----|
| Lys | Ser | Ser<br>115 | Glu | Gly | Phe | Tyr | Val<br>120 | Cys | Pro | Gly | Ser | His<br>125 | Arg | Pro | Arg |
| Glu | Ala<br>130 | Lys | Ser | Cys | Gly<br>135 | Gly | Pro | Asp | Ser | Phe<br>140 | Tyr | Cys | Ala | Ser | Trp |
| Gly<br>145 | Cys | Glu | Thr | Thr | Gly<br>150 | Arg | Val | Tyr | Trp | Lys<br>155 | Pro | Ser | Ser | Ser | Trp<br>160 |
| Asp | Tyr | Ile | Thr | Val<br>165 | Asp | Asn | Asn | Leu | Thr<br>170 | Thr | Ser | Gln | Ala | Val<br>175 | Gln |
| Val | Cys | Lys | Asp<br>180 | Asn | Lys | Trp | Cys | Asn<br>185 | Pro | Leu | Ala | Ile | Gln<br>190 | Phe | Thr |
| Asn | Ala | Gly<br>195 | Lys | Gln | Val | Thr | Ser<br>200 | Trp | Thr | Thr | Gly | His<br>205 | Tyr | Trp | Gly |
| Leu | Arg<br>210 | Leu | Tyr | Val | Ser | Gly<br>215 | Arg | Asp | Pro | Gly | Leu<br>220 | Thr | Phe | Gly | Ile |
| Arg<br>225 | Leu | Arg | Tyr | Gln | Asn<br>230 | Leu | Gly | Pro | Arg | Val<br>235 | Pro | Ile | Gly | Pro | Asn<br>240 |
| Pro | Val | Leu | Ala | Asp<br>245 | Gln | Leu | Ser | Leu | Pro<br>250 | Arg | Pro | Asn | Pro | Leu<br>255 | Pro |
| Lys | Pro | Ala | Lys<br>260 | Ser | Pro | Pro | Ala | Ser<br>265 | Asn | Ser | Thr | Pro<br>270 | Thr | Leu | Ile |
| Ser | Pro | Ser<br>275 | Pro | Thr | Pro | Thr | Gln<br>280 | Pro | Pro | Pro | Ala | Gly<br>285 | Ala | Ser | Glx |
| Glx |     |     |     |     |     |     |     |     |     |     |     |     |     |     |     |

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

TCCTGGCGCC TCTAATTCGA CTCCCACATT     30

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

TTGCGGCGCC ACGGGAGACA GGTTACTAAA TC     32

(2) INFORMATION FOR SEQ ID NO:14:

(i) SEQUENCE CHARACTERISTICS:
        (A) LENGTH: 41 base pairs
        (B) TYPE: nucleic acid
        (C) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

ACTGATCGAT TCATTAGGCG CCGGATACCT TTGGACAGGC C                                    41

( 2 ) INFORMATION FOR SEQ ID NO:15:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

CATCGCTAGC GTAACGCACA GTTTAATTG TGGA                                             34

( 2 ) INFORMATION FOR SEQ ID NO:16:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

ACTGATCGAT CTATTAGGCG CCCCCTGTAA TATTTGAACA T                                    41

( 2 ) INFORMATION FOR SEQ ID NO:17:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

ACTGTCTAGA AAGCGCGCGA ACAGAAGCGA GAAGC                                           35

( 2 ) INFORMATION FOR SEQ ID NO:18:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide (iii) HYPOTHETICAL: NO (iv) ANTI-SENSE: NO (xi) SEQUENCE DESCRIPTION: SEQ ID NO:18:

Cys Trp Leu Cys
1

(2) INFORMATION FOR SEQ ID NO:19:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:19:

Cys Xaa Xaa Xaa Xaa Xaa Xaa Cys Cys
1               5

(2) INFORMATION FOR SEQ ID NO:20:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:20:

Ile Glu Gly Arg
1

(2) INFORMATION FOR SEQ ID NO:21:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (ix) FEATURE:
    (A) NAME/KEY: Modified-site
    (B) LOCATION: 1..5
    (D) OTHER INFORMATION: /label= Insert
        / note= "The complete insert comprises
        Ala-Ser- Heterologous Sequence-Gly-Ala. The
        Heterologous Sequence is denoted as Xaa"

(xi) SEQUENCE DESCRIPTION: SEQ ID NO:21:

Ala Ser Xaa Gly Ala
1               5

(2) INFORMATION FOR SEQ ID NO:22:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( i x ) FEATURE:
    ( A ) NAME/KEY: Peptide
    ( B ) LOCATION: 1..16
    ( D ) OTHER INFORMATION: /note= "An analogous peptide
        matching the consensus sequence for HXB2d V2
        domain and homologs with an additional C-terminal
        ( C y s ) as defined in the Los Alamos Human Retrovirus
        and AIDS database (ADP 794.1)."

( x i ) SEQUENCE DESCRIPTION: SEQ ID NO:22:

```
Ile Arg Asp Lys Val Gln Lys Glu Tyr Ala Leu Phe Tyr Lys Leu Cys
1               5                   10                  15
```

( 2 ) INFORMATION FOR SEQ ID NO:23:

( i ) SEQUENCE CHARACTERISTICS:
    ( A ) LENGTH: 34 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:23:

```
Thr Arg Pro Asn Asn Asn Thr Arg Lys Ser Ile Arg Ile Gln Arg Gly
1               5                   10                  15

Pro Gly Arg Ala Phe Val Thr Ile Gly Lys Ile Gly Asn Met Arg Gln
            20                  25                  30

Ala His
```

( 2 ) INFORMATION FOR SEQ ID NO:24:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:24:

```
Arg Lys Arg Ile His Ile Gly Pro Gly Arg Ala Phe Tyr Thr Thr Lys
1               5                   10                  15

Asn
```

( 2 ) INFORMATION FOR SEQ ID NO:25:

( i ) SEQUENCE CHARACTERISTICS:
    ( A ) LENGTH: 6 amino acids
    ( B ) TYPE: amino acid
    ( C ) STRANDEDNESS: single (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:25:

```
Leu  Val  Pro  Arg  Gly  Ser
1                   5
```